United States Patent
Melnick et al.

(10) Patent No.: US 9,592,223 B2
(45) Date of Patent: Mar. 14, 2017

(54) SMALL MOLECULE INHIBITORS OF MALT1

(71) Applicant: Cornell University, Ithaca, NY (US)

(72) Inventors: Ari Melnick, New York, NY (US); Hao Wu, Brookline, MA (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 14/439,621

(22) PCT Filed: Nov. 8, 2013

(86) PCT No.: PCT/US2013/069141
§ 371 (c)(1),
(2) Date: Apr. 29, 2015

(87) PCT Pub. No.: WO2014/074815
PCT Pub. Date: May 15, 2014

(65) Prior Publication Data
US 2015/0297570 A1    Oct. 22, 2015

Related U.S. Application Data

(60) Provisional application No. 61/724,650, filed on Nov. 9, 2012.

(51) Int. Cl.
*A61K 31/4196* (2006.01)
*A61K 31/426* (2006.01)
*C12Q 1/37* (2006.01)

(52) U.S. Cl.
CPC ........ *A61K 31/4196* (2013.01); *A61K 31/426* (2013.01); *C12Q 1/37* (2013.01); *G01N 2333/96466* (2013.01); *G01N 2500/04* (2013.01); *G01N 2500/20* (2013.01)

(58) Field of Classification Search
None
See application file for complete search history.

(56) References Cited

U.S. PATENT DOCUMENTS

| | | | |
|---|---|---|---|
| 4,746,669 | A | 5/1988 | Caldwell et al. |
| 6,399,603 | B1 | 6/2002 | Jacobs et al. |
| 6,632,962 | B2 | 10/2003 | Golec et al. |
| 7,276,477 | B2 | 10/2007 | Osslund |
| 7,572,886 | B2 | 8/2009 | Girard et al. |
| 8,063,083 | B2 | 11/2011 | Foley |
| 2004/0077878 | A1 | 4/2004 | Liu |
| 2009/0182027 | A1 | 7/2009 | Palladino et al. |
| 2011/0021548 | A1 | 1/2011 | Beyaert et al. |
| 2013/0225490 | A1 | 8/2013 | Sims et al. |

FOREIGN PATENT DOCUMENTS

| | | |
|---|---|---|
| DE | 102010013716 A1 | 10/2011 |
| JP | 2002-530079 A | 9/2002 |
| JP | 2003-506389 A | 2/2003 |
| JP | 2003-509501 A | 3/2003 |
| JP | 2005-527191 A | 9/2005 |
| JP | 2007-521315 A | 8/2007 |
| JP | 2007-523862 A | 8/2007 |
| WO | WO-99/62891 A1 | 12/1999 |
| WO | WO-03/040110 A1 | 5/2003 |
| WO | WO-2006123242 A1 | 11/2006 |
| WO | WO-2011/020849 A1 | 2/2011 |
| WO | WO-2014074815 A1 | 5/2014 |

OTHER PUBLICATIONS

International Application Serial No. PCT/US2013/069141, International Search Report mailed Mar. 7, 2014, 3 pgs.
International Application Serial No. PCT/US2013/069141, Written Opinion mailed Mar. 7, 2014, 4 pgs.
Deng, X, et al., "Discovery of 3,5-Diamino-1,2,4-triazole Ureas as Potent Anaplastic Lymphoma Kinase Inhibitors", ACS Medicinal Chemistry Letters, vol. 2., (Mar. 15, 2011), 379-384.
Fontan, L, et al., "MALT1 Small Molecule Inhibitors Specifically Suppress ABC-DLBCL In Vitro and In Vivo. Cancer Cell", second column, lines 11-6, vol. 22., (Dec. 11, 2012), 812-824.
Australian Application Serial No. 2013342267, Examination Report No. 1 mailed Mar. 18, 2016, 3 pgs.
Chinese Application Serial No. 201380069677.4, Office Action mailed Mar. 7, 2016, (w English Translation), 14 pgs.
European Application Serial No. 13853142.1, Office Action mailed Aug. 11, 2015, 2 pgs.
European Application Serial No. 13853142.1, Partial European Search Report mailed Apr. 26, 2016, 7 pgs.
European Application Serial No. 13853142.1, Response filed Jun. 24, 2016 to Office Action mailed Apr. 26, 2016, 2 pgs.
International Application Serial No. PCT/US2013/069141, International Preliminary Report on Patentability mailed May 21, 2015, 6 pgs.
Japanese Application Serial No. 2015-541923, Office Action mailed Jul. 5, 2016, (w/ English Translation), 9 pgs.

(Continued)

*Primary Examiner* — Samantha Shterengarts
(74) *Attorney, Agent, or Firm* — Schwegman Lundberg & Woessner, P.A.

(57) ABSTRACT

MALT1 cleavage activity is linked to the pathogenesis of activated B-cell-like diffuse large B-cell lymphoma (ABC-DLBCL), a chemo-resistant form of DLBCL. We developed a MALT1 activity assay and identified chemically diverse MALT1 inhibitors. A selected lead compound MI-2 featured direct binding to MALT1 and suppression of its protease function. MI-2 concentrated within human ABC-DLBCL cells and irreversibly inhibited cleavage of MALT1 substrates. This was accompanied by suppression of NF-κB reporter activity, inhibition of nuclear localization of c-REL and downregulation of NF-κB target gene signature. Most notably, MI-2 was non-toxic to mice, and displayed potent and specific activity against ABC-DLBCL cell lines in vitro, and xenotransplanted ABC-DLBCL tumors in vivo. The compound was also effective against primary human non-GCB-DLBCLs ex vivo.

14 Claims, 28 Drawing Sheets

(56) References Cited

OTHER PUBLICATIONS

Singaporean Application Serial No. 11201503642Y, Written Opinion mailed Feb. 2, 2016, 7 pgs.
Alizadeh, Ash A., et al., "Distinct types of diffuse large B-cell lymphoma identified by gene expression profiling", Nature, 403(6769), (Feb. 3, 2000), 503-511.
Bill, Anke, et al., "Anti-Proliferative Effect of Cytohesin Inhibition in Gefitinib-Resistant Lung Cancer Cells", PLoS ONE, 7(7), (2012), 8 pgs.
Boatright, Kelly M., et al., "A Unified Model for Apical Caspase Activation", Molecular Cell, vol. 11, (Feb. 2003), 529-541.
Cerchietti, Leandro ., et al., "A peptomimetic inhibitor of BCL6 with potent antilymphoma effects in vitro and in vivo", Blood, 113(15), (2009), 3397-3405.
Cerchietti, Leandro C., et al., "A Small-Molecule Inhibitor of BCL6 Kills DLBCL Cells In Vitro and In Vivo", Cancer Cell, 17(4), (2010), 400-411.
Cerchietti, Leandro C., et al., "BCL6 repression of EP300 in human diffuse large B cell lymphoma cells provides a basis for rational combinatorial therapy", The Journal of Clinical Investigation, 120(Dec. 2010), 4569-4582.
Compagno, Mara, et al., "Mutations of multiple genes cause deregulation of NF-κB in diffuse large B-cell lymphoma", Nature, vol. 459, (2009), 717-721.
Coornaert, Beatrice, et al., "T cell antigen receptor stimulation induces MALT1 paracaspase-mediated cleavage of the NF-κb inhibitor A20", Nature Immunology, 9(3), (Mar. 2008), 263-271.
Davis, R. Eric, et al., "Chronic active B-cell-receptor signalling in diffuse large B-cell lymphoma", Nature, vol. 463, (2010), 88-92.
Dierlamm, Judith, et al., "Gain of chromosome region 18q21 including the MALT1 gene is associated with the activated B-cell-like geneexpression subtype and increased BCL2 gene dosage and protein expression in diffuse large B-cell lymphoma", Haematologica, 93(5), (2008), 688-696.
Dierlamm, Judith, et al., "The Apoptosis Inhibitor Gene API2 and a Novel 18q Gene, MLT, Are Recurrently Rearranged in the t(11;18)(q21;q21) Associated With Mucosa-Associated Lymphoid Tissue Lymphomas", Blood, 93(11), (1999), 3601-3609.
Du, Pan, et al., "lumi: a pipeline for processing Illumina microarray", Bioinformatics, 24(13), (2008), 1547-1548.
Farinha, Pedro, et al., "Molecular Pathogenesis of Mucosa-Associated Lymphoid Tissue Lymphoma", Journal of Clinical Oncology, 23(26), (2005), 6370-6378.
Ferch, Uta, et al., "Inhibition of MALT1 protease activity is selectively toxic for activated B cell-like diffuse large B cell lymphoma cells", The Journal of Experimental Medicine, 206(11), (2009), 2313-2320.
Ferch, Uta, et al., "MALT1 directs B cell receptor-induced canonical nuclear factor-κB signaling selectively to the c-Rel subunit", Nature Immunology, 8(9), (Sep. 2007), 984-991.
Gavrieli, Yael, et al., "Identification of Programmed Cell Death In Situ via Specific Labeling of Nuclear DNA Fragmentation", The Journal of Cell Biology, 119 (3), (Nov. 1992), 493-501.
Genin, E., et al., "Proteasome Inhibitors: Recent Advances and New Perspectives in Medicinal Chemistry", Current Topics in Medicinal Chemistry,10, (2010), 232-256.
Gross, Olaf, et al., "Multiple ITAM-coupled NK-cell receptors engage the Bcl10/Malt1 complex via Carma1 for NF-B and MAPK activation to selectively control cytokine production", Blood, 112(6), (2008), 2421-2428.
Hachmann, Janna, et al., "Mechanism and specificity of the human paracaspase MALT1", Biochem. J., 443, (2012), 287-295.
Hailfinger, Stephan, et al., "Essential role of MALT1 protease activity in activated B cell-like diffuse large B-cell lymphoma", Proc. Natl. Acad. Sci. USA, 106(47) (with Corrections), (2009), 19946-19951.
Hailfinger, Stephan, et al., "Malt1-dependent RelB cleavage promotes canonical NF-κB activation in lymphocytes and lymphoma cell lines", Proc. Natl. Acad. Sci. USA, 108(35), (2011), 14596-14601.
Hans, Christine P., et al., "Confirmation of the molecular classification of diffuse large B-cell lymphoma by immunohistochemistry using a tissue microarray", Blood, 103(1), (2004), 275-282.
Honigberg, Lee A., et al., "The Bruton tyrosine kinase inhibitor PCI-32765 blocks B-cell activation and is efficacious in models of autoimmune disease and B-cell malignancy", Proc. Natl. Acad. Sci. USA, 107(29), (2010), 13075-13080.
Honma, Keiichiro, et al., "TNFAIP3/A20 functions as a novel tumor suppressor gene in several subtypes of non-Hodgkin lymphomas", Blood, 114(12), (2009), 2467-2475.
Klibanov, Olga M., et al., "Telaprevir: A Novel NS3/4 Protease Inhibitor for the Treatment of Hepatitis C", Pharmacotherapy;31(10), (2011), 951-971.
Lam, Lloyd T., et al., "Small molecule inhibitors of IkappaB kinase are selectively toxic for subgroups of diffuse large B-cell lymphoma defined by gene expression profiling", Clinical Cancer Research, 11, (2005), 28-40.
Lenz, Georg, et al., "Aggressive Lymphomas", The New England Journal of Medicine, 362, (2010), 1417-1429.
Lenz, Georg, et al., "Molecular subtypes of diffuse large B-cell lymphoma arise by distinct genetic pathways", Proc. Natl. Acad. Sci. USA., 105(36), (2008), 13520-13525.
Lenz, Georg, et al., "Oncogenic CARD11 Mutations in Human Diffuse Large B Cell Lymphoma", Science, 319, (2008), 1676-1679.
Lim, Kian-Huat, et al., "Pathogenetic importance and therapeutic implications of NF-κB in lymphoid malignancies", Immunological Reviews, 246, (2012), 359-378.
Lucas, Peter C., et al., "Bcl10 and MALT1, Independent Targets of Chromosomal Translocation in MALT Lymphoma, Cooperate in a Novel NF-κB Signaling Pathway", The Journal of Biological Chemistry, 276(22), (2001), 19012-19019.
Manicassamy, Santhakumar, et al., "Sotrastaurin, a protein kinase C inhibitor for the prevention of transplant rejection and treatment of psoriasis", Current Opinion in Investigational Drugs,10(11), (2009), 1225-1235.
Matz, Mareen, et al., "Evaluation of the novel protein kinase C inhibitor sotrastaurin as immunosuppressive therapy after renal transplantation", Expert Opinion on Drug Metabolism & Toxicology, 7(1), (2011), 103-113.
Misale, Sandra, et al., "Emergence of KRAS mutations and acquired resistance to anti-EGFR therapy in colorectal cancer", Nature, 486(7404), (2012), 532-535.
Morris, Garrett M., et al., "AutoDock4 and AutoDockTools4: Automated Docking with Selective Receptor Flexibility", Journal of Computational Chemistry, 30, (2009), 2785-2791.
Naylor, Tara L., et al., "Protein Kinase C Inhibitor Sotrastaurin Selectively Inhibits the Growth of CD79 Mutant Diffuse Large B-Cell Lymphomas", Cancer Research, 71(7), (2011), 2643-2653.
Ngo, Vu N., et al., "A loss-of-function RNA interference screen for molecular targets in cancer", Nature, 441, (2006), 106-110.
Ngo, Vu N., et al., "Oncogenically active MYD88 mutations in human lymphoma", Nature, 470, (Feb. 2011), 115-119.
Polo, Jose M., et al., "Specific peptide interference reveals BCL6 transcriptional and oncogenic mechanisms in B-cell lymphoma cells", Nature Medicine, 10(12), (Dec. 2004), 1329-1335.
Pop, Cristina, et al., "The Apoptosome Activates Caspase-9 by Dimerization", Molecular Cell, 22, (2006), 269-275.
Powers, James C., et al., "Irreversible Inhibitors of Serine, Cysteine, and Threonine Proteases", Chem. Rev., 102, (2002), 4639-4750.
Rebeaud, Fabien, et al., "The proteolytic activity of the paracaspase MALT1 is key in T cell activation", Nature Immunology, 9, (2008), 272-281.
Rosenwald, Andreas, et al., "Molecular Diagnosis of Primary Mediastinal B Cell Lymphoma Identifies a Clinically Favorable Subgroup of Diffuse Large B Cell Lymphoma Related to Hodgkin Lymphoma", The Journal of Experimental Medicine, 198(6), (2003), 851-862.

(56) References Cited

OTHER PUBLICATIONS

Rosenwald, Andreas, et al., "The use of molecular profiling to predict survival after chemotherapy for diffuse large-B-cell lymphoma", The New England Journal of Medicine, 346(25), (2002), 1937-1947.

Ruefli-Brasse, Astrid A., et al., "Regulation of NF-κB-Dependent Lymphocyte Activation and Development by Paracaspase", Science, 302, (2003), 1581-1584.

Ruland, Jurgen, et al., "Differential Requirement for Malt1 in T and B Cell Antigen Receptor Signaling", Immunity, vol. 19, (Nov. 2003), 749-758.

Sanchez-Izquierdo, Dolors, et al., "MALT1 is deregulated by both chromosomal translocation and amplification in B-cell non-Hodgkin lymphoma", Blood, 101(11), (2003), 4539-4546.

Siegel, Rebecca, "Cancer Statistics, 2012", CA: A Cancer Journal for Clinicians, (2012), 10-29.

Staal, Jens, et al., "T-cell receptor-induced JNK activation requires proteolytic inactivation of CYLD by MALT1", The EMBO Journal, 30, (2011), 1742-1752.

Storey, John D., et al., "Statistical significance for genomewide studies", Proc. Natl. Acad. Sci., 100(16), (2003), 9440-9445.

Streubel, Berthold, et al., "T(14;18)(q32;q21) involving IGH and MALT1 is a frequent chromosomal aberration in MALT lymphoma", Blood, 101(6), (2003), 2335-2339.

Subramanian, Aravind, et al., "Gene set enrichment analysis: a knowledge-based approach for interpreting genome-wide expression profiles", Proc. Natl. Acad. Sci. USA, 102(43), (2005), 15545-15550.

Swerdlow, Steven H., et al., "World Health Organization Classification of Tumours of Haematopoietic and Lymphoid Tissues", Lyon: IARC Press), (2008), 9 pgs.

Vicente-Duenas, Carolina, et al., "Expression of MALT1 oncogene in hematopoietic stem/progenitor cells recapitulates the pathogenesis of human lymphoma in mice", Proc. Natl. Acad. Sci. USA, 109(26), (2012), 10534-10539.

Walker, N. P. C., et al., "Crystal Structure of the Cysteine Protease Interleukin-1β-Converting Enzyme: A (p20/p10)2 Homodimer", Cell, 78, (1994), 343-352.

Wiesmann, Christian, et al., "Structural Determinants of MALT1 Protease Activity", J. Mol. Biol., 419, (2012), 4-21.

Wright, George, et al., "A gene expression-based method to diagnose clinically distinct subgroups of diffuse large B cell lymphoma", Proc. Natl. Acad. USA, 100(17), (2003), 9991-9996.

Yin, Qian, et al., "Caspase-9 Holoenzyme Is a Specific and Optimal Procaspase-3 Processing Machine", Molecular Cell, 22, (2006), 259-268.

Yu, Jong W., et al., "Crystal structure of the mucosa-associated lymphoid tissue lymphoma translocation 1 (MALT1) paracaspase region", Proc. Natl. Acad. Sci. USA, 108(52), (2011), 21004-21009.

Zhang, Ji-Hu, et al., "A Simple Statistical Parameter for Use in Evaluation and Validation of High Throughput Screeing Assats", Journal of Biomedical Screening, 4(2), (1999), 67-73.

Australian Application Serial No. 2013342267, Response filed Aug. 15, 2016 to Examination Report No. 1 mailed Mar. 18, 2016, 26 pgs.

Australian Application Serial No. 2013342267, Subsequent Examiners Report mailed Aug. 16, 2016, 3 pgs.

Eurasian Application Serial No. 201590916, Office Action mailed Aug. 6, 2016, (w/ English Translation), 4 pgs.

European Application Serial No. 13853142.1, Extended European Search Report mailed Aug. 12, 2016, 13 pgs.

Singapore Application Serial No. 11201503642Y, Written Opinion mailed Jul. 14, 2016, 6 pgs.

"Australian Application Serial No. 2013342267, Response filed Dec. 7, 2016 to Subsequent Examiners Report mailed Aug. 16, 2016", 27 pgs.

"Australian Application Serial No. 2013342267, Statement of Proposed Amendments filed Dec. 7, 2016 in response to Subsequent Examiners Report mailed Aug. 16, 2016", 27 pgs.

"Chinese Application Serial No. 201380069677.4, Office Action mailed Nov. 11, 2016", (w/ English Translation), 16 pgs.

"Eurasian Application Serial No. 201590916, Response filed Dec. 6, 2016 to Office Action mailed Aug. 6, 2016", (w/ English Translation of Claims), 23 pgs.

"Singapore Application Serial No. 11201503642Y, Response filed Dec. 19, 2016 to Second Written Opinion mailed Jul. 18, 2016", 17 pgs.

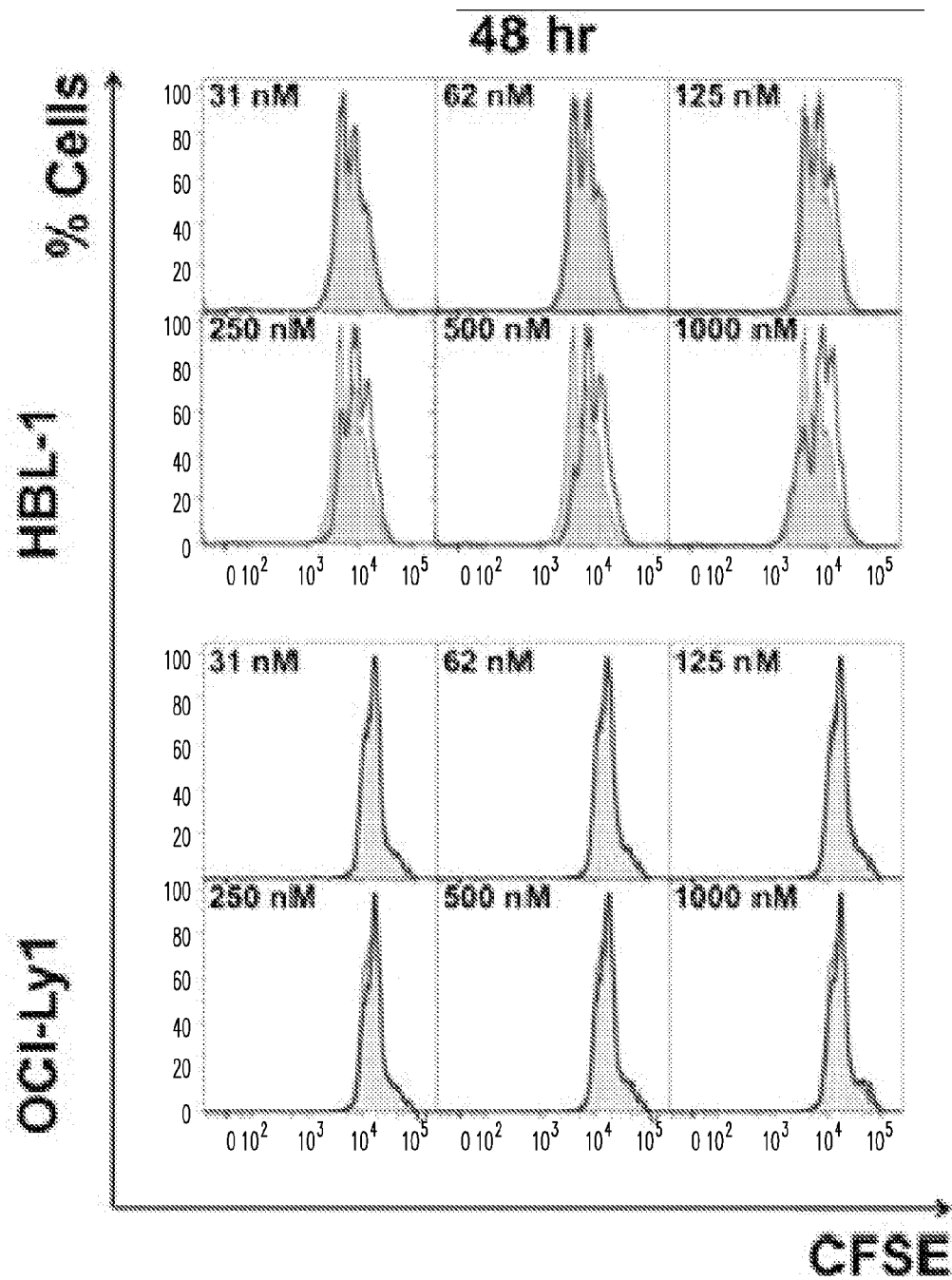
Fig.5C1

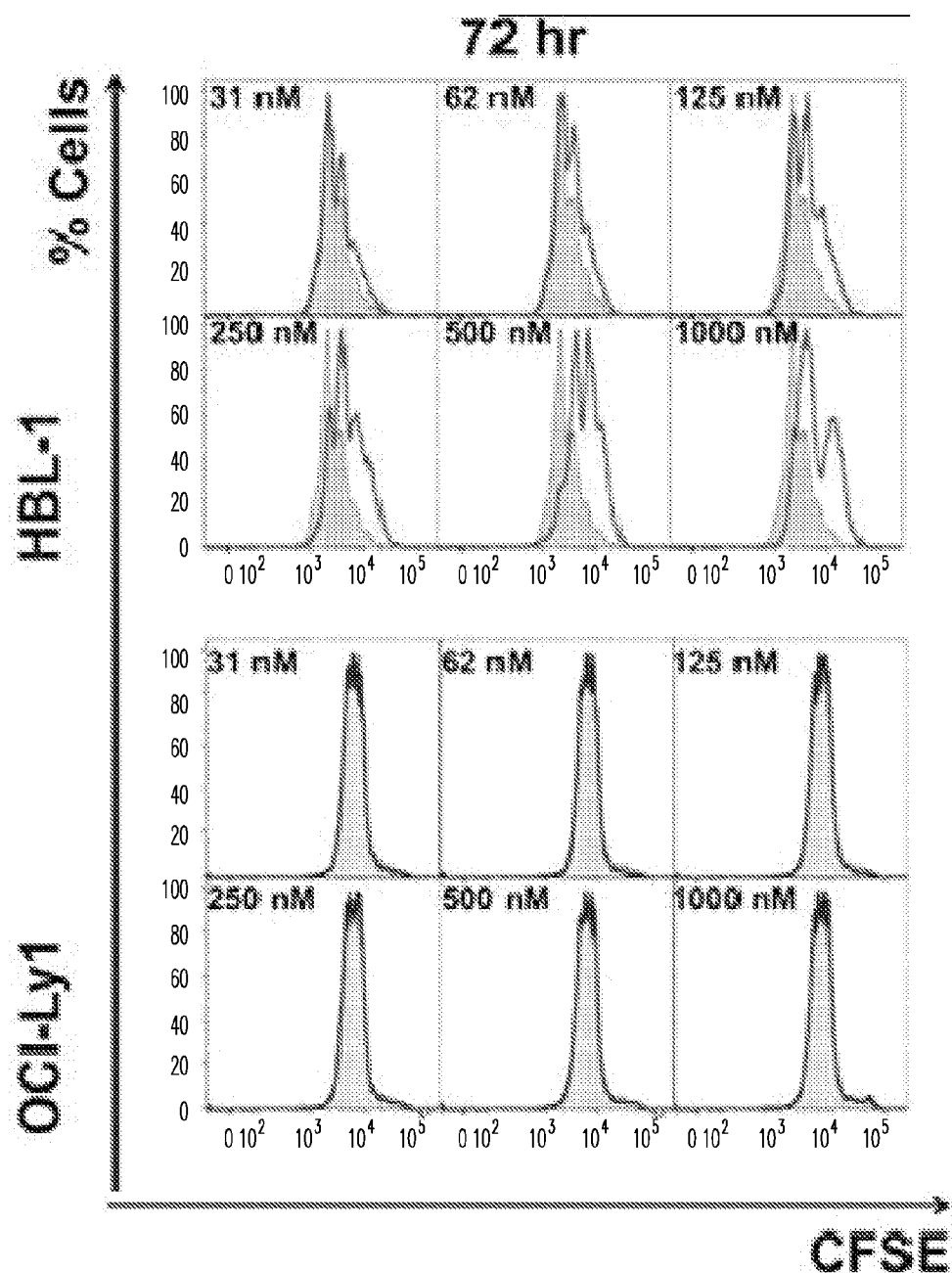
Fig.5C2

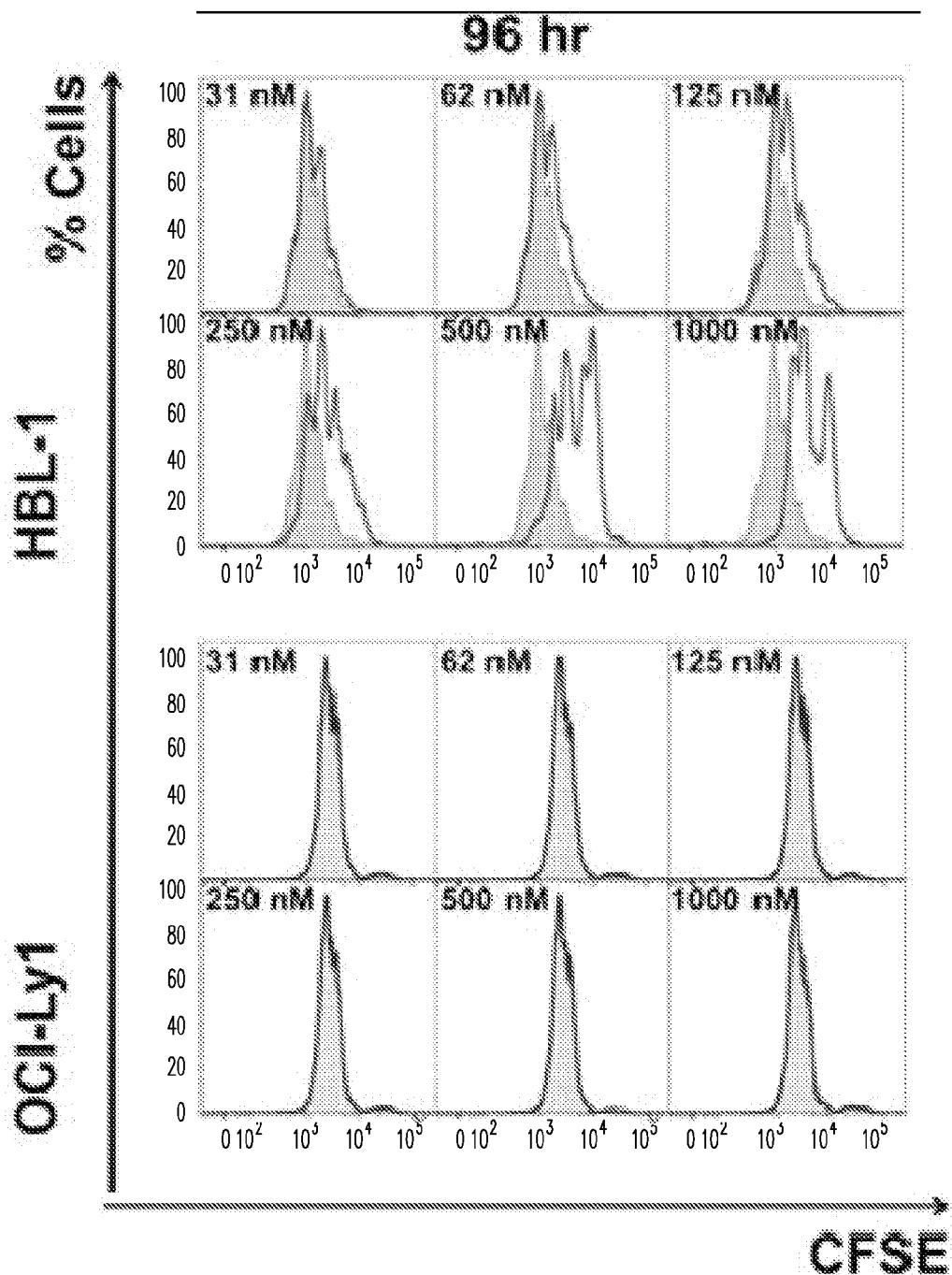
Fig.5C3

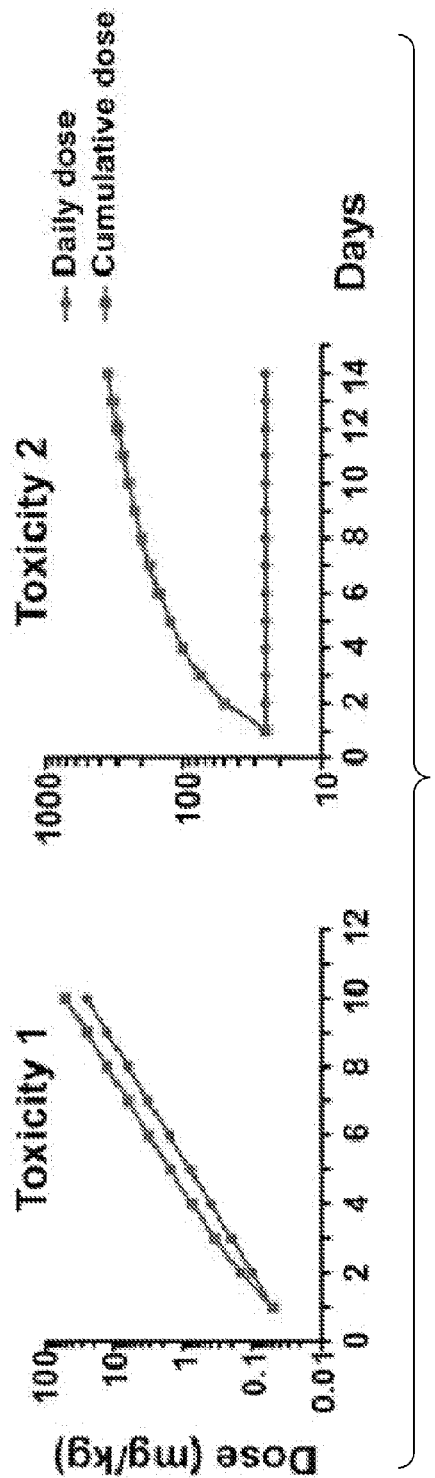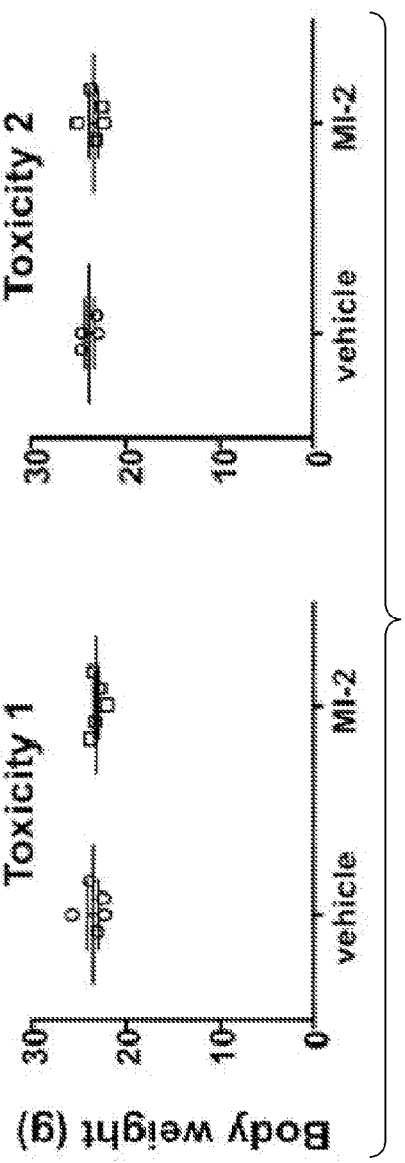
Fig. 6A
Fig. 6B

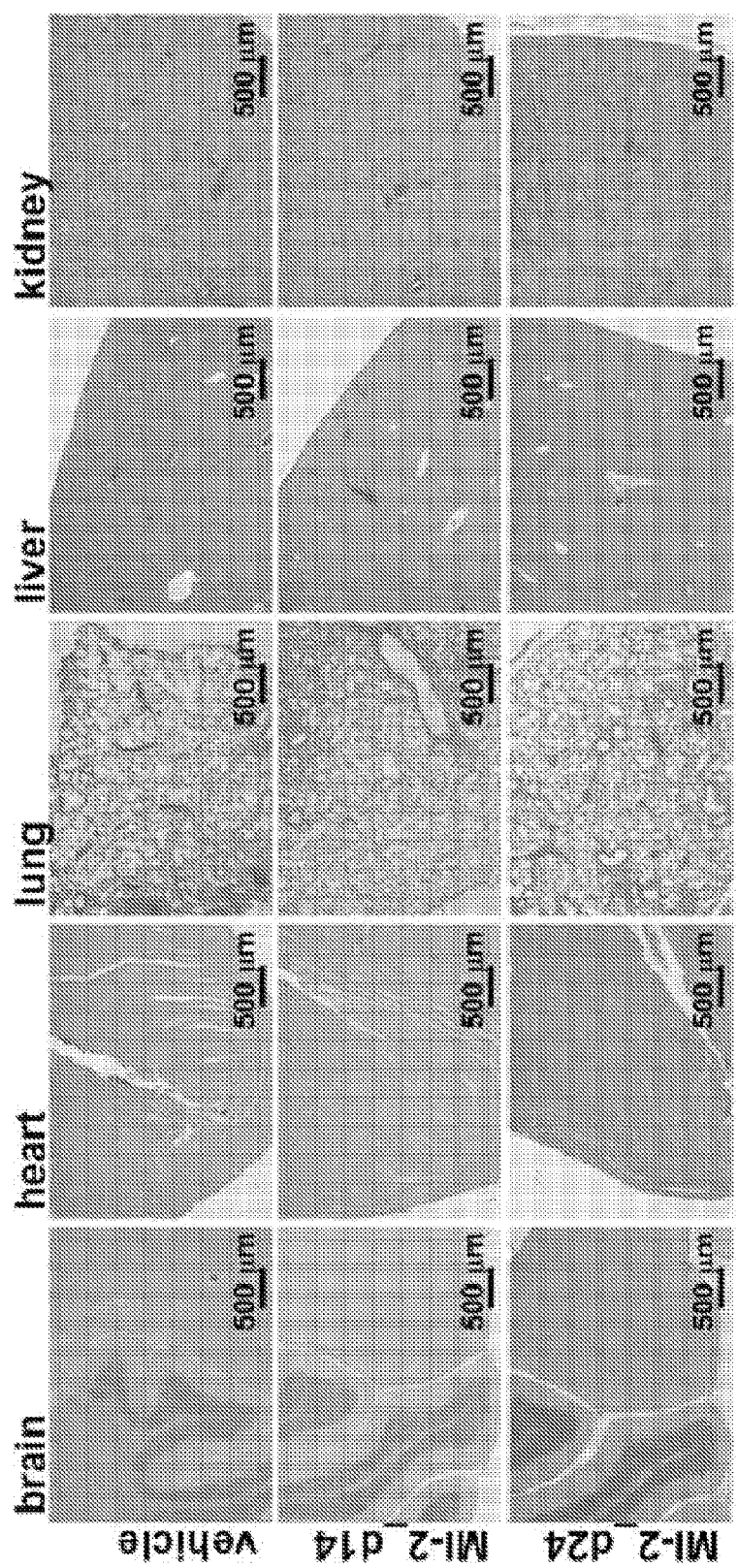
Fig. 6C1

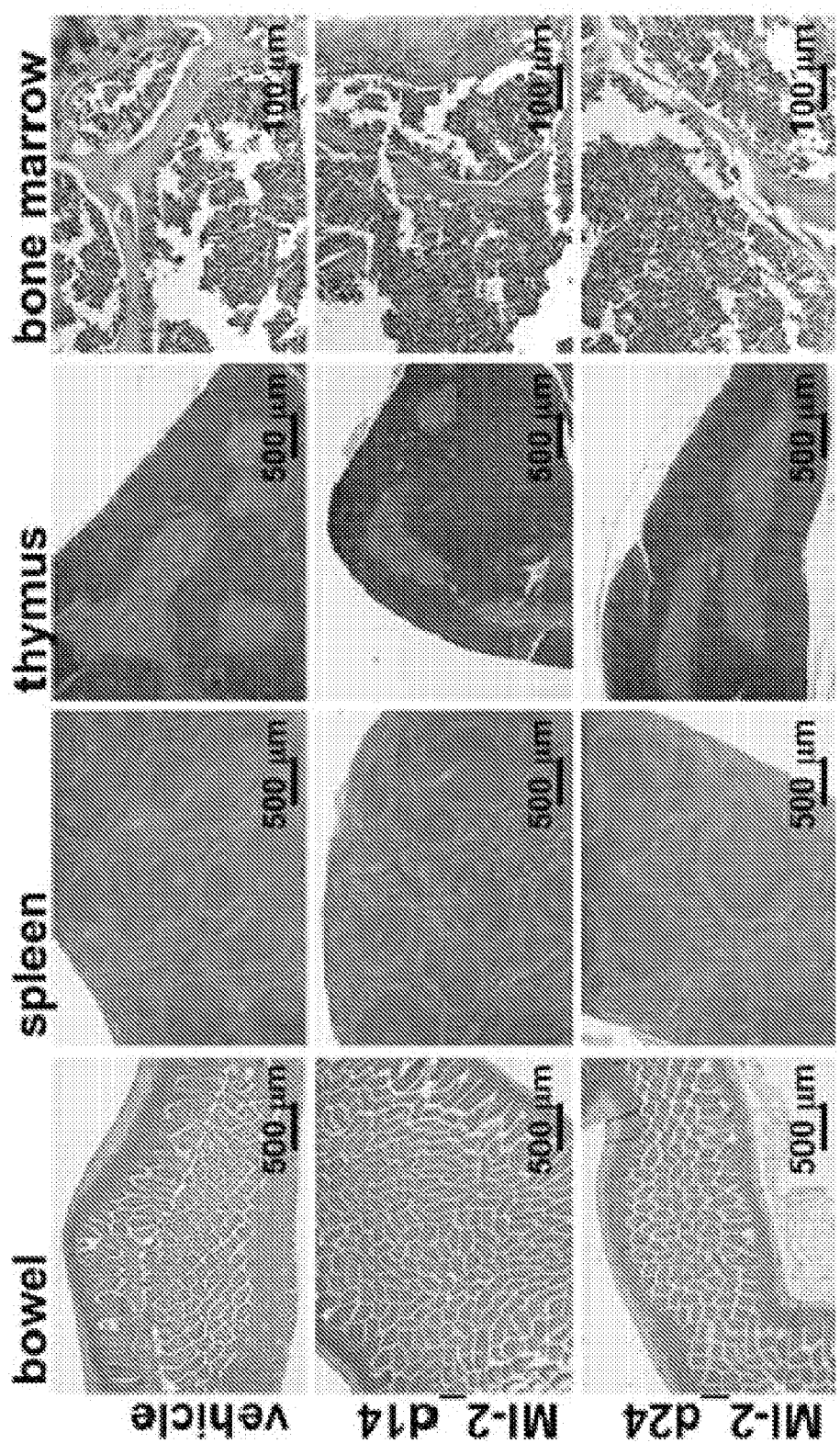
Fig. 6C2 vehicle c-REL

DAPI

MI-2 c-REL

DAPI

SMALL MOLECULE INHIBITORS OF MALT1

CROSS-REFERENCE TO RELATED APPLICATIONS

This application is a U.S. National Stage Filing under 35 U.S.C. 371 from International Application No. PCT/US2013/069141, filed 8 Nov. 2013, and published as WO 2014/074815 on 15 May 2014, which claims priority to U.S. provisional patent application Ser. No. 61/724,650, filed Nov. 9, 2012, the contents of which applications and publication are incorporated herein by reference in their entirety.

BACKGROUND

Non-Hodgkin lymphoma (NHL) is the 7th most frequent cancer (Siegel et al., 2012). Diffuse large B-cell lymphoma (DLBCL) is the most common subtype of NHL accounting for ~25% of all lymphoma cases (Swerdlow, 2008). Gene expression profiling allowed subclassification of DLBCL into distinct molecular subtypes including: germinal center B-cell-like (GCB) DLBCL, activated B-cell-like (ABC) DLBCL and primary mediastinal B-cell lymphoma (PMBL) (Alizadeh et al., 2000; Rosenwald et al., 2003). These subtypes differ significantly in their spectrum of recurrent somatic mutations, dependence on different signaling pathways and response to current standard therapies (Lenz et al., 2008b; Wright et al., 2003). Patients with the GCB subtype have a significantly better overall survival compared to those with the ABC subtype (Alizadeh et al., 2000; Rosenwald et al., 2002). Improved therapies are needed for all DLBCLs but most urgently for ABC-DLBCLs, which are the most chemo-resistant.

ABC-DLBCL is characterized by its reliance on the oncogenic activation of the NF-κB pathway through several different mechanisms. These mostly involve somatic mutations in molecules participating in signaling downstream of the B-cell receptor (BCR) including: activating mutations of CARMA1/CARD11 (Lenz et al., 2008a) and CD79A/B (Davis et al., 2010), homozygous deletion/inactivating mutations of TNFAIP3/A20 (Compagno et al., 2009; Honma et al., 2009) or activating mutations of MYD88 downstream of the Toll-like receptor (Ngo et al., 2011). CARMA1 forms part of the CBM complex (CARMA1-BCL10-MALT1) and mediates NF-κB activation downstream of the B-cell receptor, T-cell receptor (Ruefli-Brasse et al., 2003; Ruland et al., 2003) and ITAM-coupled NK cell receptors (Gross et al., 2008). The MALT1 subunit is the active signaling component of the CBM complex (Lucas et al., 2001) and features protease activity that cleaves and inactivates inhibitors of the NF-κB signaling pathway such as TNFAIP3/A20 (Coornaert et al., 2008), CYLD (Staal et al., 2011) and RELB (Hailfinger et al., 2011) or the BCL10 protein (Rebeaud et al., 2008), indirectly activating NF-κB signaling. MALT1 translocations (t(11; 18)(q21; q21) which produces an API2-MALT1 fusion and the t(14; 18)(q32; q21) that results in the IGH-MALT1 translocation) are detected in up to 55% of patients with MALT-type lymphomas (Farinha and Gascoyne, 2005). This translocations lead to overexpression of MALT1 and, in the case of the API2-MALT1 translocation, constitutive activation of the pathway (Dierlamm et al., 1999; Sanchez-Izquierdo et al., 2003; Streubel et al., 2003). Constitutive expression of MALT1 in mice induces a disease that is similar to MALT lymphomas in humans, and induces ABC-like DLBCLs in a p53 null background (Vicente-Duenas et al., 2012). MALT1 has not been found mutated or translocated in DLBCL, but is gained along with BCL2 and this low copy number amplification is associated with an ABC-DLBCL phenotype (Dierlamm et al., 2008). Moreover, ABC-DLBCL cell lines have been shown to be dependent on the MALT1 catalytic activity (Ferch et al., 2009; Hailfinger et al., 2009; Ngo et al., 2006).

MALT1 is a paracaspase, related to the caspase (cysteine-aspartic proteases) family of proteases but which cleaves after arginine or lysine residues instead of aspartate (Rebeaud et al., 2008). MALT1 null animals display defects in B and T cell function but are otherwise healthy (Ruefli-Brasse et al., 2003; Ruland et al., 2003), and MALT1 is the only paracaspase in the human genome. These factors suggest that MALT1 targeted therapy would likely be well tolerated with little or manageable toxicity. Consequently, MALT1 represents a potentially important therapeutic target for ABC-DLBCL and MALT lymphoma.

SUMMARY

MALT1 is a unique paracaspase protein that transduces aberrant oncogenic signaling in ABC-DLBCL. The inventors disclose herein the development of a constitutively activated form of MALT1 that enabled a screen for small molecule inhibitors, and claim MALT1 inhibitory compounds and their use for treatment of medical disorders such as B-cell lymphomas. The compound MI-2, an irreversible MALT1 protease inhibitor, was identified as a lead compound with nanomolar activity in cell-based assays and selective activity against ABC-DLBCLs. Importantly we show that MALT1 inhibitors kill ABC-DLBCLs in vitro and in vivo, are non-toxic to animals and also suppress primary human non GCB-DLBCL specimens. Hence we demonstrate that MALT1 is a bona fide therapeutic target, and provide a lead compound that forms the basis of a new class of therapeutic agents for B-cell lymphomas.

The invention provides, in various embodiments, a method of modulating MALT1, comprising contacting MALT1 with an effective amount or concentration of a compound of formula (I)

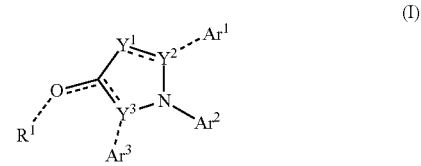

wherein
a dashed bond indicates that a bond can be present or absent;
when a double bond is present between $Y^1$ and $Y^2$, $Y^1$ is N or CR, $Y^2$ is C, and $Ar^1$ is present; when a single bond is present between $Y^1$ and $Y^2$, $Y^1$ is $CR_2$, $Y^2$ is O or S, and $Ar^1$ is absent, and each independently selected R is H or (C1-C6)alkyl;
$R^1$ is alkyl, alkoxyalkyl, or arylalkyl, wherein any alkyl, alkoxyalkyl, or arylalkyl, can be mono- or independently multi-substituted with halo or (C1-C6)alkoxy, provided that when a double bond is present between the oxygen atom and the ring comprising $Y^3$, $R^1$ is absent and $Ar^3$ is present, and when a single bond is present between the oxygen atom and the ring, $R^1$ is present, a double bond between $Y^3$ and the carbon atom bearing the oxygen atom is present, and $Ar^3$ is absent;

Ar$^1$ is phenyl substituted with 1-3 J$^1$ groups; J$^1$ is halo or (C1-C6)alkoxy;

Ar$^2$ is phenyl substituted with 1-3 J$^2$ groups; J$^2$ is a group of formula —N(R)C(O)—R$^2$ and R$^2$ is alkyl, aryl, or arylamino, wherein any alkyl, aryl, or arylamino is substituted with 0-2 halo, nitro, or (C1-C6)alkoxy groups;

Ar$^3$ is phenyl substituted with 1-3 J$^3$ groups; J$^3$ is halo or (C1-C6)alkoxy;

or any salt, hydrate, tautomer, or stereoisomer thereof.

The invention further provides, in various embodiments, a method of treating or preventing cancer comprising administering to a patient an effective dose of a compound of formula (I) as defined above. More specifically, the cancer can be a lymphoma, such as a diffuse large B-cell lymphoma (DLBCL).

The invention further provides, in various embodiments, a method of identifying a small molecule modulator of MALT1, comprising contacting a recombinant form of MALT1 (340-789) fused with a leucine zipper dimerization motif (LZ-MALT1) and a candidate modulator compound, using the MALT1 substrate peptide LRSR linked to the fluorogen AMC (7-amino-4-methylcoumarin), such that cleavage of the Ac-LRSR-AMC substrate by MALT1 results in release of AMC and a fluorescent signal, wherein a decrease in the cleavage of the Ac-LRSR-AMC substrate by the recombinant form of MALT1 in the presence of the candidate modulator indicates that the candidate modulator is a small molecule modulator of MALT1.

BRIEF DESCRIPTION OF THE FIGURES

FIGS. 5C1, 5C2, and 5C3, show results of experiments wherein HBL-1, TMD8, OCI-Ly10 and the GCB-DLBCL cell line OCI-Ly1 were treated with increasing concentrations of MI-2. Cell proliferation was examined using the CFSE dilution assay by flow cytometry on viable cells at 48, 72 and 96 h. MI-2 substantially inhibited proliferation in HBL-1, TMD8 and OCI-Ly10 while it did not affect OCI-Ly1.

FIG. 6 shows results of experiments wherein five C57BL/6 mice were exposed to daily intraperitoneal (IP) administration of increasing doses of MI-2 ranging from 0.05 to 25 mg/kg over the course of 10 days to a cumulative dose of 51.1 mg/kg and another five mice were exposed to vehicle only (5% DMSO, n=5) (FIG. 6A, Toxicity 1). There was no evidence of lethargy, weight loss (FIG. 6B, Toxicity 1) or other physical indicators of sickness. To ascertain if the maximal administered dose of 25 mg/kg is safe in a 14-day schedule, we exposed ten mice to daily IP administration of 25 mg/kg of MI-2 over 14 days to a cumulative dose of 350 mg/kg, using as controls five mice injected with vehicle only (FIG. 6A, Toxicity 2). Five mice were sacrificed after the 14-day course of MI-2 administration (together with the 5 controls) and the other 5 mice were sacrificed after a 10-day washout period to assess delayed toxicity. No toxic effects or other indicators of sickness, including weight loss (FIG. 6B, Toxicity 2) or tissue damage (macroscopic or microscopic), were noted (FIGS. 6C1 and 6C2). Brain, heart, lung, liver, kidney, bowel, spleen, thymus and bone marrow tissues were examined.

DETAILED DESCRIPTION

Overview

Figure 1A:
FIG. 1A depicts two perspective views of the structure of a recombinant form of MALT1 (340-789) fused with a leucine zipper dimerization motif (LZ-MALT1), which promotes its dimerization and activation.

In various embodiments, the present invention provides a method of modulating MALT1, comprising contacting MALT1 with an effective amount or concentration of a compound of formula (I)

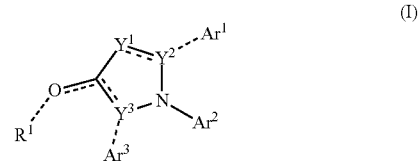

wherein a dashed bond indicates that a bond can be present or absent;

when a double bond is present between $Y^1$ and $Y^2$, $Y^1$ is N or CR, $Y^2$ is C, and $Ar^1$ is present; when a single bond is present between $Y^1$ and $Y^2$, $Y^1$ is $CR_2$, $Y^2$ is O or S, and $Ar^1$ is absent, and each independently selected R is H or (C1-C6)alkyl;

$R^1$ is alkyl, alkoxyalkyl, or arylalkyl, wherein any alkyl, alkoxyalkyl, or arylalkyl, can be mono- or independently multi-substituted with halo or (C1-C6)alkoxy, provided that when a double bond is present between the oxygen atom and the ring comprising $Y^3$, $R^1$ is absent and $Ar^3$ is present, and when a single bond is present between the oxygen atom and the ring, $R^1$ is present, a double bond between $Y^3$ and the carbon atom bearing the oxygen atom is present, and $Ar^3$ is absent;

$Ar^1$ is phenyl substituted with 1-3 $J^1$ groups; $J^1$ is halo or (C1-C6)alkoxy;

$Ar^2$ is phenyl substituted with 1-3 $J^2$ groups; $J^2$ is a group of formula —N(R)C(O)—$R^2$ and $R^2$ is alkyl, aryl, or arylamino, wherein any alkyl, aryl, or arylamino is substituted with 0-2 halo, nitro, or (C1-C6)alkoxy groups;

$Ar^3$ is phenyl substituted with 1-3 $J^3$ groups; $J^3$ is halo or (C1-C6)alkoxy;

or any salt, hydrate, tautomer, or stereoisomer thereof.

More specifically, the compound of formula (I) can be a compound of formula (IA)

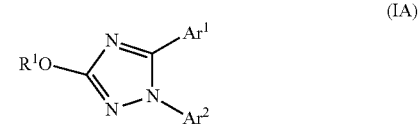

wherein $R^1$, $Ar^1$, and $Ar^2$ are as defined for the compound of formula (I), or any salt, hydrate, tautomer, or stereoisomer thereof.

More specifically, the compound of formula (I) can be a compound of formula (IB)

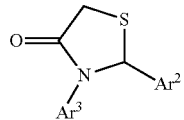
(IB)

wherein Ar² and Ar³ are as defined for the compound of formula (I), or any salt, hydrate, tautomer, or stereoisomer thereof.

For instance, the compound of formula (I) used to carry out a method of the invention can be any of

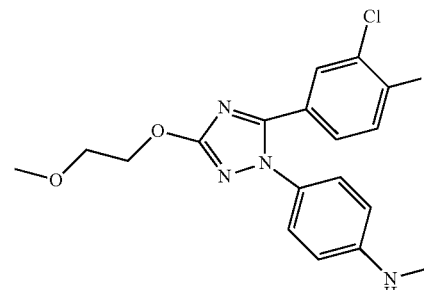
(MI-2)

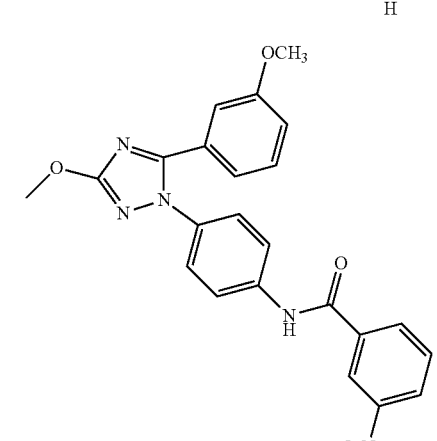
(MI-2A1)

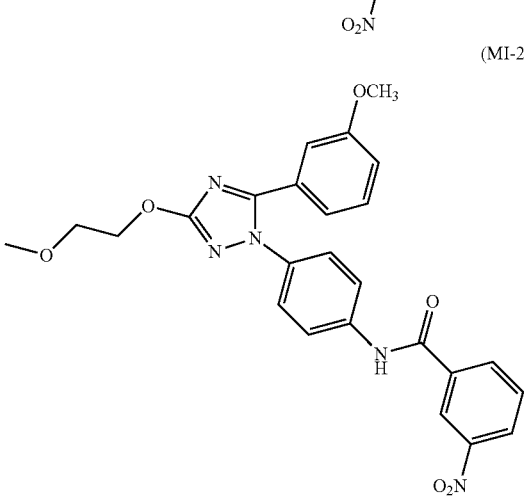
(MI-2A2)

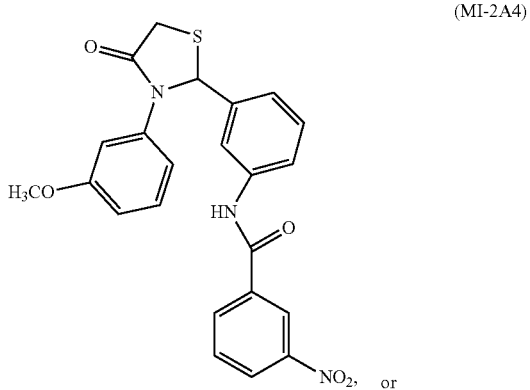
(MI-2A3)

(MI-2A4)

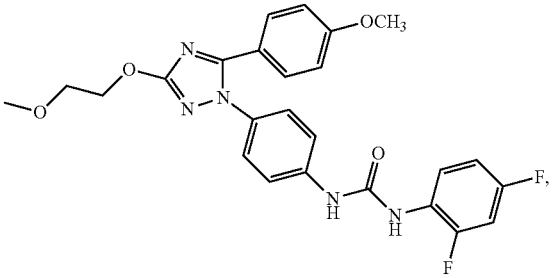
(MI-2A5)

or any salt, hydrate, tautomer, or stereoisomer thereof.

For example, in carrying out a method of the invention, the MALT1 can be disposed within a living animal, such as when the living animal is a human being afflicted with cancer, such as a diffuse large B-cell lymphoma.

Accordingly, the invention further provides, in various embodiments, a method of treating or preventing cancer comprising administering to a patient an effective dose of a compound of formula (I) as defined above; e.g., a compound of formula (I), formula (IA), formula (IB), or any of the specific examples of compounds that can be used.

For example, the cancer can be a lymphoma, such as a diffuse large B-cell lymphoma.

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

As used herein, "individual" (as in the subject of the treatment) or "patient" means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "disease" or "disorder" or "malcondition" are used interchangeably, and are used to refer to diseases or conditions wherein MALT1 plays a role in the biochemical mechanisms involved in the disease or malcondition or symptom(s) thereof such that a therapeutically beneficial effect can be achieved by acting on MALT1. "Acting on" MALT1, or "modulating" MALT1, can include binding to MALT1 and/or inhibiting the bioactivity of MALT1 and/or allosterically regulating the bioactivity of MALT1 in vivo.

The expression "effective amount", when used to describe therapy to an individual suffering from a disorder, refers to the amount of a compound of the invention that is effective to inhibit or otherwise act on MALT1 in the individual's tissues wherein MALT1 involved in the disorder is active, wherein such inhibition or other action occurs to an extent sufficient to produce a beneficial therapeutic effect.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

An "analog" of a chemical structure, as the term is used herein, refers to a chemical structure that preserves substantial similarity with the parent structure, although it may not be readily derived synthetically from the parent structure. A related chemical structure that is readily derived synthetically from a parent chemical structure is referred to as a "derivative."

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All single enantiomer, diastereomeric, and racemic forms of a structure are intended, unless a particular stereochemistry or isomeric form is specifically indicated. In several instances though an individual stereoisomer is described among specifically claimed compounds, the stereochemical designation does not imply that alternate isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

A "small molecule" refers to an organic compound, including an organometallic compound, of a molecular weight less than about 2 kDa, that is not a polynucleotide, a polypeptide, a polysaccharide, or a synthetic polymer composed of a plurality of repeating units.

As to any of the groups described herein, which contain one or more substituents, it is understood that such groups do not contain any substitution or substitution patterns which are sterically impractical and/or synthetically non-feasible. In addition, the compounds of this disclosed subject matter include all stereochemical isomers arising from the substitution of these compounds.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

When a group is recited, wherein the group can be present in more than a single orientation within a structure resulting in more than single molecular structure, e.g., a carboxamide group C(=O)NR, it is understood that the group can be present in any possible orientation, e.g., X—C(=O)N(R)—Y or X—N(R)C(=O)—Y, unless the context clearly limits the orientation of the group within the molecular structure.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated. For example, any hydrogen atom or set thereof in a molecule can be any of the isotopic forms of hydrogen, i.e., protium ($^1H$), deuterium ($^2H$), or tritium ($^3H$) in any combination. Similarly, any carbon atom or set thereof in a molecule can be any of the isotopic form of carbons, such as $^{11}C$, $^{12}C$, $^{13}C$, or $^{14}C$, or any nitrogen atom or set thereof in a molecule can be any of the isotopic forms of nitrogen, such as $^{13}N$, $^{14}N$, or $^{15}N$. A molecule can include any combination of isotopic forms in the component atoms making up the molecule, the isotopic form of every atom forming the molecule being independently selected. In a multi-molecular sample of a compound, not every individual molecule necessarily has the same isotopic composition. For example, a sample of a compound can include molecules containing various different isotopic compositions, such as in a tritium or $^{14}C$ radiolabeled sample where only some fraction of the set of molecules making up the macroscopic sample contains a radioactive atom. It is also understood that many elements that are not artificially isotopically enriched themselves are mixtures of naturally occurring isotopic forms, such as $^{14}N$ and $^{15}N$, $^{32}S$ and $^{34}S$, and so forth. A molecule as recited herein is defined as including isotopic forms of all its constituent elements at each position in the molecule. As is well known in the art, isotopically labeled compounds can be prepared by the usual methods of chemical synthesis, except substituting an isotopically labeled precursor molecule. The isotopes, radiolabeled or stable, can be obtained by any method known in the art, such as generation by neutron absorption of a precursor nuclide in a nuclear reactor, by cyclotron reactions, or by isotopic separation such as by mass spectrometry. The isotopic forms are incorporated into precursors as required for use in any particular synthetic route. For example, $^{14}C$ and $^{3}H$ can be prepared using neutrons generated in a nuclear reactor. Following nuclear transformation, $^{14}C$ and $^{3}H$ are incorporated into precursor molecules, followed by further elaboration as needed.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents $J^1$, $J^2$, and $J^3$ that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl; or wherein two R' groups bonded to a nitrogen atom or to adjacent nitrogen atoms can together with the nitrogen atom or atoms form a heterocyclyl, which can be mono- or independently multi-substituted with J.

In various embodiments, $J^1$, $J^2$, and $J^3$ can each independently be halo, nitro, cyano, OR, NR'$_2$, or R', or is C(O)OR', C(O)NR'$_2$, OC(O)OR', OC(O)NR'$_2$, N(R')C(O)OR', N(R')C(O)NR'$_2$ or thio/thiono analogs thereof. By "thio/thiono analogs thereof", with respect to a group containing an O, is meant that any or all O atoms in the group can be replaced by an S atom; e.g., for group C(O)OR, a "thio/thiono analog thereof" includes C(S)OR, C(O)SR, and C(S)SR; e.g., for group OC(O)NR$_2$, a "thio/thiono analog thereof" includes SC(O)NR$_2$, OC(S)NR$_2$, and SC(S)NR$_2$; and so forth.

In various embodiments, $J^1$, $J^2$, and $J^3$ is any of halo, (C1-C6)alkyl, (C1-C6)alkoxy, (C1-C6)haloalkyl, hydroxy(C1-C6)alkyl, alkoxy(C1-C6)alkyl, (C1-C6)alkanoyl, (C1-C6)alkanoyloxy, cyano, nitro, azido, R'$_2$N, R$_2$NC(O), R'$_2$NC(O)O, R'$_2$NC(O)NR, (C1-C6)alkenyl, (C1-C6)alkynyl, (C6-C10)aryl, (C6-C10)aryloxy, (C6-C10)aroyl, (C6-C10)aryl(C1-C6)alkyl, (C6-C10)aryl(C1-C6)alkoxy, (C6-C10)aryloxy(C1-C6)alkyl, (C6-C10)aryloxy(C1-C6)alkoxy, (3- to 9-membered)heterocyclyl, (3- to 9-membered)heterocyclyl(C1-C6)alkyl, (3- to 9-membered)heterocyclyl(C1-C6)alkoxy, (5- to 10-membered)heteroaryl, (5- to 10-membered)heteroaryl(C1-C6)alkyl, (5- to 10-membered)heteroaryl(C1-C6)alkoxy, or (5- to 10-membered)heteroaroyl. For example, R' independently at each occurrence can be H, (C1-C6)alkyl, or (C6-C10)aryl, wherein any alkyl or aryl group is substituted with 0-3 J.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR' is double-bonded to a carbon atom, the resulting C(=NR') group is termed an "imino" group. When a divalent substituent such as S is double-bonded to a carbon atom, the results C(=S) group is termed a "thiocarbonyl" or "thiono" group.

Alternatively, a divalent substituent such as O or S can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

Another divalent substituent is an alkylidene carbon, represented as C= and signifying that the carbon atom so indicated, which also bears two additional groups, is double bonded to a third group. For example, (CH$_3$)$_2$C= indicates an isopropylidene group bonded to another carbon or nitrogen atom.

C(O) and S(O)$_2$ groups can also be bound to one or two heteroatoms, such as nitrogen or oxygen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a "urea." When a C(O) is bonded to one oxygen and one nitrogen atom, the resulting group is termed a "carbamate" or "urethane." When a S(O)$_2$ group is bound to one carbon and one nitrogen atom, the resulting unit is termed a "sulfonamide." When a S(O)$_2$ group is bound to two nitrogen atoms, the resulting unit is termed a "sulfamide."

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

When a number of carbon atoms in a group, e.g., an alkyl, alkenyl, alkynyl, cycloalkyl, aryl, etc., is specified as a range, each individual integral number representing the number of carbon atoms is intended. For example, recitation of a ($C_1$-$C_4$)alkyl group indicates that the alkyl group can be any of methyl, ethyl, propyl, isopropyl, butyl, sec-butyl, isobutyl, or tert-butyl. It is understood that a specification of a number of carbon atoms must be an integer.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl.

Representative substituted alkyl groups can be substituted one or more times with any of the groups listed above, for example, amino, hydroxy, cyano, carboxy, nitro, thio, alkoxy, and halogen groups. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

The term "alkoxy" or "alkoxyl" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The term "amine" or "amino" includes primary, secondary, and tertiary amines having, e.g., the formula N(group)$_3$ wherein each group can independently be H or non-H, such as alkyl, aryl, and the like. Amines include but are not limited to R'—NH$_2$, for example, alkylamines, arylamines, alkylarylamines; R'$_2$NH wherein each R is independently selected, such as dialkylamines, diarylamines, aralkylamines, heterocyclylamines and the like; and R'$_3$N wherein each R is independently selected, such as trialkylamines, dialkylarylamines, alkyldiarylamines, triarylamines, and the like. The term "amine" also includes ammonium ions as used herein.

An "amino" group is a substituent of the form —NH$_2$, —NHR', —NR'$_2$, —NR'$_3^+$, wherein each R' is independently selected, and protonated forms of each, except for —NR'$_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion NH$_4^+$, but unless otherwise specified, it also includes any protonated or quaternarized forms of amines.

Thus, trimethylammonium hydrochloride and tetramethylammonium chloride are both ammonium ions, and amines, within the meaning herein.

The term "amide" (or "amido") includes C- and N-amide groups, i.e., —C(O)NR'$_2$, and —NR'C(O)R' groups, respectively. Amide groups therefore include but are not limited to primary carboxamide groups (—C(O)NH$_2$) and formamide groups (—NHC(O)H). A "carboxamido" group is a group of the formula C(O)NR'$_2$, wherein R' can be H, alkyl, aryl, etc.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The compounds described herein for use in a method of the invention can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials. All commercially available chemicals were obtained from Aldrich, Alfa Aesare, Wako, Acros, Fisher, Fluka, Maybridge or the like and were used without further purification, except where noted. Dry solvents are obtained, for example, by passing these through activated alumina columns.

The present invention further embraces isolated compounds of the invention. The expression "isolated compound" refers to a preparation of a compound of the invention, or a mixture of compounds the invention, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of the invention or a mixture of compounds of the invention, which contains the named compound or mixture of compounds of the invention in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

It will be understood that when compounds of the present invention contain one or more chiral centers, the compounds may exist in, and may be isolated as single and substantially pure enantiomeric or diastereomeric forms or as racemic mixtures. The present invention therefore includes any possible enantiomers, diastereomers, racemates or mixtures thereof of the compounds of the invention.

The compounds of the invention, or compounds used in practicing methods of the invention, may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present invention encompasses various stereoisomers of these compounds and mixtures thereof.

Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the invention, or compounds used in practicing methods of the invention, may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diastereomers of contemplated compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis,* Wiley-VCH: Weinheim, 2009.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated as having an (R) absolute configuration, and if the descending rank of the other groups proceeds counterclockwise, the molecule is designated as having an (S) absolute configuration. In the example in the Scheme below, the Cahn-Ingold-Prelog ranking is A>B>C>D. The lowest ranking atom, D is oriented away from the viewer.

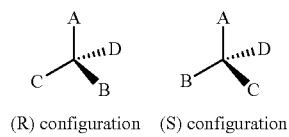

(R) configuration  (S) configuration

A carbon atom bearing the A-D atoms as shown above is known as a "chiral" carbon atom, and the position of such a carbon atom in a molecule is termed a "chiral center." Compounds of the invention may contain more than one chiral center, and the configuration at each chiral center is described in the same fashion.

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" or "isolated enantiomer" means a compound which has been substantially purified from the corresponding optical isomer(s) of the same formula. Preferably, the isolated isomer is at least about 80%, more preferably at least 90% enantiomerically pure, even more preferably at least 98% enantiomerically pure, most preferably at least about 99% enantiomerically pure, by weight. By "enantiomeric purity" is meant the percent of the predominant enantiomer in an enantiomeric mixture of optical isomers of a compound. A pure single enantiomer has an enantiomeric purity of 100%.

Isolated optical isomers may be purified from racemic mixtures by well-known chiral separation techniques. According to one such method, a racemic mixture of a compound of the invention, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Another well-known method of obtaining separate and substantially pure optical isomers is classic resolution, whereby a chiral racemic compound containing an ionized functional group, such as a protonated amine or carboxylate group, forms diastereomeric salts with an oppositely ionized chiral nonracemic additive. The resultant diastereomeric salt forms can then be separated by standard physical means, such as differential solubility, and then the chiral nonracemic additive may be either removed or exchanged with an alternate counter ion by standard chemical means, or alternatively the diastereomeric salt form may retained as a salt to be used as a therapeutic agent or as a precursor to a therapeutic agent.

Another aspect of an embodiment of the invention provides compositions of the compounds of the invention, alone or in combination with another medicament. As set forth herein, compounds of the invention include stereoisomers, tautomers, solvates, prodrugs, pharmaceutically acceptable salts and mixtures thereof. Compositions containing a compound of the invention can be prepared by conventional techniques, e.g. as described in Remington: *The Science and Practice of Pharmacy,* 19th Ed., 1995, or later versions thereof, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation can be tableted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that can be prepared by conventional tableting techniques can contain:

| Core: | |
|---|---|
| Active compound (as free compound or salt thereof) | 250 mg |
| Colloidal silicon dioxide (Aerosil ®) | 1.5 mg |
| Cellulose, microcryst. (Avicel ®) | 70 mg |
| Modified cellulose gum (Ac-Di-Sol ®) | 7.5 mg |
| Magnesium stearate | Ad. |
| Coating: | |
| HPMC approx. | 9 mg |
| *Mywacett 9-40 T | approx. 0.9 mg |

*Acylated monoglyceride used as plasticizer for film coating.

A typical capsule for oral administration contains compounds of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of compounds of the invention into a vial, aseptically freeze-drying and sealing. For use, the contents of the vial are mixed with 2 mL of sterile physiological saline, to produce an injectable preparation.

This disclosure provides pharmaceutical compositions comprising compounds as disclosed herein formulated together with a pharmaceutically acceptable carrier for use in practice of a method of the invention. In particular, the present disclosure provides for these methods pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

The compounds of the invention can be administered to a mammal, especially a human in need of such treatment, prevention, elimination, alleviation or amelioration of a malcondition. Such mammals include also animals, both domestic animals, e.g. household pets, farm animals, and non-domestic animals such as wildlife.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 µg to about 1250 mg, preferably from about 250 µg to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

It is within ordinary skill to evaluate any compound disclosed and claimed herein for effectiveness in inhibition of MALT1 and in the various cellular assays using the procedures described above or found in the scientific literature. Accordingly, the person of ordinary skill can prepare and evaluate any of the claimed compounds without undue experimentation.

Any compound found to be an effective inhibitor of MALT1 can likewise be tested in animal models and in human clinical studies using the skill and experience of the investigator to guide the selection of dosages and treatment regimens.

Biochemical Screening Identifies Low-Molecular-Weight Inhibitors of MALT1 Proteolytic Activity We reasoned that MALT1 small-molecule inhibitors might be useful chemical tools for studying MALT1 biology and treating MALT1 addicted tumors. However, full-length MALT1 and its paracaspase domain (amino acids 340-789) are naturally present in physiological solutions as a monomer, which has very low proteolytic activity. Caspases generally must homodimerize for maximal catalytic activity (Pop et al., 2006; Walker et al., 1994; Yin et al., 2006) and accordingly the recently reported structures of the paracaspase domain of MALT1 in complex with a peptide inhibitor are dimeric (Wiesmann et al., 2012; Yu et al., 2011). In order to generate catalytically active MALT1 for an effective assay to screen for inhibitors, we biochemically engineered a recombinant form of MALT1 (340-789) fused with a leucine zipper dimerization motif (LZ-MALT1), which promotes its dimerization and activation (FIG. 1A). We developed a MALT1 activity assay using the MALT1 substrate peptide LRSR linked to the fluorogen AMC (7-amino-4-methylcoumarin). Cleavage of the Ac-LRSR-AMC substrate by MALT1 resulted in release of AMC and a fluorescent signal.

The optimal conditions for high throughput screening were determined by systematic variation of the enzyme and the substrate in a two-dimensional grid. Fluorescence measurements were taken every 45 seconds for 60 minutes. The measurements were plotted as a function of time. Conditions with a linear relationship between fluorescence and time were considered appropriate for screening. Quality was assessed using Z'-factor, a coefficient reflective of the dynamic range of the assay and variance of the data (Zhang et al., 1999), calculated by the formula Z'-factor=1-3*($\sigma_p$+$\sigma_n$)/(|$\mu_p$-$\mu_n$|) where $\sigma_{p/n}$, standard deviation for positive and negative control; $\mu_{p/n}$, mean for positive and negative control. The Z'-factor for this screen was 0.738, which is within the optimal range 0.5-1 (Zhang et al., 1999). A total of 46,464 compounds were screened.

The compound library was obtained from Albany Molecular Research, Inc. (AMRI), of Albany, N.Y.

For MI-2, the ID number from AMRI is ALB-H03200218;
MI-2A1: CGX-01216062
MI-2A2: CGX-01216044
MI-2A3: CGX-01207032
MI-2A4: ALB-H09612295
MI-2A5: ALB-H01205459

Figure 1B:
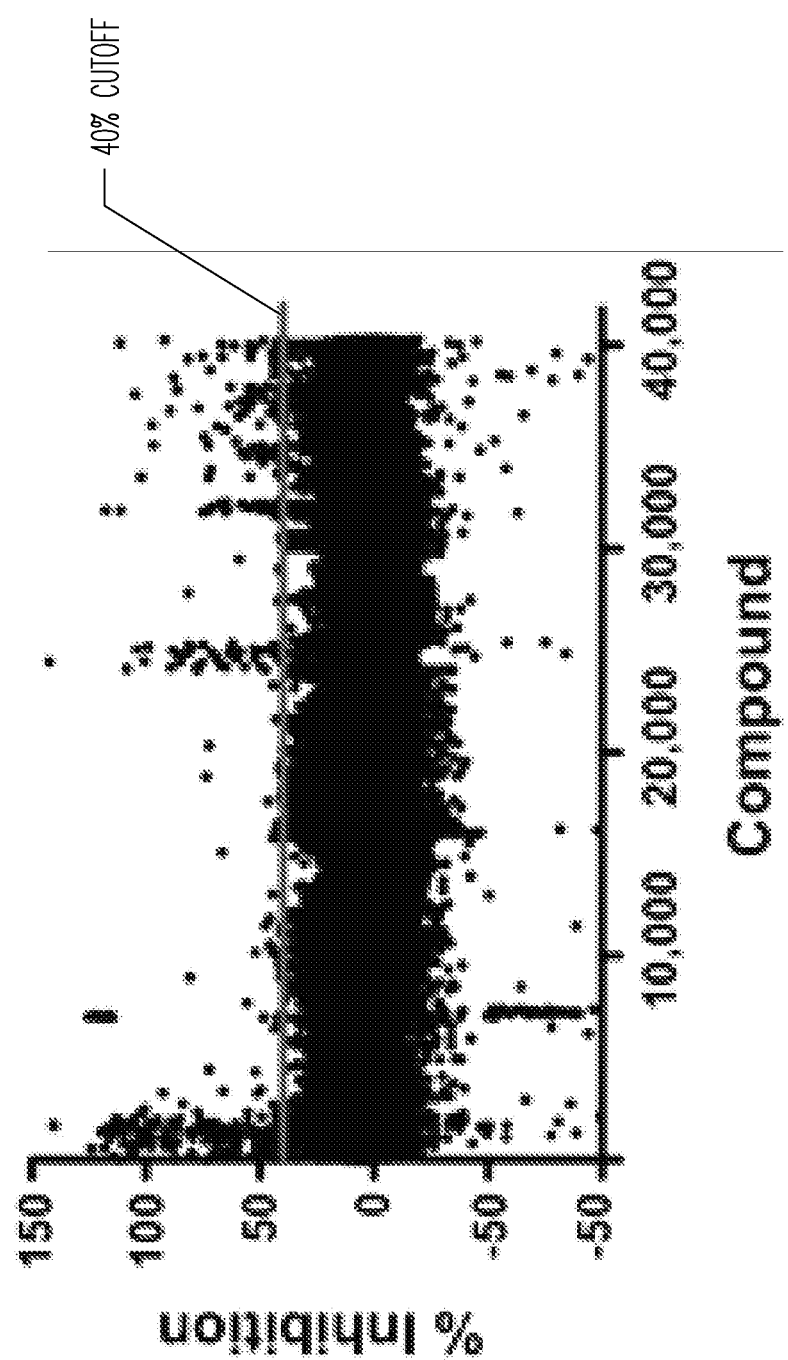
FIG. 1B is a graphic representation of the results by which 324 candidate compounds were selected from a compound library for validation in a concentration response assay using LZ-MALT1
Figure 1C:
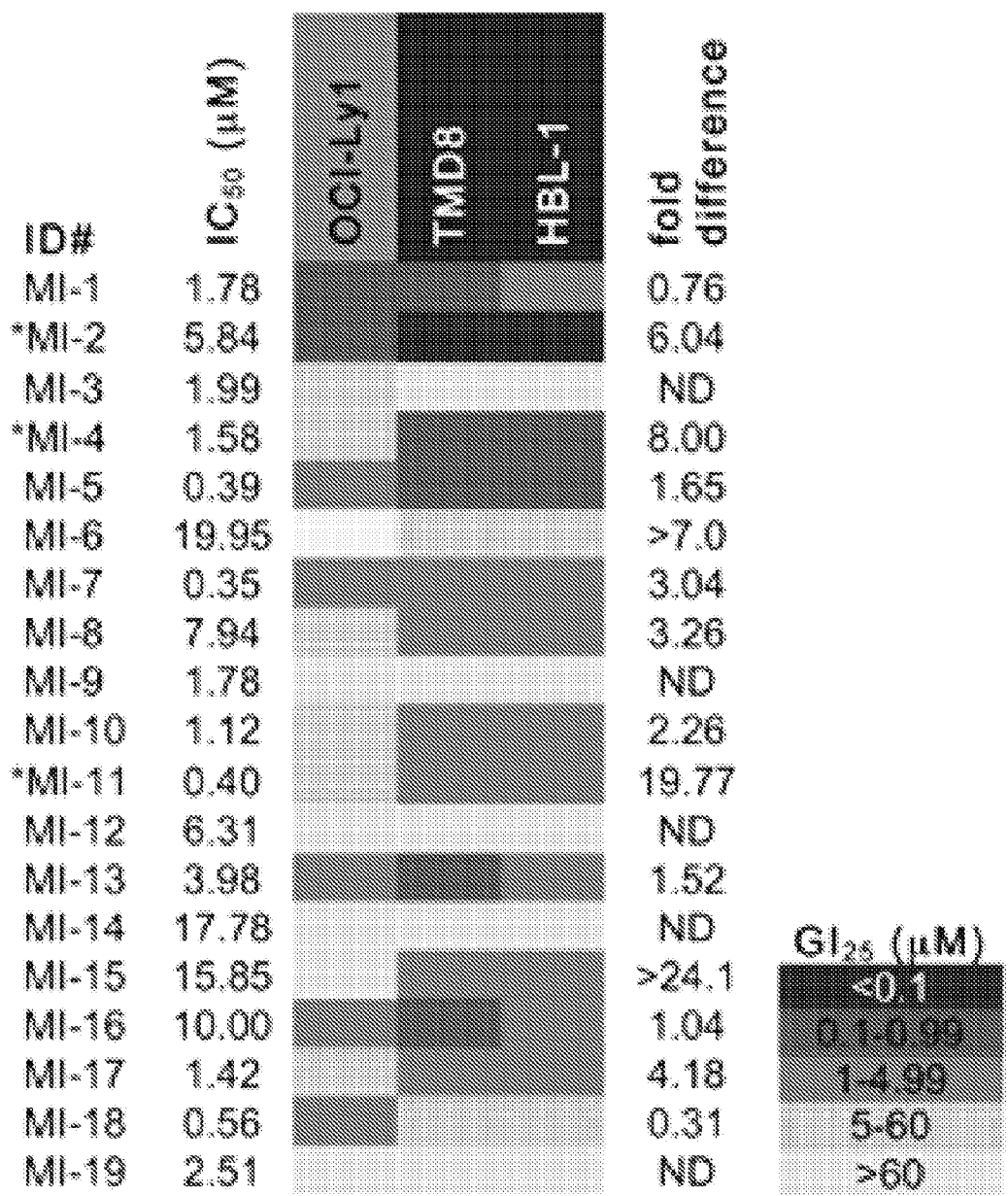
FIG. 1C is a graphic representation of the results by which nineteen compounds were selected for further validation based on their biochemical activity (IC$_{50}$<20 μM).

Using 40% inhibition as a threshold, 324 candidate compounds were selected for validation in a concentration response assay (FIG. 1B). Of these, nineteen compounds were selected for further validation based on their biochemical activity ($IC_{50}$<20 µM, FIG. 1C).

Candidate Inhibitors Selectively Suppress ABC-DLBCL Cell Lines and MALT1 Catalytic Activity.

MALT1 activity plays an important role in selectively maintaining proliferation of ABC-DLBCL cell lines (Ngo et al., 2006). Accordingly ABC and GCB-DLBCL cell lines present differential sensitivity to MALT1 cleavage inhibition by the peptide Z-VRPR-FMK (Ferch et al., 2009; Hailfinger et al., 2009; Rebeaud et al., 2008). To determine whether candidate small molecules display a similar profile two ABC-DLBCL cell lines, HBL-1 and TMD8, and one GCB-DLBCL cell line, OCI-Ly1, were exposed to increasing concentrations of the nineteen selected molecules. Cell proliferation was measured 48 hr after exposure to a single dose of compound using an ATP-based metabolic luminescent assay (summarized in FIG. 1C). Three compounds consistently induced significant selective dose-dependent suppression of ABC-DLBCL cells (MI-2, p<0.0001; MI-4, p=0.006 and MI-11, p<0.0001—Regression extra sum-of-squares F test). Hence these compounds were active in cells, selective for ABC-DLBLs and lack non-specific cellular toxicity. MI-6 and MI-15 also showed differential inhibition of ABC-DLBCL cells but did not reach statistical significance.

Figure 1D:
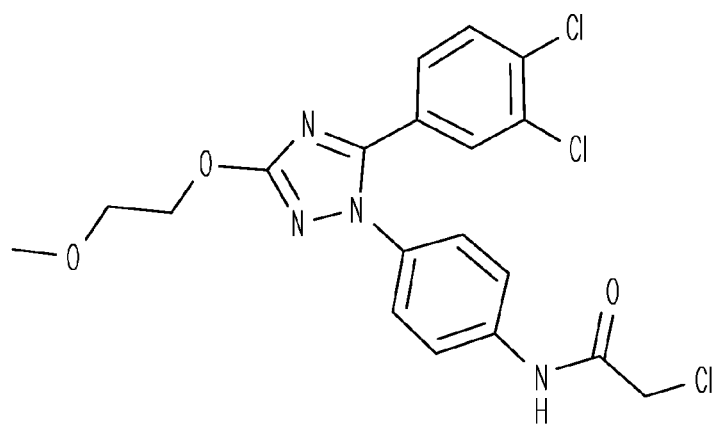
FIG. 1D shows the chemical structure of compound MI-2.
Figure 1E:
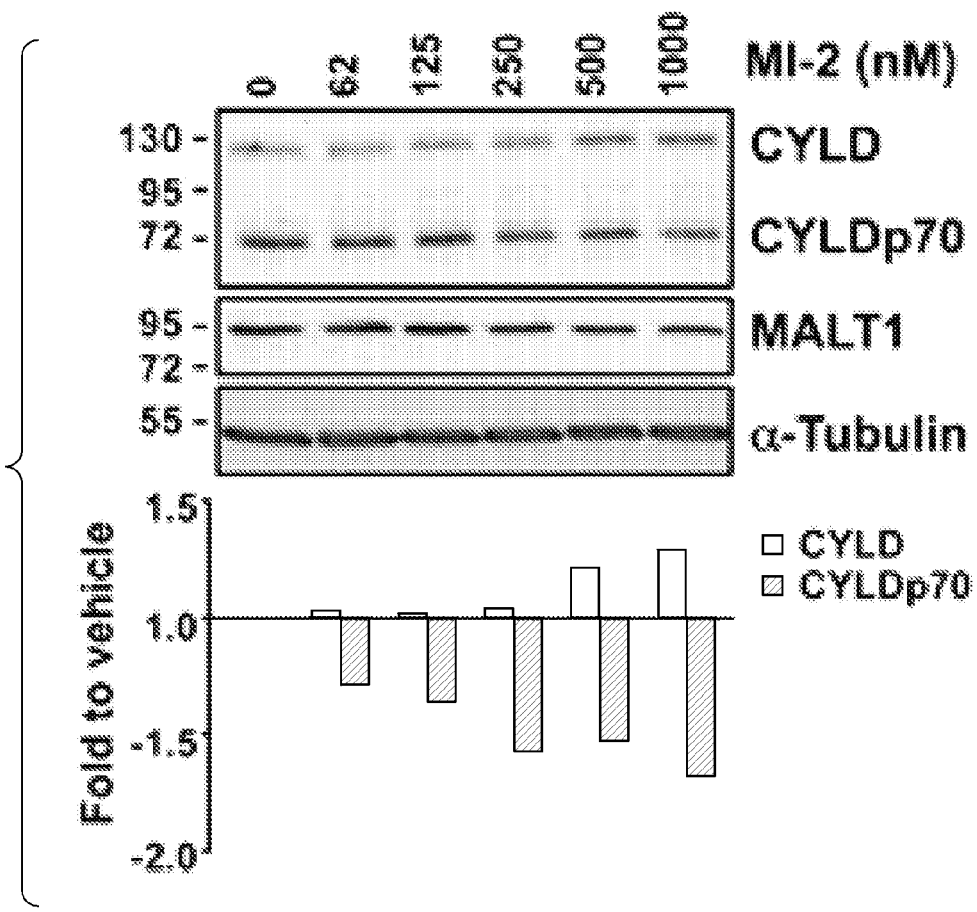
FIG. 1E shows a photograph of a Western blot of gel electrophoresis results demonstrating that MI-2 caused a dose-dependent decrease in MALT1-mediated cleavage, noted by an increase in the uncleaved CYLD protein and a decrease of the cleaved form of the protein as shown in the graphic representation of the Western blot data.

Compound MI-2 was the most potent in cell-based assays, with $GI_{25}$ concentrations in the high nanomolar range. MI-2 (FIG. 1D) was therefore next assayed for inhibition of MALT1-mediated substrate cleavage in lymphoma cells. HBL-1 cells were treated with increasing concentrations of MI-2 for 24 hr and cleavage of the MALT1 target protein CYLD measured by Western blotting and densitometry. MI-2 caused a dose-dependent decrease in MALT1-mediated cleavage, noted by an increase in the uncleaved CYLD protein and a decrease of the cleaved form of the protein (FIG. 1E). MI-2 was selective as a MALT1 paracaspase inhibitor since it displayed little activity against the structurally related caspase family members Caspase-3, -8 and -9. Moreover MI-2 did not inhibit Caspase-3/7 activity or apoptosis in cell-based assays at concentrations which suppress MALT1. Hence MI-2 is a potential lead compound as a therapeutic MALT1 inhibitor.

MI-2 Analogs Display MALT1 Inhibitory Activity

Figure 2A:
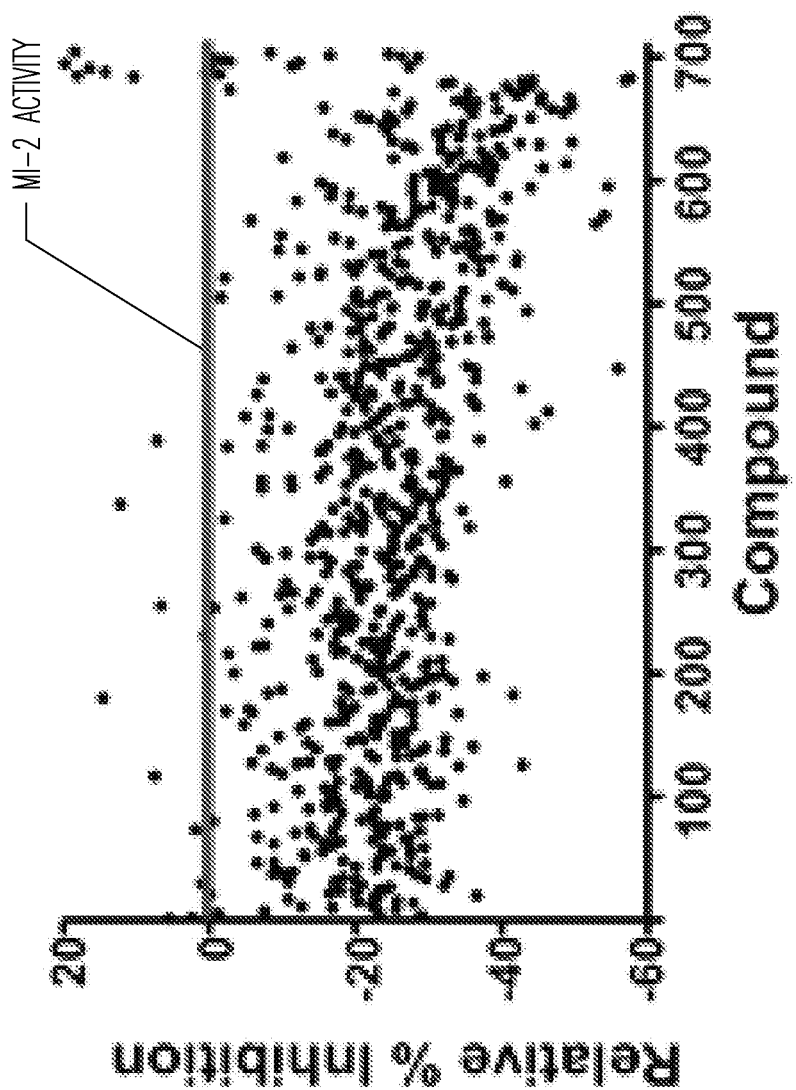
FIG. 2A is a graphic representation of the results by which nineteen analogs displaying equal or higher activity than MI-2 were selected.
Figure 2B:
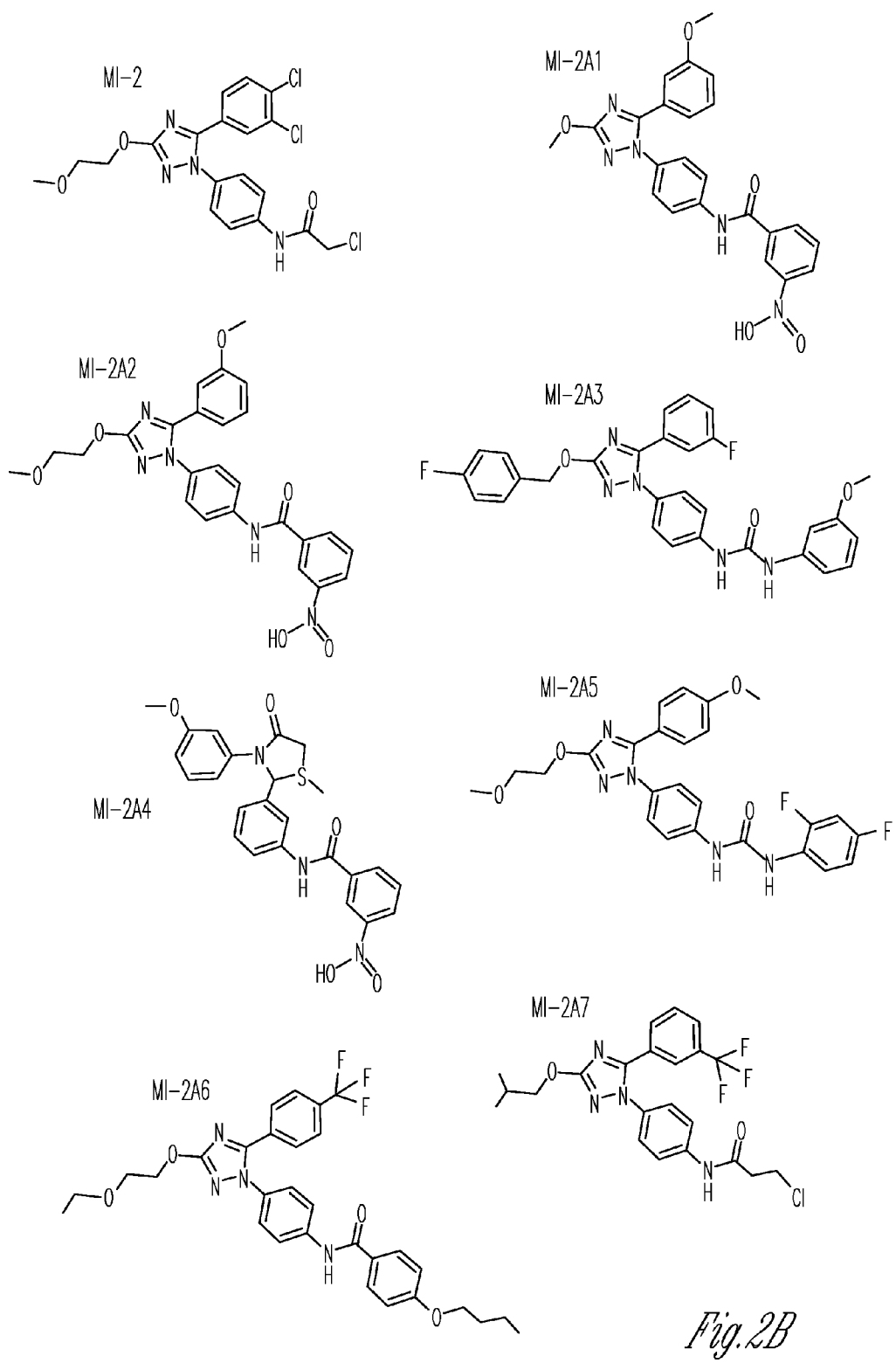
FIG. 2B shows the chemical structures of five analogs (MI-2A1 through MI-2A5) of MI-2 with biochemical IC$_{50}$s within a similar range as MI-2 selected for further characterization in cell proliferation assays and two analog compounds with no LZ-MALT1 inhibitory activity in vitro (MI-2A6 and MI-2A7) used as chemical controls that had no effect on cell proliferation over the same dose range.
Figure 2C:
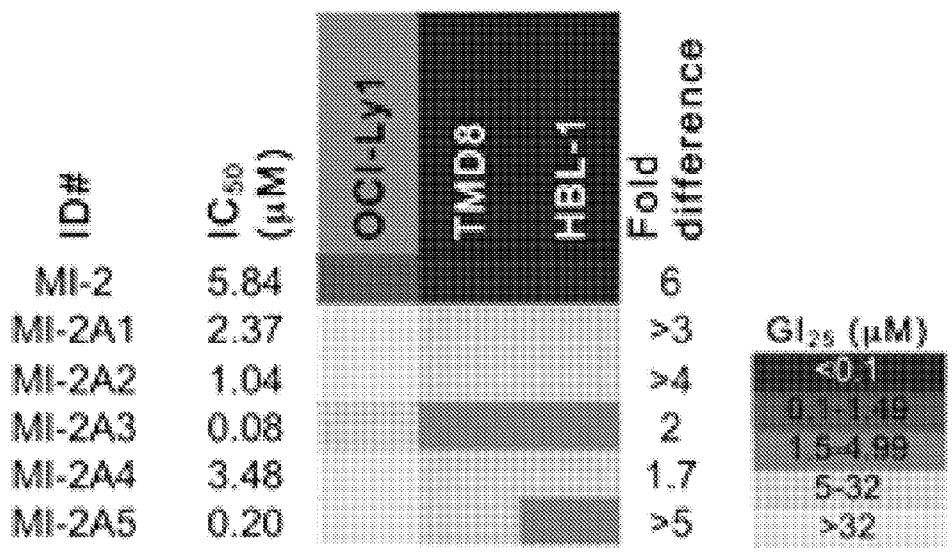
FIG. 2C is a graphic representation of the results of bioassays of compounds MI-2A1 through MI-2A5.
Figure 2D:
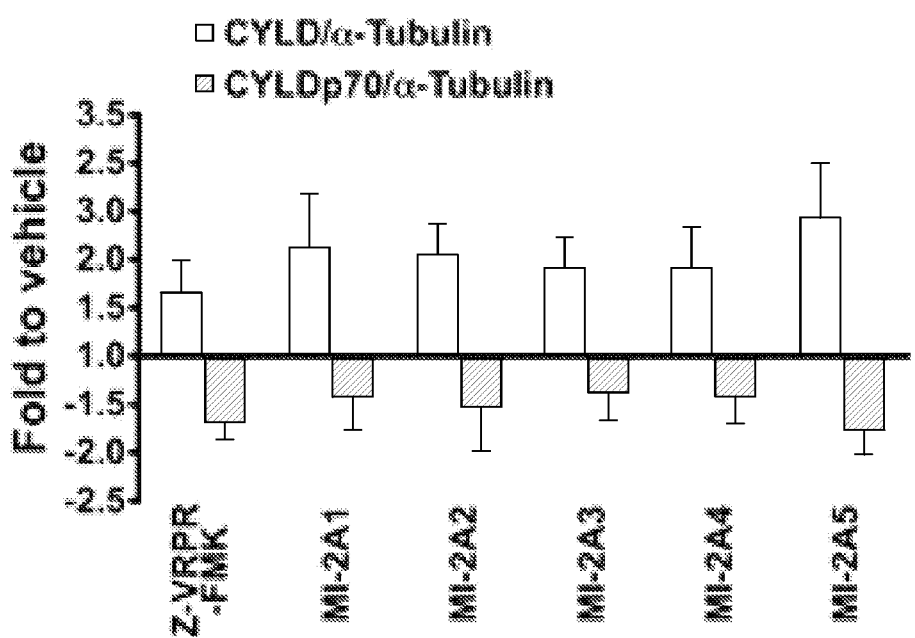
FIG. 2D is a graphic representation of the results obtained from the five compounds MI-2A1 through MI-2A5, administered at 5 μM for 8 hr, with respect to cleavage inhibition, with the Z-VRPR-FMK MALT1 blocking peptide (50 μM) used as positive control.

To establish whether compound MI-2 represented a potential scaffold for development of MALT1 inhibitors we compared MI-2 with other chemical compounds in silico to identify potential analogs. A total of 704 analog compounds from available libraries with similarity score ≥70% (Tanimoto similarity functions) were screened by LZ-MALT1 fluorescence assay. Nineteen analogs displaying equal or higher activity than MI-2 were selected (FIG. 2A). Five analogs with biochemical $IC_{50}$s within a similar range as MI-2 were selected for further characterization in cell proliferation assays (FIGS. 2B and 2C). All five analogs (MI-2A1-5) exhibited the same trend towards selective suppression of the ABC-DLBCL cell lines, with $GI_{25}$ concentrations in the micromolar range (FIG. 2C). Two analog compounds with no LZ-MALT1 inhibitory activity in vitro (MI-2A6-7) used as chemical controls had no effect on cell proliferation over the same dose range. The five active MI-2 analogs were assayed for inhibition of MALT1 cleavage of CYLD. All five compounds, administered at 5 µM for 8 hr showed cleavage inhibition similar to the Z-VRPR-FMK MALT1 blocking peptide (50 µM) used as positive control (FIG. 2D), although MI-2 itself remained the most potent compound. Collectively the conservation of MALT1 inhibitor activity in vitro and in cell-based assays among chemically related compounds points towards the suitability of MI-2 and its analogs as lead compound inhibitors of MALT1.

MI-2 Directly Binds and Irreversibly Inhibits MALT1

Figure 3A:
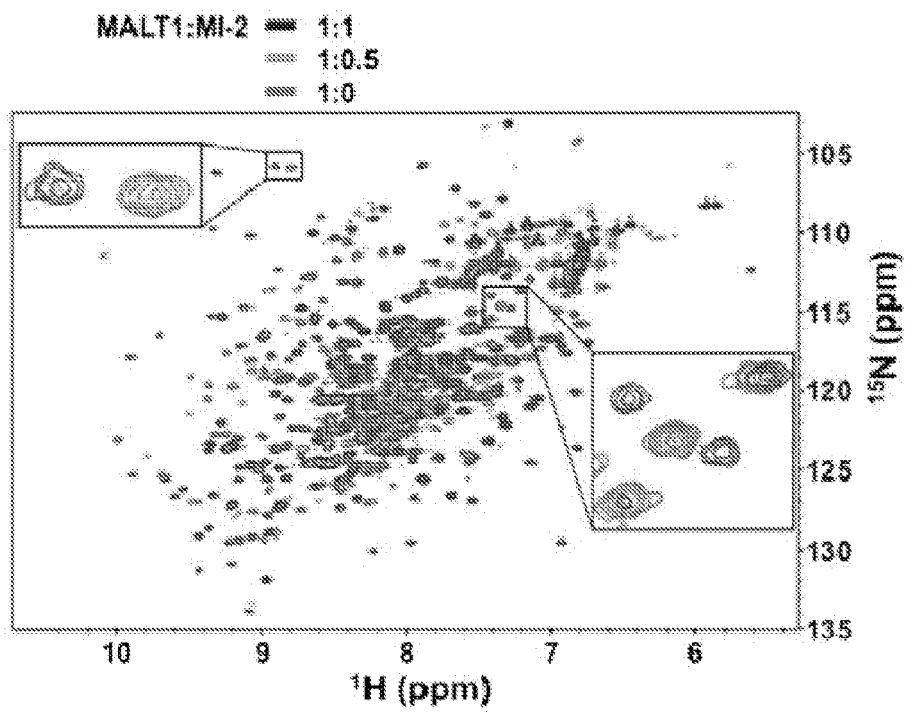
FIG. 3A is a Heteronuclear Single Quantum Coherence (HSQC) Nuclear Magnetic Resonance (NMR) spectrogram of MI-2 binding the paracaspase domain of MALT1 (residues 329-728).
Figure 3B:
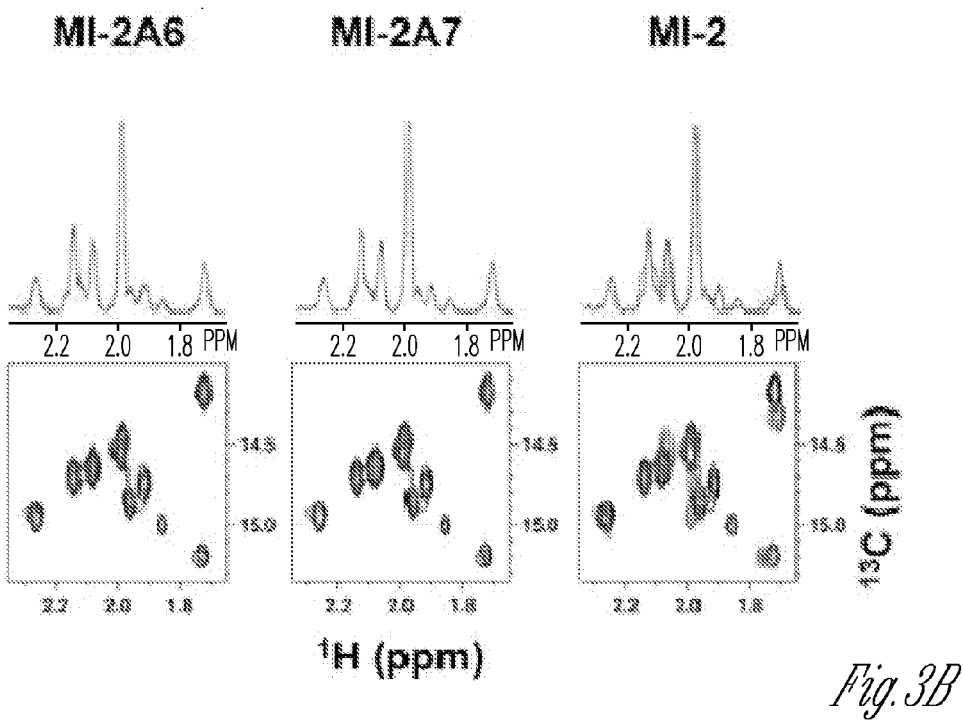
FIG. 3B shows NMR spectrograms evidencing the absence of binding of the paracaspase domain of MALT1 (residues 329-728). by the inactive analogs MI-2A6 and MI-2A7.

We next investigated whether MI-2 directly bound to MALT1 or indirectly affected MALT1 activity, for example through binding to the LZ region of the fusion protein. Heteronuclear Single Quantum Coherence (HSQC) Nuclear Magnetic Resonance (NMR) spectroscopy was used to characterize the binding of MI-2 to the paracaspase domain of MALT1 (residues 329-728). As MI-2 was titrated in, resonances corresponding to the unbound state of the MALT1 decreased in intensity, while another set of resonances corresponding to the MALT1-MI-2 complex gradually appeared (FIG. 3A). This pattern of chemical shift changes is characteristic of slow exchange on the NMR time scale and is indicative of a robust interaction between MALT1 and MI-2. In contrast, NMR spectroscopy studies showed no evidence of binding by the inactive analogs MI-2A6 and MI-2A7 (FIG. 3B).

Figure 3C:
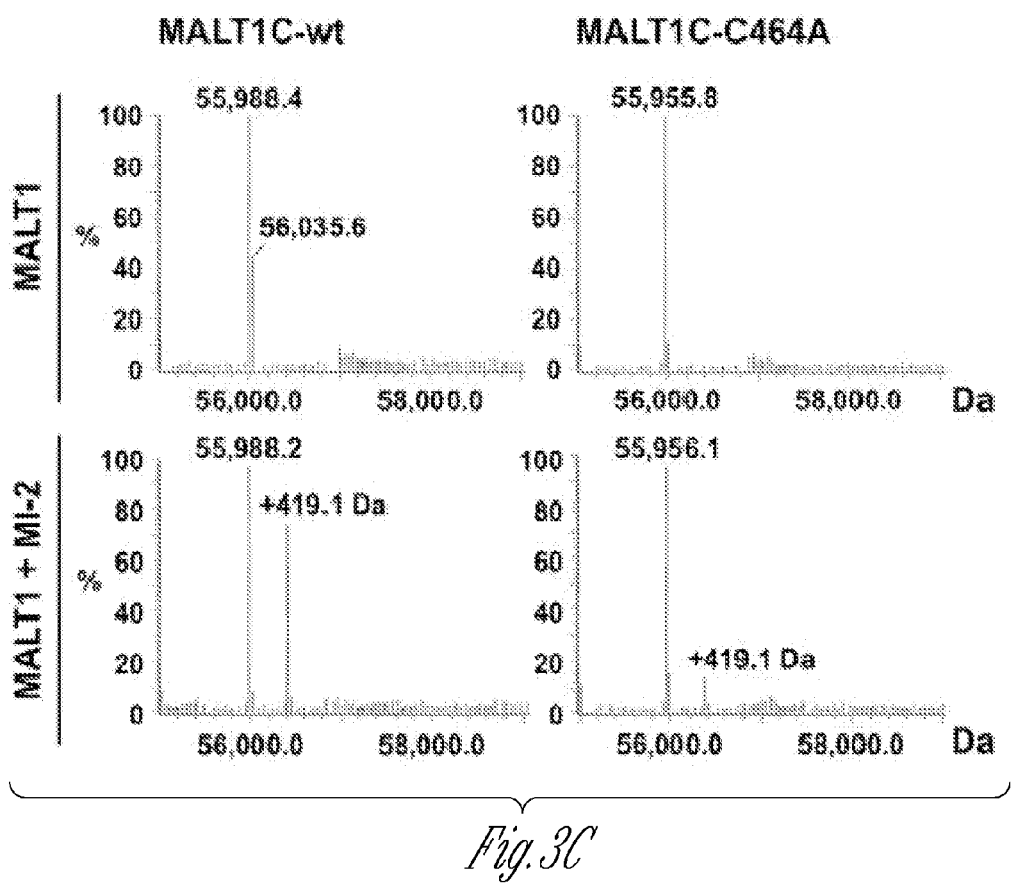
FIG. 3C shows mass spectometric data indicating that the MALT1 paracaspase domain (329-728) presented a major peak at 55,988.4 Da, and that upon incubation with compound MI-2, the major peak of MALT1 was shifted to 56,407.5 Da, an increase of 419.1 Da.
Figure 3D:
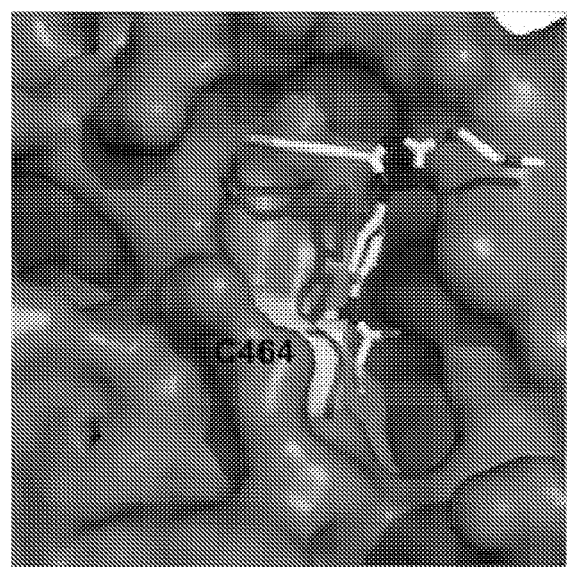
FIG. 3D shows an image of the potential mode of binding of MI-2 to the MALT1 paracaspase domain, as calculated by the molecular docking routine of molecular modeling program AutoDock 4.2, wherein MI-2 appears to bind the active site cleft with its chloromethyl group close to the active site C464 in the paracaspase domain.

Because MI-2 contains a reactive chloromethyl amide, we investigated whether MI-2 could modify MALT1 covalently using liquid chromatography-mass spectrometry (LC-MS). As shown in FIG. 3C, MALT1 paracaspase domain (329-728) presented a major peak at 55,988.4 Da. Upon incubation with compound MI-2, the major peak of MALT1 was shifted to 56,407.5 Da, an increase of 419.1 Da. This corresponds to addition of MI-2 minus the chloride group, indicating that MI-2 can bind covalently to MALT1 and potentially act as an irreversible inhibitor. Because the chloromethyl amide group is not conserved in the active MI-2 analogs (FIG. 2B), it is most likely the common chemical scaffold in the MI-2 series that provide specificity to MALT1. Notably, LC-MS performed with MI-2 and the MALT1 active site mutant C464A revealed markedly reduced covalent binding, suggesting that the active site C464 residue is the main target of modification by MI-2 (FIG. 3C). To further explore the potential mode of binding of MI-2 to the MALT1 paracaspase domain, we employed molecular docking using AutoDock 4.2 (Morris et al., 2009). The crystal structure of MALT1 (Wiesmann et al., 2012; Yu et al., 2011) was kept as a rigid body while allowing conformational flexibility of MI-2. The final results were ranked on the predicted binding free energy and the cluster size for each docking conformation. The top 5 poses were selected, all of which had similar docking scores with slight changes in their orientations. As shown for the first top hit, MI-2 appears to bind the active site cleft with its chloromethyl group close to the active site C464 in the paracaspase domain (FIG. 3D), consistent with a covalent bond formation between these two groups. Collectively the data suggest that MI-2 engages and irreversibly binds the MALT1 active site.

Figure 3E:
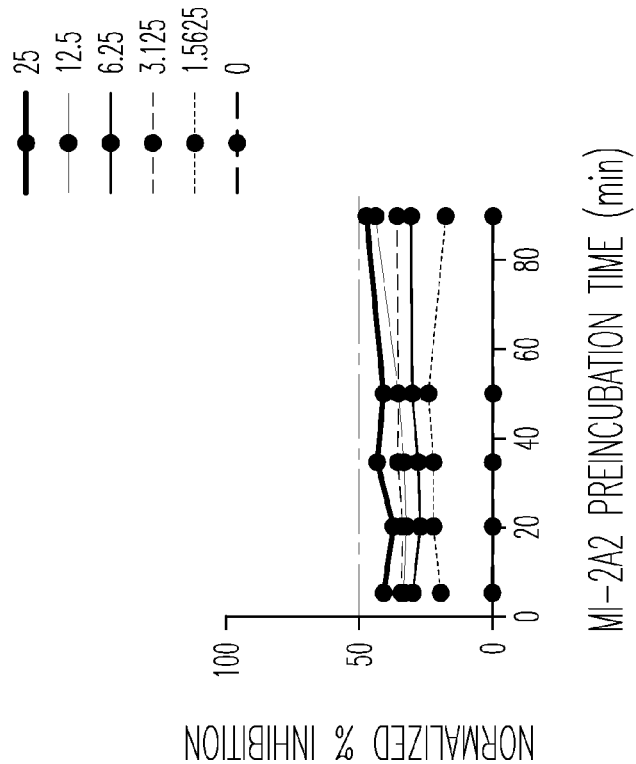
FIG. 3E shows the time course of enzymatic activity when LZ-MALT1 was pre-incubated with different concentrations of MI-2 (irreversible inhibition) versus MI-2A2 (reversible inhibition) for 5 to 80 minutes followed by addition of the fluorescent reporter substrate Ac-LRSR-AMC.
Figure 3E:
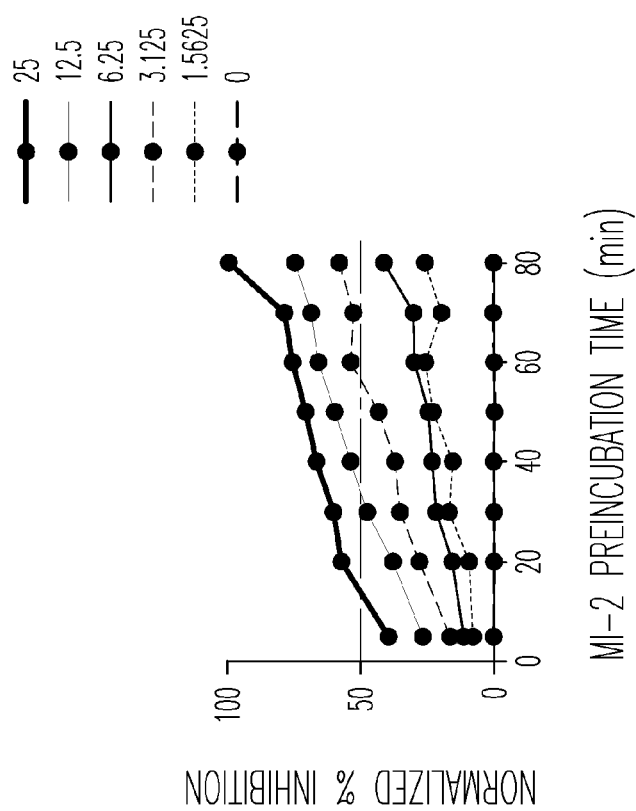

To examine whether MI-2 inhibition of MALT1 is consistent with irreversible binding kinetics LZ-MALT1 was pre-incubated with different concentrations of MI-2 for 5 to 80 minutes followed by addition of the substrate Ac-LRSR-AMC to determine enzymatic activity (FIG. 3E). Notably, the percent MALT1 inactivation increased with time, reaching plateaus near the end of the test, consistent with covalent and irreversible inhibition. Inhibition was concentration-dependent, with higher concentrations showing greater inactivation and faster rates of saturation. In contrast the active MI-2 analog MI-2A2, which does not have the chloromethyl amide group, showed no evidence of cumulative inhibition of MALT1, consistent with reversible inhibition. It should be noted that MI-2 reached close to 100% inhibition while MI-2A2 with lower $IC_{50}$ only reached ~50% inhibition (FIG. 3E). The irreversible kinetics might contribute to the more potent effects of MI-2 in cell-based assays vs. its analogs which lack the chloromethyl amide group and only bind reversibly, as has been noted in the case of peptidyl halomethyl ketone protease inhibitors (Powers et al., 2002).

MI-2 Inhibits MALT1 Functions in ABC-DLBCL Cell Lines

Figure 4A:
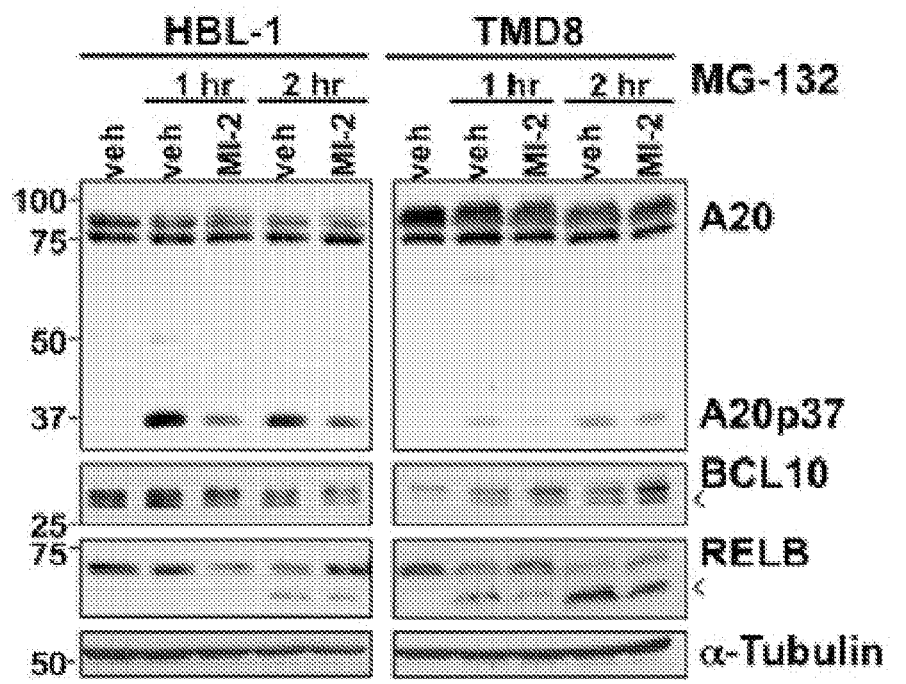
FIG. 4A shows a photograph of a Western blot of gel electrophoresis results using proteasome inhibitor MG-132 to facilitate visualization of cleavage products in HBL-1 and TMD8 cell lines exposed to either MI-2 (2 μM) or vehicle, for 30 minutes followed by 5 μM MG-132 for an additional one (lanes 2,3), or two hour (lanes 4, 5) in order to allow cleaved forms of MALT1 substrates to accumulate during exposure to MI-2.

Having confirmed MI-2 as a lead compound we next explored its effects on MALT1 signaling in ABC-DLBCL cells. We first examined the impact of MI-2 on cleavage of additional MALT1 substrates such as A20, BCL10 and RELB. As these proteins are directed to proteasomal degradation after cleavage (Coornaert et al., 2008; Hailfinger et al., 2011; Rebeaud et al., 2008), we used the proteasome inhibitor MG-132 to facilitate visualization of cleavage products (FIG. 4A). HBL-1 and TMD8 cell lines were exposed to either MI-2 (2 µM) or vehicle, for 30 minutes followed by 5 µM MG-132 for an additional one (lanes 2,3), or two hour (lanes 4, 5) in order to allow cleaved forms of MALT1 substrates to accumulate during exposure to MI-2. As expected MG-132 exposure revealed the accumulation of A20, BCL10 and RELB cleavage products due to the constitutive activity of MALT1 in these DLBCL cells. However exposure to MI-2 diminished the abundance of cleaved forms and/or increased the abundance of full-length proteins consistent with the loss of MALT1 enzymatic activity (FIG. 4A).

Figure 4B:
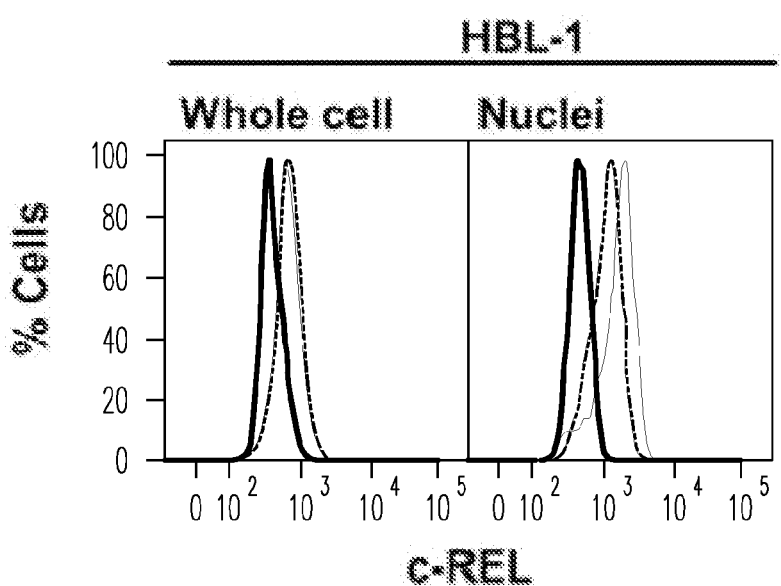
FIG. 4B shows results of experiments wherein HBL-1 cells were exposed to 200 nM MI-2, 50 μM Z-VRPR-FMK (positive control) or vehicle for 24 hr, followed by c-REL flow cytometry of whole cells or isolated nuclei. Both MI-2 and Z-VRPR-FMK reduced nuclear c-REL to a similar extent, without affecting whole cell levels of this protein.
Figure 4C:
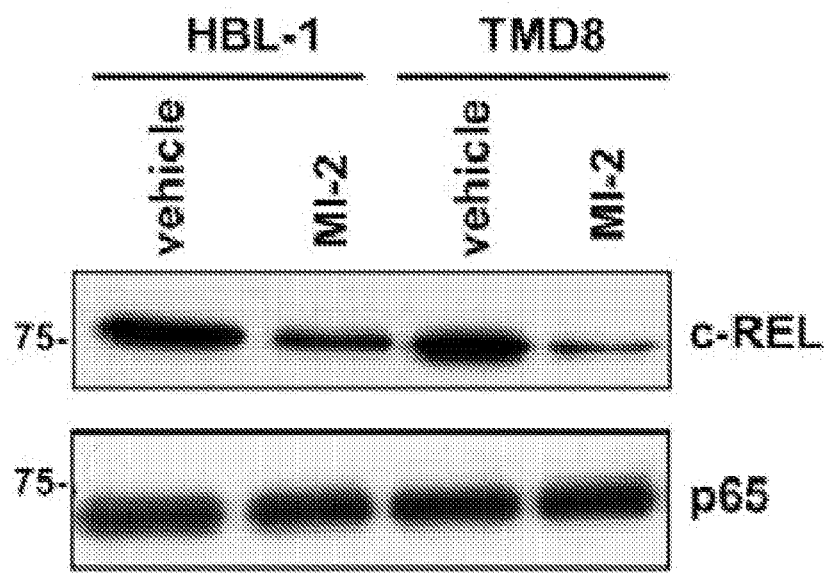
FIG. 4C shows Western blots for c-REL and p65 in nuclear extracts of HBL-1 and TMD8 cells treated for 24 hr with GI$_{50}$ concentrations of MI-2 (200 nM for HBL-1 and 500 nM for TMD8). In both cell lines exposure to MI-2 caused a clear reduction of nuclear c-REL while it did not affect p65 levels.

MALT1 mediates c-REL translocation to the nucleus following BCR stimulation (Ferch et al., 2007). Therefore HBL-1 cells were exposed to 200 nM MI-2, 50 µM Z-VRPR-FMK (positive control) or vehicle for 24 hr, followed by c-REL flow cytometry of whole cells or isolated nuclei. Both MI-2 and Z-VRPR-FMK reduced nuclear c-REL to a similar extent, without affecting whole cell levels of this protein (FIG. 4B). To further confirm this result, we also performed Western blots for c-REL and p65 in nuclear extracts of HBL-1 and TMD8 cells treated for 24 hr with $GI_{50}$ concentrations of MI-2 (200 nM for HBL-1 and 500 nM for TMD8). In both cell lines exposure to MI-2 caused a clear reduction of nuclear c-REL while it did not affect p65 levels (FIG. 4C). This selectivity towards c-REL had also been previously shown in MALT1 knockout mice and after MALT1 cleavage inhibition by the MALT1 blocking peptide Z-VRPR-FMK (Ferch et al., 2009; Ferch et al., 2007; Hailfinger et al., 2011).

Figure 4D:
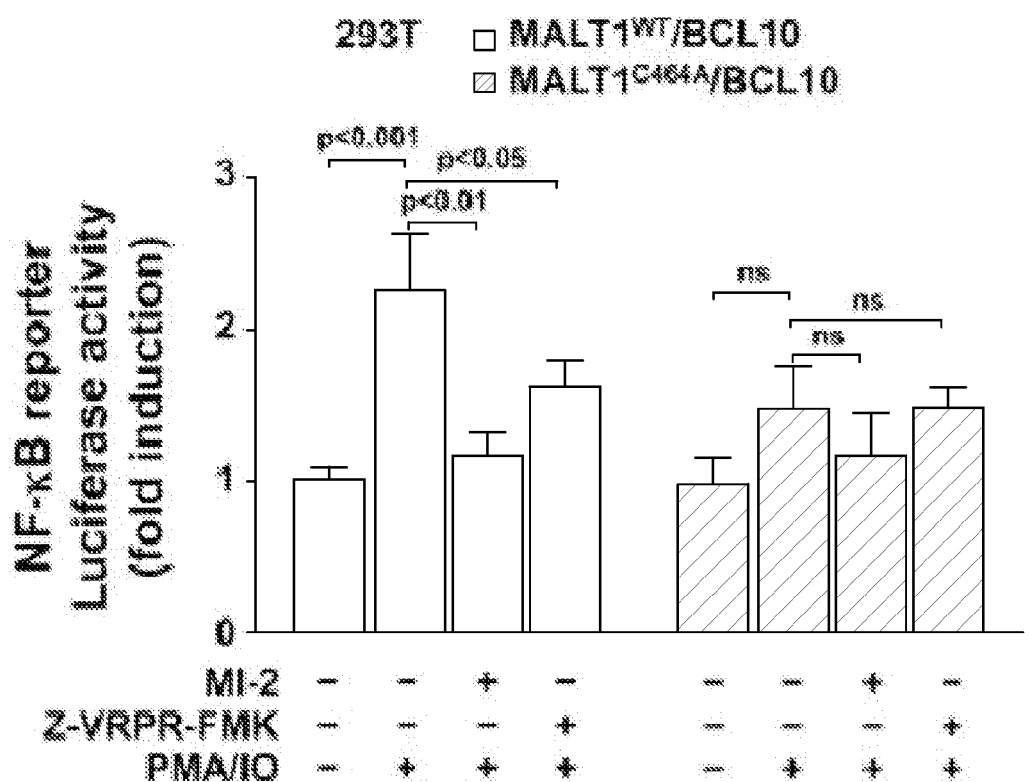
FIG. 4D is a graphical representation of data on the effect of MI-2 on attenuating NF-κB activation induced by PMA/ionomycin, wherein 293T cells were transfected with the NF-κB reporter vector (NF-κB)$_5$-luc2CP-pGL4 and TK-pRL control together with plasmids expressing BCL10 and either MALT1$^{WT}$ or MALT1$^{C464A}$ (inactive mutant).

Antigen receptor-mediated NF-κB signaling partly depends on MALT1 activity (Ruefli-Brasse et al., 2003; Ruland et al., 2003). Hence we tested the effect of MI-2 on attenuating NF-κB activation induced by PMA/ionomycin, which mimics BCR activation and activates MALT1-dependent cleavage (Coornaert et al., 2008; Rebeaud et al., 2008). First, 293T cells were transfected with the NF-κB reporter vector (NF-κB)$_5$-luc2CP-pGL4 (harboring 5 copies of the NF-κB consensus response element and a destabilized Firefly luciferase) and TK-pRL control together with plasmids expressing BCL10 and either MALT1$_1^{WT}$ or MALT1$^{C464A}$ (inactive mutant). Exposure to PMA/ionomycin significantly increased luciferase activity in 293T cells when MALT1$^{WT}$ was transfected (p<0.001; ANOVA and Bonferroni post-test), but not with the mutant MALT1$^{C464A}$. Pretreatment with MI-2 significantly inhibited NF-κB induction by PMA/ionomycin stimulation (p<0.01; ANOVA and Bonferroni post-test) similarly to Z-VRPR-FMK (p<0.05), while it did not significantly affect that of MALT1$^{C464A}$ (FIG. 4D). HBL-1 cells are reported to exhibit chronic active B-cell receptor signaling with consequent NF-κB activation (Davis et al., 2010). HBL-1 was transfected with the reporter construct (NF-κB)$_5$-luc2CP-pGL4 and TK-pRL control.

Figure 4E:
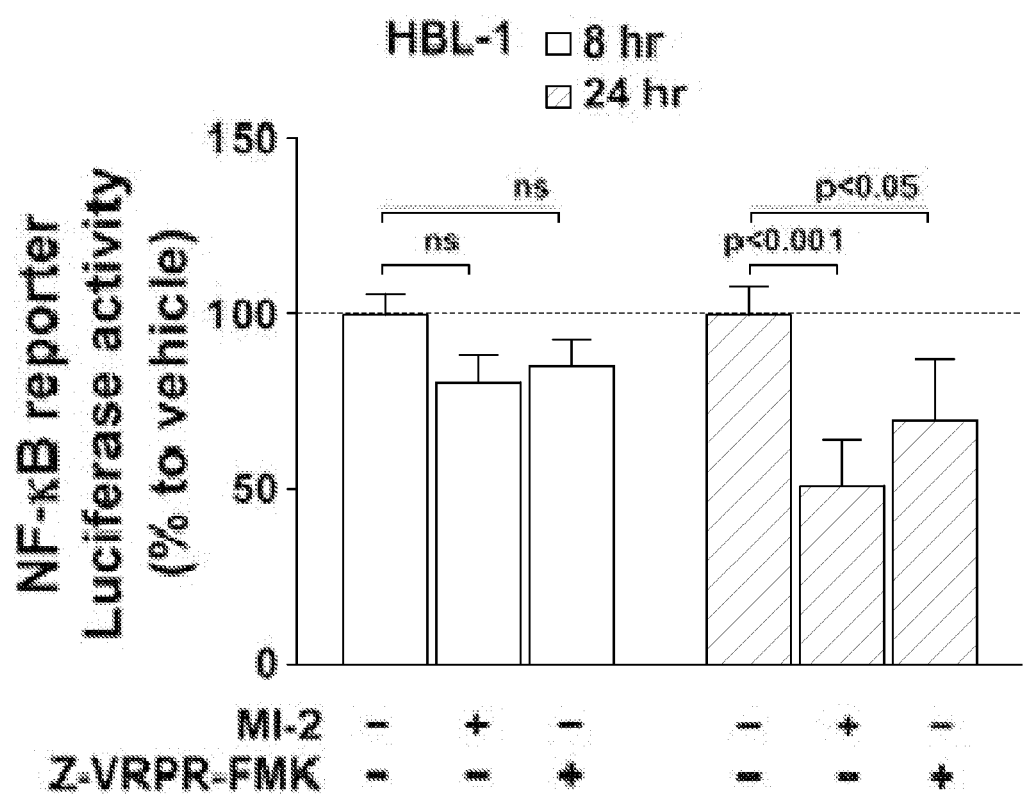
FIG. 4E is a graphical representation of data on the effect of MI-2 on attenuating NF-κB activation induced by PMA/ionomycin, wherein HBL-1 cells were transfected with the NF-κB reporter vector (NF-κB)$_5$-luc2CP-pGL4 and TK-pRL control.

Treatment with MI-2 promoted a 20% and 50% reduction in NF-κB reporter activity at 8 and 24 hr, respectively. A similar result was observed for Z-VRPR-FMK 50 µM (FIG. 4E). This reduction in NF-κB reporter activity was significant at 24 hr for MI-2 (p<0.001, ANOVA and Bonferroni post-test) and the blocking peptide Z-VRPR-FMK (p<0.05).

Figure 4F:
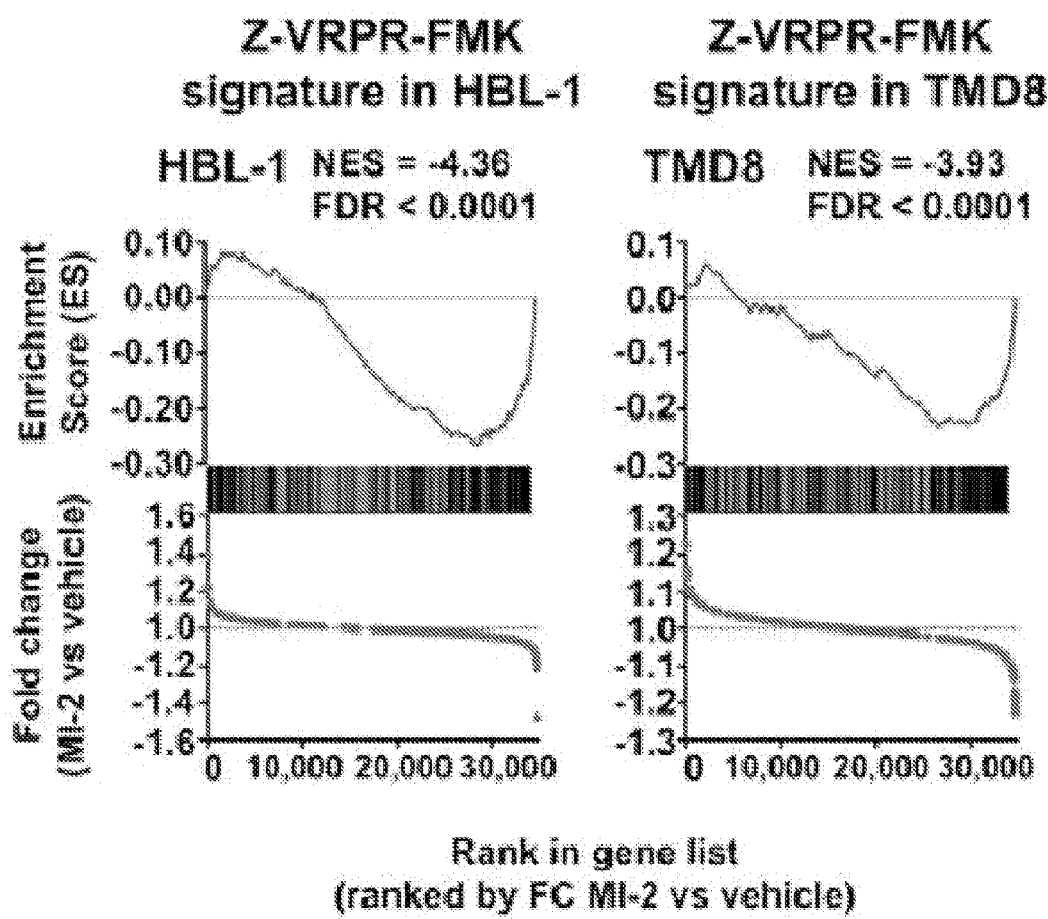
FIG. 4F shows results of gene set enrichment analysis (GSEA) of the Z-VRPR-FMK signature against the differential expression of all genes pre-ranked by fold change between MI-2 and vehicle-treated cells for each cell line. The Z-VRPR-FMK signature was significantly enriched among genes downregulated after MI-2-treatment for both cell lines (HBL-1: FDR<0.0001; and TMD8: FDR<0.0001).

The impact of MI-2 on NF-κB signaling was further characterized by gene expression profiling. For these experiments the HBL-1 and TMD8 cell lines were treated with $GI_{50}$ concentrations of MI-2 (HBL-1, 200 nM; TMD8, 500 nM) or 50 µM Z-VRPR-FMK for 8 hr, and RNA was extracted for gene expression studies using oligonucleotide microarrays. Z-VRPR-FMK was previously shown to attenuate the NF-κB signature in ABC-DLBCL cell lines (Hailfinger et al., 2009). MI-2 would be expected to exhibit a similar profile. For this study we assigned Z-VRPR-FMK signatures by capturing the top 200 downregulated genes by Z-VRPR-FMK treatment compared to vehicle for each cell line. We next performed gene set enrichment analysis (GSEA) of this Z-VRPR-FMK signature against the differential expression of all genes pre-ranked by fold change between MI-2 and vehicle-treated cells for each cell line. The Z-VRPR-FMK signature was significantly enriched among genes downregulated after MI-2-treatment for both cell lines (HBL-1: FDR<0.0001; and TMD8: FDR<0.0001, FIG. 4F). GSEA was next performed using two independent ABC-DLBCL NF-κB gene expression signatures derived from either OCI-Ly3 and OCI-Ly10 or HBL-1 cell lines. We observed significant enrichment of these NF-κB gene sets among genes downregulated after MI-2-treatment in both cell lines (NF-κB OCI-Ly3/OCI-Ly10, HBL-1: FDR=0.015 and TMD8: FDR<0.0001) and (NF-κB HBL-1, HBL-1: FDR=0.051 and TMD8: FDR<0.0001). Collectively these data suggest that MI-2 suppresses NF-κB activity induced by MALT1, similar to the effect observed with Z-VRPR-FMK.

MI-2 Selectively Suppresses MALT1-Dependent DLBCL Cell Lines

To further explore the spectrum of MI-2-mediated MALT1 inhibition effects we turned to a larger panel of six ABC-DLBCL and two GCB-DLBCL cell lines. Genetic features affecting B cell receptor and NF-κB pathway in these cell lines are summarized in Table 1.

TABLE 1

ABC-DLBCL NF-κB activating mutations present in the cell lines used in this study.

| Cell line | CD79A/B (Davis et al., 2010) | MYD88 (Ngo et al., 2011) | CARD11 (Lenz et al., 2008) | TNFAIP3 (Compagno et al., 2009) | TAK1 (Compagno et al., 2009) |
|---|---|---|---|---|---|
| HBL-1 | Y196F$^{HET}$ | L265P | wt | wt | wt |
| TMD8 | Y196H$^{HET}$ | L265P | wt | wt | wt |
| OCI-Ly3 | wt | L265P | L251P | Hem del | wt |
| OCI-Ly10 | Δ4275-4316$^{HET}$ | L265P | wt | Hem del | wt |
| U2932 | wt | wt | wt | Hem del | S417A |
| HLY-1 | wt | S219C | E634Q | Hom del | wt |
| OCI-Ly7 | wt | wt | wt | wt | wt |
| OCI-Ly1 | wt | wt | wt | wt | wt |

Endogenous MALT1 activity was evaluated by Western blotting for A20, BCL10 and CYLD; and NF-κB activation, by phospho-IκB-α and total IκB-α. Dependence on MALT1 proteolytic activity for proliferation was tested by 50 µM Z-VRPR-FMK treatment for 48 hr. As expected the two GCB-DLBCL cell lines (OCI-Ly7 and OCI-Ly1) did not display evidence of MALT1 or NF-κB signaling and did not respond to Z-VRPR-FMK. The U2932 and HLY1 ABC- DLBCL cell lines harbor mutations in TAK1 and A20, which activate NF-κB signaling downstream of MALT1. Hence these two cell lines displayed relatively little response to Z-VRPR-FMK. In contrast the ABC-DLBCL cells HBL-1, TMD8, OCI-Ly3 and OCI-Ly10 displayed evidence of MALT1 activity and inhibition of proliferation by Z-VRPR-FMK, indicating that these four cell lines are MALT1 dependent.

Figure 5A:
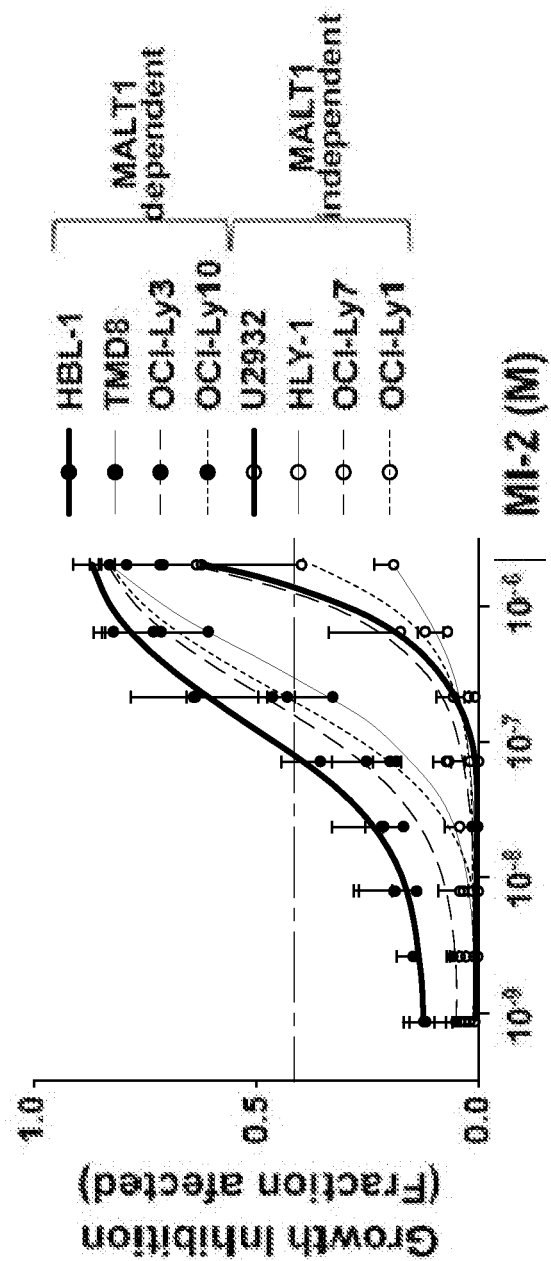
FIG. 5A shows a graphical representation of results from experiments wherein eight cell lines were exposed to increasing concentrations of MI-2 (single dose) and cell proliferation measured at 48 hr using an ATP-based metabolic luminescent assay.
Figure 5B:
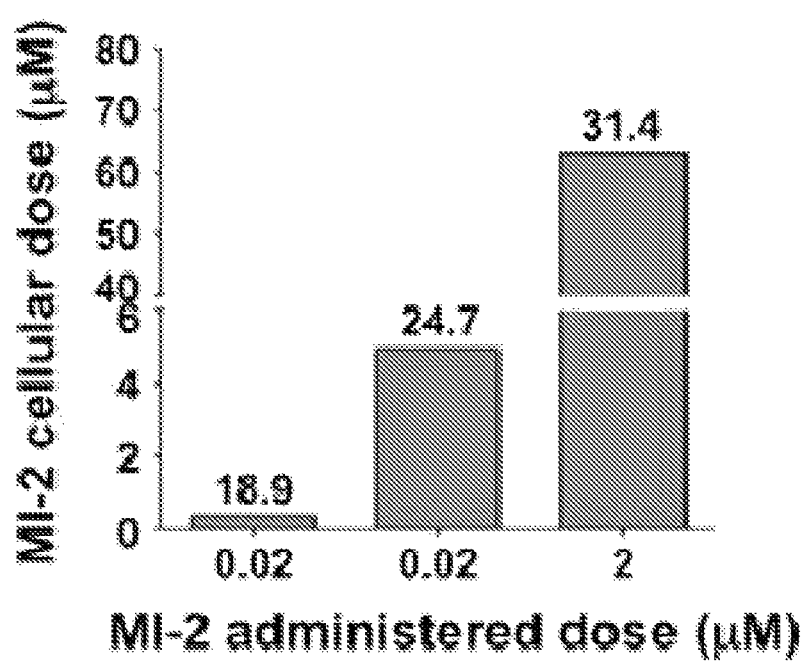
FIG. 5B is a graphical representation of results of MI-2 intracellular concentration experiments where HBL-1 cells were exposed to 0.02, 0.2 or 2 µM MI-2 for 2 hr, washed three times, and MI-2 measured by LC-MS.

All eight cell lines were exposed to increasing concentrations of MI-2 (single dose) and cell proliferation measured at 48 hr using an ATP-based metabolic luminescent assay (FIG. 5A). Growth inhibition by MI-2 was selective for MALT1 dependent cell lines while the ABC-DLBCL MALT1 independent cell lines, U2932 and HLY-1, and the two GCB-DLBCL cell lines were resistant. The $GI_{50}$ for MI-2 in HBL-1, TMD8, OCI-Ly3 and OCI-Ly10 cells was 0.2, 0.5, 0.4, and 0.4 μM, respectively, which is lower than its $IC_{50}$ in vitro (FIG. 1). This is likely explained by the irreversible binding of MI-2 to MALT1 as shown in FIG. 3 but could also be due to intracellular accumulation of the compound. Indeed we observed an 18 to 30-fold increase in MI-2 intracellular concentration in experiments where HBL-1 cells were exposed to 0.02, 0.2 or 2 μM MI-2 for 2 hr, washed three times, and MI-2 measured by LC-MS (FIG. 5B). The intracellular concentration in the 0.2 μM MI-2 treated cells was 5 μM, similar to the calculated in vitro $IC_{50}$ (FIG. 5B). To determine the kinetics of accumulation of free drug we measured the intracellular concentration of MI-2 at the $GI_{50}$ concentration of 0.2 μM at 30 min, 2, 6, 12, 24 and 48 hr. By 12 hr there was virtually no detectable free MI-2 within the cells. However, after exposure of HBL-1 cells to increasing concentrations of a single dose of MI-2, recovery of cells only started to become evident after 48 hr (of the 0.2 μM dose level). These data suggest that the potent biological effects of MI-2 are due at least in part to its irreversible binding to MALT1 aided by its tendency to concentrate in cells.

Figure 5D:
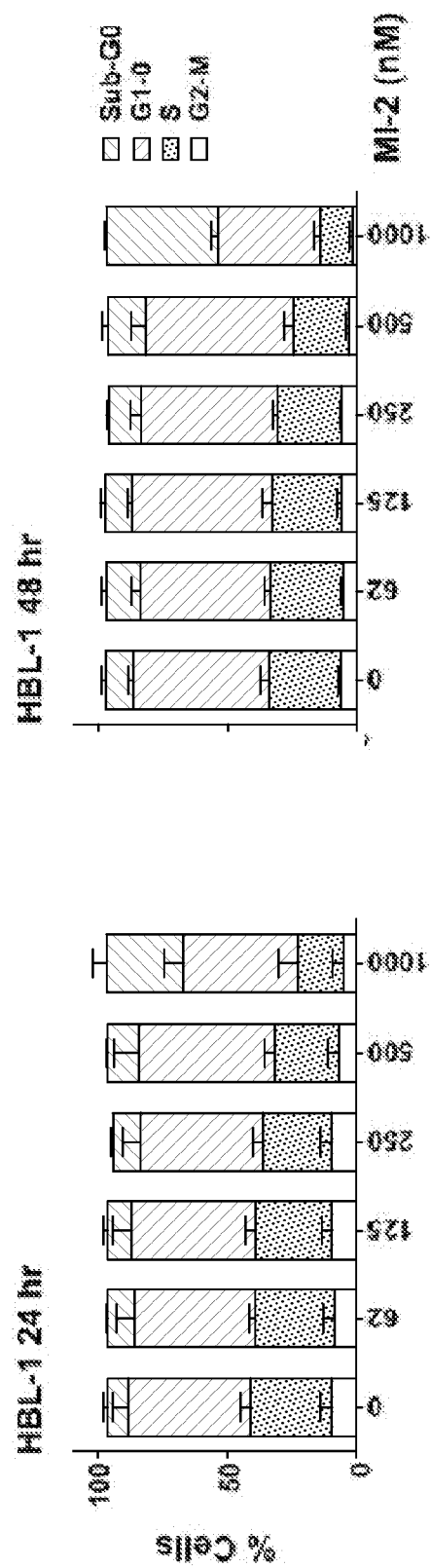
FIG. 5D shows graphical representation of results of experiments wherein, using BrdU incorporation—DAPI staining and flow cytometry to assess cell cycle, it was evident that MI-2 induced a dose-dependent decrease in S phase, with reciprocal increment in the proportion of cells in G1-0 and Sub-G0.
Figure 5E:
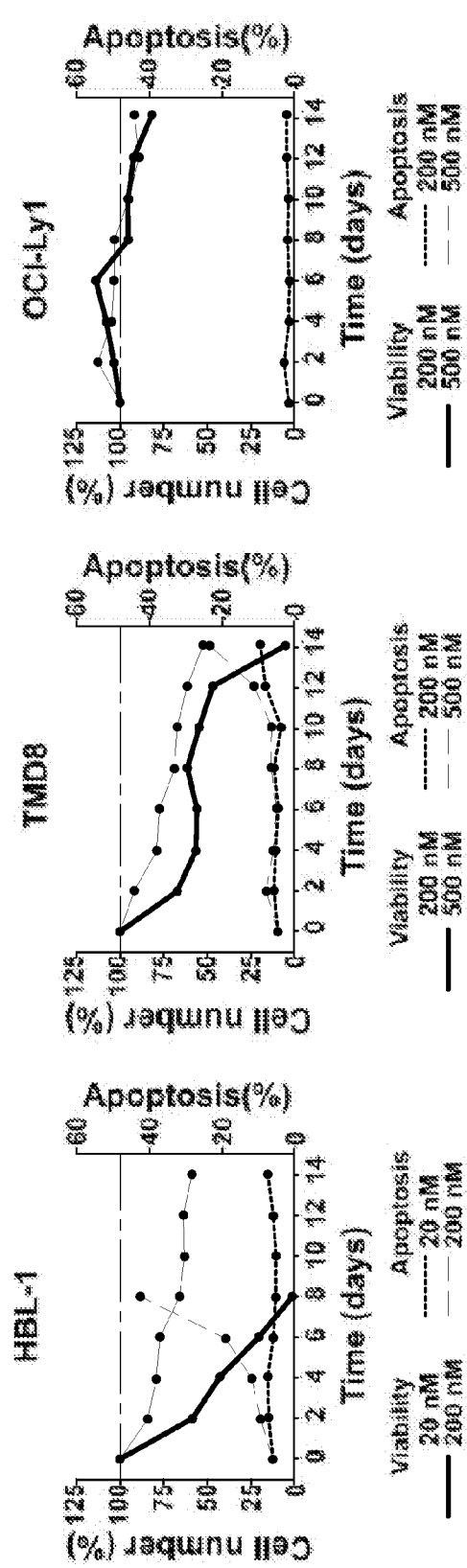
FIG. 5E shows graphical results of experiments demonstrating that whereas MI-2 had no effect on OCI-Ly1 cells, it profoundly suppressed both HBL-1 and TMD8 cells, with the former exhibiting earlier and higher abundance of apoptotic cells.

To explore in more detail the biological effects of MALT1 inhibition HBL-1, TMD8, OCI-Ly10 and the GCB-DLBCL cell line OCI-Ly1 were treated with increasing concentrations of MI-2. Cell proliferation was examined using the CFSE dilution assay by flow cytometry on viable cells at 48, 72 and 96 h. MI-2 substantially inhibited proliferation in HBL-1, TMD8 and OCI-Ly10 while it did not affect OCI-Ly1 (FIGS. 5C1, 5C2, 5C3). Using BrdU incorporation—DAPI staining and flow cytometry to assess cell cycle, it was evident that MI-2 induced a dose-dependent decrease in S phase, with reciprocal increment in the proportion of cells in G1-0 and Sub-G0 (FIG. 5D). To determine whether MALT1 inhibitors induced apoptosis the ABC-DLBCL cell lines HBL1 and TMD8 were treated daily with MI-2 at their respective $GI_{25}$ and $GI_{50}$, and the control OCI-Ly1 cell line at the higher doses used for TMD8. Trypan blue exclusion and apoptosis assessed by Annexin $V^+$ $DAPI^-$ flow cytometry was measured every 48 hr for a period of 14 days. Whereas MI-2 had no effect on OCI-Ly1 cells, it profoundly suppressed both HBL-1 and TMD8 cells, with the former exhibiting earlier and higher abundance of apoptotic cells (FIG. 5E). Using the more sensitive Caspase-3/7 cleavage assay we observed evidence of dose dependent apoptosis within 48 hr in both ABC-DLBCL cell lines. Hence MI-2 powerfully suppresses the growth and survival of ABC-DLBLC cell lines.

Compound MI-2 is Non-Toxic to Animals

To determine its suitability as a MALT1 lead compound for in vivo studies we examined whether MI-2 induced toxic effects in mice. Five C57BL/6 mice were exposed to daily intraperitoneal (IP) administration of increasing doses of MI-2 ranging from 0.05 to 25 mg/kg over the course of 10 days to a cumulative dose of 51.1 mg/kg and another five mice were exposed to vehicle only (5% DMSO, n=5) (FIG. 6A, Toxicity 1). There was no evidence of lethargy, weight loss (FIG. 6B, Toxicity 1) or other physical indicators of sickness. To ascertain if the maximal administered dose of 25 mg/kg is safe in a 14-day schedule, we exposed ten mice to daily IP administration of 25 mg/kg of MI-2 over 14 days to a cumulative dose of 350 mg/kg, using as controls five mice injected with vehicle only (FIG. 6A, Toxicity 2). Five mice were sacrificed after the 14-day course of MI-2 administration (together with the 5 controls) and the other 5 mice were sacrificed after a 10-day washout period to assess delayed toxicity. No toxic effects or other indicators of sickness, including weight loss (FIG. 6B, Toxicity 2) or tissue damage (macroscopic or microscopic), were noted (FIGS. 6C1, 6C2). Brain, heart, lung, liver, kidney, bowel, spleen, thymus and bone marrow tissues were examined. Bone marrow was normocellular with trilineage maturing hematopoiesis. Myeloid to erythroid ratio was 4-5:1. Megakaryocytes were normal in number and distribution. There was no fibrosis nor increased number of blasts or lymphocytes. Complete peripheral blood counts, biochemistry and liver function tests were normal (Table 2).

TABLE 2

Cell blood count and serum chemistry results from the Toxicity 2 experiment (25 mg/kg IP daily administration of MI-2 or equivalent volume of vehicle for 14 days).

| Test | Vehicle | MI-2_d14 | MI-2_d24 | Reference | Units |
|---|---|---|---|---|---|
| ALP | 92.6 | 83 | 100 | 23-181 | U/L |
| ALT | 29.6 | 25 | 23 | 16-58 | U/L |
| AST | 98.4 | 70 | 49.5 | 36-102 | U/L |
| CK | 885.8 | 202.8 | 119.5 | 358-1119 | U/L |
| GGT | 0 | 0 | 0 | | U/L |
| ALBUMIN | 3.26 | 3.12 | 3.15 | 2.5-3.9 | g/dL |
| TOTAL PROTEIN | 5.64 | 5.32 | 5.30 | 4.1-6.4 | g/dL |
| GLOBULIN | 2.38 | 2.20 | 2.15 | 1.3-2.8 | g/dL |
| TOTAL BILIRUBIN | 0.220 | 0.180 | 0.175 | 0-0.3 | mg/dL |
| DIRECT BILIRUBIN | 0.04 | 0.10 | 0.10 | | mg/dL |
| INDIRECT BILIRUBIN | 0.18 | 0.08 | 0.07 | | mg/dL |
| BUN | 26.6 | 23.4 | 27.0 | 14-32 | mg/dL |
| CREATININE | 0.24 | 0.22 | 0.20 | 0.1-0.6 | mg/dL |
| CHOLESTEROL | 87.8 | 85.4 | 91.75 | 70-100 | mg/dL |
| GLUCOSE[a] | 320.6 | 313.8 | 288.5 | 76-222 | mg/dL |
| CALCIUM | 11.06 | 10.88 | 10.80 | 7.6-10.7 | mg/dL |
| PHOSPHORUS | 10.62 | 9.46 | 9.65 | 4.6-10.5 | mg/dL |
| CHLORIDE | 107.4 | 108.4 | 106.7 | 103-115 | mEq/L |
| SODIUM | 154.2 | 152.8 | 153 | 148-154 | mEq/L |
| WBC | 7.98 | 7.83 | 9.03 | 5.4-16 | K/μL |
| RBC | 7.44 | 8.60 | 9.38 | 6.7-9.7 | M/μL |
| HEMOGLOBIN | 12.15 | 12.94 | 13.55 | 10.2-10.6 | g/dL |
| HEMATOCRIT | 35.77 | 40.86 | 45.02 | 32-54 | (%) |
| NEUTROPHILS | 1.19 | 1.18 | 1.85 | 0-1.8 | K/μL |
| LYMPHOCYTES | 6.26 | 6.29 | 6.76 | 2.5-10 | K/μL |
| MONOCYTES | 0.27 | 0.32 | 0.27 | 0-0.2 | K/μL |
| EOSINOPHILS | 0.21 | 0.03 | 0.11 | 0-0.5 | K/μL |
| BASOPHILS | 0.04 | 0.01 | 0.04 | 0-0.4 | K/μL |
| PLATELETS | 468 | 981 | 1275 | 799-1300 | K/μL |

[a]There was a mild increase in glucose in both vehicle and MI-2 treated animals perhaps due to administration of dextrose as an excipient, or because mice were not fasting.

These studies established the safety of MI-2 for use in anti-lymphoma efficacy studies.

MI-2 Suppresses Human ABC-DLBCL Xenografts and Primary Human DLBCLs Ex Vivo.

Figure 7A:
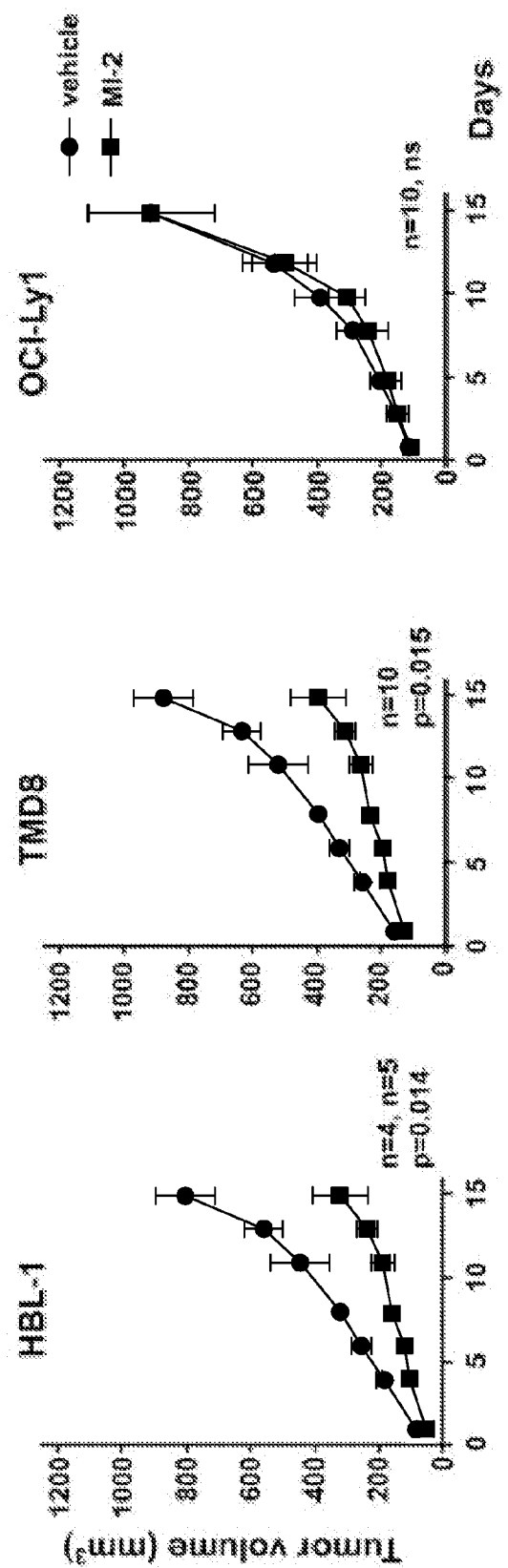
FIG. 7A shows graphical data demonstrating that MI-2 profoundly suppressed the growth of both the TMD8 (p=0.015, t-test) and HBL1 (p=0.014, t-test) ABC-DLBCL xenografts vs. vehicle, whereas it had no effect on the growth of the OCI-Ly1 tumors (p=0.47, t-test).
Figure 7B:
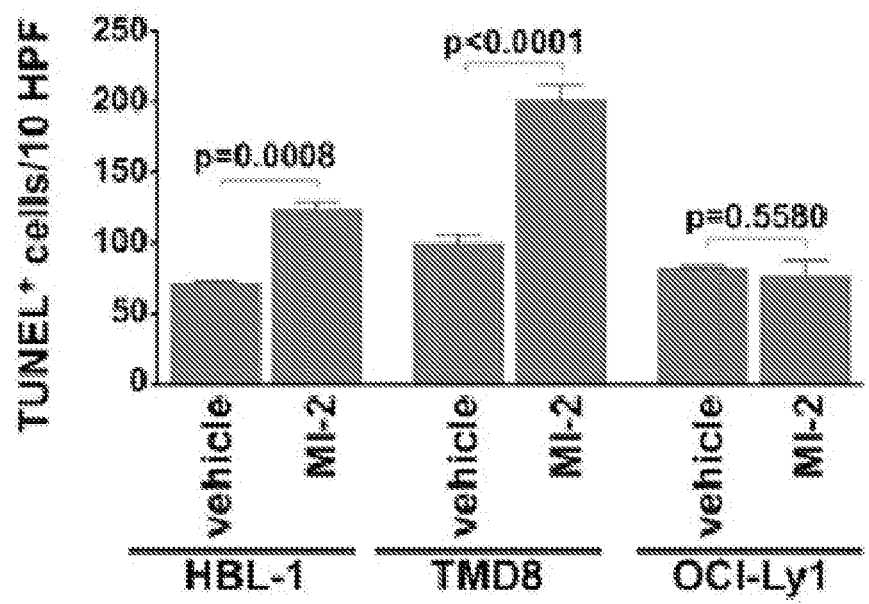
FIG. 7B shows graphical results of histological examination using the TUNEL assay to detect apoptotic cells, that showed a significant increase in apoptotic cells in MI-2-treated HBL-1 (p=0.0008, t-test) and TMD8 (p<0.0001, t-test) xenografts relative to vehicle but not in OCI-Ly1 xenografts (p=0.5580, t-test).
Figure 7C:
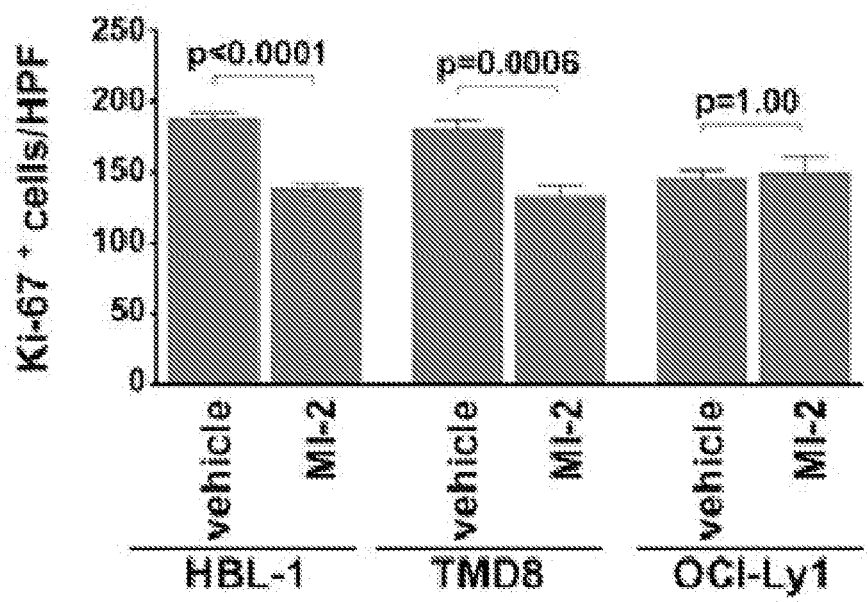
FIG. 7C shows graphical results of evidence of a significant decrease in proliferation as measured by Ki-67 staining in HBL-1 (p<0.0001, t-test) and TMD8 xenografts (p=0.0006, t-test) compared to vehicle, but observed no difference in OCI-Ly1 xenografts (p=1.0, t-test).
Figure 7D:
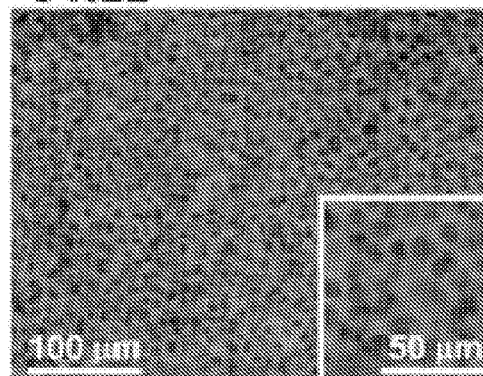
FIG. 7D shows stained microphotographs indicating that MI-2 treated tumors exhibited reduced c-REL nuclear protein.
Figure 7D:
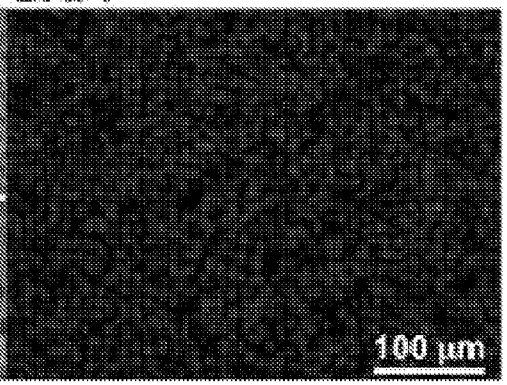
Figure 7D:
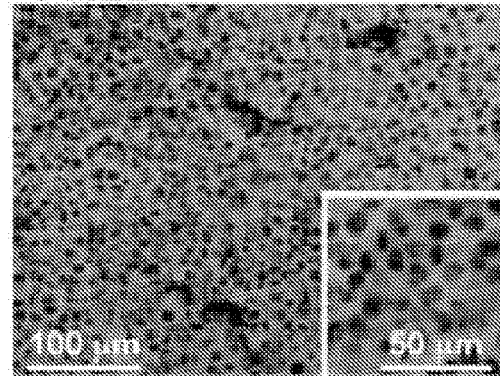
Figure 7D:
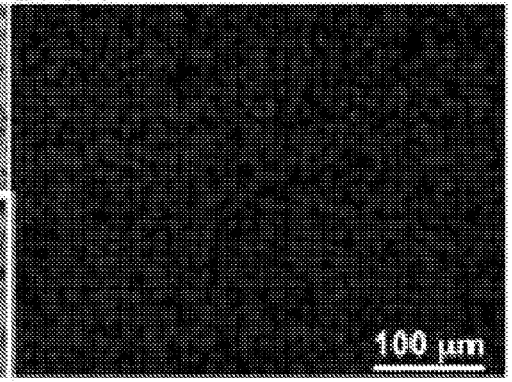

In order to determine whether MI-2 could suppress DLBCLs in vivo we engrafted HBL-1 and TMD8 (MALT1-dependent) and OCI-Ly1 (MALT1-independent) DLBCL cells into the right flank region of NOD-SCID mice. Once tumors reached an average of 120 mm$^3$ in volume, mice were randomized to receive IP injection of MI-2 25 mg/kg/day (n=10 for TMD8, n=5 for HBL1 and n=10 for OCI-Ly1) or vehicle (5% DMSO, n=10 for TMD8, n=4 for HBL1 and n=10 for OCI-Ly1). Animals were sacrificed 24 hr after the fourteenth injection. Remarkably, MI-2 profoundly suppressed the growth of both the TMD8 (p=0.015, t-test) and HBL1 (p=0.014, t-test) ABC-DLBCL xenografts vs. vehicle, whereas it had no effect on the growth of the OCI-Ly1 tumors (p=0.47, t-test) (FIG. 7A). The fact that OCI-Ly1 tumors were unaffected suggests that MI-2 activity is due to its effects on lymphoma cells rather than the host microenvironment. Histological examination using the TUNEL assay to detect apoptotic cells showed a significant increase in apoptotic cells in MI-2-treated HBL-1 (p=0.0008, t-test) and TMD8 (p<0.0001, t-test) xenografts relative to vehicle but not in OCI-Ly1 xenografts (p=0.5580, t-test) (FIG. 7B). We also observed a significant decrease in proliferation as measured by Ki-67 staining in HBL-1 (p<0.0001, t-test) and TMD8 xenografts (p=0.0006, t-test) compared to vehicle, but observed no difference in OCI-Ly1 xenografts (p=1.0, t-test; FIG. 7C). To evaluate the effect of MI-2 treatment on NF-κB signaling in xenografts, c-REL immunofluorescence was performed in paraffinized tumor sections. Consistent with data shown in FIGS. 4B and 4C, MI-2 treated tumors exhibited reduced c-REL nuclear protein (FIG. 7D). Therefore the MI-2 small molecule MALT1 inhibitor specifically suppresses proliferation, survival and NF-κB activity in ABC-DLBCLs in vivo in a lymphoma cell autonomous manner.

Figure 7E:
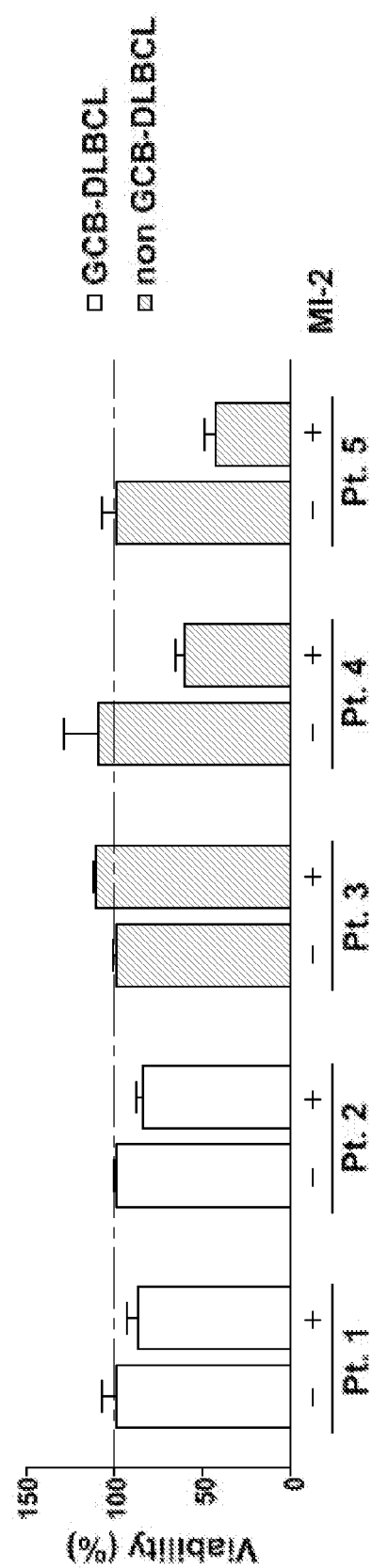
FIG. 7E shows graphical data obtained from single cell suspensions from lymph node biopsies of five DLBCL patients for whom their GCB vs. non-GCB status could be ascertained by immunohistochemistry using the Hans criteria, wherein lymphoma cells were isolated and exposed to 0.8 µM MI-2 or vehicle in four replicates. After 48 hr exposure, cell number and viability were determined using Trypan blue.

Finally, to determine whether MI-2 could also suppress primary human DLBCLs we obtained single cell suspensions from lymph node biopsies of five DLBCL patients for whom their GCB vs. non-GCB status could be ascertained by immunohistochemistry using the Hans criteria (Hans et al., 2004), as a surrogate for the GCB vs. ABC classification. Lymphoma cells were isolated and exposed to 0.8 μM MI-2 or vehicle in four replicates. After 48 hr exposure, cell number and viability were determined using Trypan blue. Notably, two of the non-GCB cases responded to MI-2 (p=0.04 and 0.003 vs. vehicle respectively), whereas none of the GCBs did (FIG. 7E). One of the non-GCB did not respond to MI-2, perhaps this case was not accurately classified by Hans's criteria. Overall these studies indicate that therapeutic targeting of MALT1 using the MI-2 small molecule inhibitor has powerful suppressive effects on human ABC-DLBCL cells and warrants translation for use in clinical trials.

The CARMA1-BCL10-MALT1 (CBM) complex assembles after antigen receptor activation leading to MALT1 dimerization and induction of its paracaspase activity. Cleavage of substrate proteins A20, BCL10, CYLD and RELB by MALT1 enhances NF-κB signaling through different mechanisms (Coornaert et al., 2008; Hailfinger et al., 2011; Rebeaud et al., 2008; Staal et al., 2011). BCR signaling is chronically active in a subset of ABC-DLBCLs due to somatic mutations of various genes leading to constitutive MALT1 signaling and NF-κB activation (Davis et al., 2010). Moreover constitutive expression of MALT1 in mice mimics MALT lymphomas and ABC-DLBCL (Vicente-Duenas et al., 2012). A small molecule inhibitor of the MALT1 proteolytic activity could therefore represent a very useful therapeutic agent for the treatment of ABC-DLBCL or MALT-lymphoma, and a variety of inflammatory and autoimmune disorders.

The catalytic activity of MALT1 is well defined and involves substrate features such as peptide length and amino acid composition and position (Hachmann et al., 2012). Purified MALT1, either the full-length protein or the paracaspase domain, is not very active in solution since it is present as a monomer instead of its active dimeric form. Dimerization can be induced by high salt concentrations, 1 M sodium citrate (Boatright et al., 2003). However these high salt conditions are non-physiological thus hindering biochemical screening for physiologically relevant small molecule inhibitors. To avoid this, we engineered a recombinant MALT1 protein fused to a leucine zipper domain, so that the paracaspase domain of MALT1 (340-789) is in its dimeric active conformation (FIG. 1A), allowing us to screen using more physiological conditions. Using this method, we identified 19 compounds able to inhibit MALT1 in vitro with $IC_{50}$ at the micromolar range. We focused on MI-2, which was the most potent inhibitor. We show that MI-2 is a covalent irreversible and selective inhibitor of MALT1, analogous to protease inhibitor drugs such as Telaprevir against the NS3/4A protease of Hepatitis C virus (Klibanov et al., 2011), the proteasome inhibitor Carfilzomib (Genin et al., 2010) and others (Powers et al., 2002). Although the peptide inhibitor Z-VRPR-FMK has been useful as a research tool, it is not suitable as a MALT1 therapeutic agent given its relatively large size, charge and consequent lower cell permeability. Accordingly MI-2 displayed superior activity in cell based assays with excellent cell penetration and indeed featured high concentration within cells, and yet was still highly selective for MALT1 vs. other caspases. Notably, a selective and irreversible small molecule inhibitor of the tyrosine kinase BTK, PCI-32765 (Ibrutinib) is currently under clinical development in patients with B-cell non-Hodgkin lymphoma (Honigberg et al., 2010). Irreversibility of MI-2 may provide pharmacokinetic advantages. As ABC-DLBCL have chronically active BCR signaling, prolonged suppression of MALT1-cleavage would likely be necessary for maximal anti-lymphoma activity. Using an irreversible inhibitor, activity will only return when new enzyme is synthesized. This may allow drug to be effective at a lower plasma concentration thus reducing dosing level and frequency, limiting the requirement for long plasma half-life without compromising efficacy, and minimizing potential toxic effects related to prolonged exposure to circulating drug. Indeed our detailed studies indicated that MI-2 was non-toxic in animals. This result is consistent with the fact that MALT1 is the only paracaspase in humans and MALT1-deficient mice are relatively healthy (Ruefli-Brasse et al., 2003; Ruland et al., 2003).

Chronic activation of the BCR pathway in ABC-DLBCL is mediated by several different mechanisms, many of them upstream of MALT1. ABC-DLBCL is addicted to this pathway and is often specifically addicted to MALT1 cleavage activity (Ferch et al., 2009; Hailfinger et al., 2009; Ngo et al., 2006). Notably, MI-2 selectively killed ABC-DLBCL cell lines with CD79A/B, CARMA1 and/or MYD88 mutations but not those occurring in proteins downstream of MALT1 including those with A20 homozygous deletion or TAK1 mutation (FIG. 5A and Table 1). These findings underline the importance of targeted resequencing of recurrently mutated alleles in lymphoma for the rational deployment of targeted therapeutics. Although the full spectrum of lymphomas that can be targeted with MALT1 inhibitors is not fully clear yet, using an ex vivo system we were able to show for the first time that primary human non GCB-DLBCL specimens are also addicted to MALT1 and are suppressed by MI-2.

As single agents are generally not curative and rapidly generate resistance (Misale et al., 2012), there is a growing interest in combinatorial-targeted therapy. Rational combination of MALT1 cleavage inhibition could include combination with tyrosine kinase inhibitors targeting Src family (dasatinib, saracatinib, bosutinib, and KX01), Syk (fostamatinib disodium) or Btk (PCI-32765). These drugs would likely synergize with MALT1 cleavage inhibition of NF-κB by further inhibiting BCR signaling, including Mitogen-Activated Protein (MAP) Kinases and Phosphatidylinositol (PI) 3-kinase (Lim et al., 2012). PKC inhibition would also be a potentially beneficial combination as it could further inhibit the NF-κB pathway, including those activities dependent on MALT1, but independent of its proteolytic activity. The PKC inhibitor sotrastaurin, in clinical trials for prevention of transplantation rejection and treatment of psoriasis (Manicassamy, 2009; Matz et al., 2011), has been recently shown to inhibit growth of ABC-DLBCL xenografted tumors (Naylor et al., 2011), pointing to its potential use as anti-lymphoma therapy for this lymphoma subtype. ABC-DLBCLs also feature BCL6 translocation, SPI-B amplification or PRDM1 deletion or mutation (Lenz and Staudt, 2010). BCL6 inhibitors promote apoptosis and cell cycle arrest through release of critical checkpoint genes (Cerchietti et al., 2010; Cerchietti et al., 2009; Polo et al., 2004). Combination of MI-2 and BCL6 inhibitors would thus suppress two critical pathways in ABC-DLBCLs (BCL6 and NF-κB) potentially leading to therapeutic synergy. Taken together, the results reported here identify MI-2 as a lead compound targeting MALT1 and demonstrate the significance, safety and efficacy of MALT1 as a therapeutic target and MI-2 as a therapeutic agent for the treatment of aggressive NHLs that are both dependent on NF-κB signals and resistant to conventional chemotherapeutic regimens.

EXAMPLES

High-Throughput Screening for MALT1 Proteolytic Activity Inhibitors

Ac-LRSR-AMC was used as substrate and reactions were measured with excitation/emission wavelengths of 360/465 nm. Average of control values was used in the calculation of percent inhibition. The final percent inhibition was calculated with the formula: {[fluorescence$_{test\ compound}$(T2−T1)−fluorescence$_{neg\ ctrl}$(T2−T1)]/[fluorescence$_{pos\ ctrl}$(T2−T1)−fluorescence$_{neg\ ctrl}$(T2−T1)]}×100. Z-VRPR-FMK (300 nM) was used as positive control and, buffer only as negative control.

Growth-Inhibition Determination

Cell proliferation was determined by ATP quantification using a luminescent method (CellTiter-Glo, Promega, Madison, Wis.) and Trypan blue dye-exclusion (Sigma, St. Louis, Mo.). Cell viability in drug-treated cells was normalized to their respective controls (fractional viability) and results are given as 1-fractional viability. CompuSyn software (Biosoft, Cambridge, UK) was used to determine drug concentrations inhibiting fractional growth compared to controls.

Mouse Xenograft Experiments

Eight-week old male SCID NOD.CB17-Prkdc$^{scid}$/J mice were subcutaneously injected with low-passage $10^7$ human HBL-1, TMD8 or OCI-Ly1 cells. Treatment was administered by intra-peritoneal injection. Tumor volume was monitored by three-weekly digital calipering. All procedures followed US NIH protocols and were approved by the Animal Institute Committee of the Weill Cornell Medical College.

Accession Number

Microarray data: GSE40003.

High-Throughput Screening for MALT1 Proteolytic Activity Inhibitors

The screening consisted of a 20 µl reaction in 384-well black plates (Greiner Bio One, Wemmel, Belgium, catalogue #784076) with 100 nM LZ-MALT1, 200 µM Ac-LRSR-AMC, and 12.5 µM test compound in buffer A (20 mM HEPES pH 7.5, 10 mM KCl, 1.5 mM MgCl$_2$, 1 mM EDTA, 1 mM DTT, 0.01% Triton X-100). The reactions were measured with excitation/emission wavelengths of 360/465 nm using Envision Multilabel Reader (Perkin-Elmer, Waltham, Mass.). Two time points were measured for each reaction; the fluorescence difference between time points (T2−T1) was considered as MALT1 activity to eliminate false positives due to compound autofluorescence. Average of control values was used in the calculation of percent inhibition. The final percent inhibition was calculated with the formula: {[fluorescence$_{test\ compound}$(T2−T1)−fluorescence$_{neg\ ctrl}$(T2−T1)]/[fluorescence$_{pos\ ctrl}$(T2−T1)−fluorescence$_{neg\ ctrl}$(T2−T1)]}×100. Z-VRPR-FMK (300 nM) was used as positive control, buffer only was used as negative control. Using 40% inhibition as a threshold, 324 compounds were identified as potential MALT1 inhibitors. The positive hits were validated in concentration-response experiments within a dose range of 0.122 µM to 62.5 µM to determine IC$_{50}$ (50% of inhibition) of the compounds. Activity was also validated using recombinant full-length wild-type MALT1 in addition to the LZ-MALT1 used for screening.

Protein Expression and Purification

MALT1 (340-789) was fused with leucine-zipper sequence from GCN4 (251-281) in the N-terminus (LZ-MALT1). N-terminal his-tagged LZ-MALT1 was expressed in E. Coli and purified by Ni-NTA affinity chromatography (Qiagen, Valencia, Calif.) followed by gel filtration chromatography with Superdex 200 HR 10/300 (GE Healthcare, UK) in buffer containing 20 mM Tris (pH 7.5), 150 mM NaCl, and 5 mM DTT.

Cell Culture

DLBCL cell lines OCI-Ly1, OCI-Ly7 and OCI-Ly10 were grown in 80% Iscove's medium, 20% FBS and penicillin G/streptomycin. DLBCL cell lines HBL-1, TMD8, U2932 were cultured in 90% RPMI medium, 10% FBS, 2 mM glutamine, 10 mM Hepes and penicillin G/streptomycin. DLBCL cell lines OCI-Ly3 and HLY1 were cultured in 80% RPMI medium, 20% FBS, 2 mM glutamine, 10 mM Hepes and penicillin G/streptomycin. 293T cells were cultured in 90% D-MEM, 10% FBS and penicillin G/streptomycin. All cell lines were cultured at 37° C. in a humidified atmosphere of 5% CO$_2$. Cell lines were authenticated by single nucleotide polymorphism profiling (fingerprinting).

Growth-Inhibition Determination

DLBCL cell lines were grown in exponential growth conditions during the 48 hr of treatment. Cell proliferation was determined by ATP quantification using a luminescent method (CellTiter-Glo, Promega, Madison, Wis.) and Trypan blue dye-exclusion (Sigma, St. Louis, Mo.). Luminescence was measured using the Synergy4 microplate reader (BioTek Instruments, Winooski, Vt.). Standard curves for each cell line were calculated by plotting the cell number (determined by the Trypan blue method) against their luminescence values and number of cells was calculated accordingly. Cell viability in drug-treated cells was normalized to their respective controls (fractional viability) and results are given as 1-fractional viability. CompuSyn software (Biosoft, Cambridge, UK) was used to determine the drug concentration that inhibits the growth of cell lines by 25% compared to control ($GI_{25}$). Experiments were performed in triplicate.

Analog Screening Based on the Lead Compound MI-2

Similarity searching was set to a 0.7 cutoff and performed using the Collaborative Drug Discovery (CDD, Burlingame, Calif.) Database's (www.collaborativedrug.com)_similarity search function. The CDD search function is based on ChemAxon's (www.chemaxon.com, Budapest, Hungary) standard Tanimoto similarity functions of hashed fingerprints as described in (http://www.chemaxon.com/jchem/doc/dev/search/index.html#simil). Briefly, hashed fingerprints of every query structure are calculated and then the dissimilarity formula is applied as: $1-(N_{A\&B}/N_A+N_B-N_{A\&B})$, Where $N_A$ and $N_B$ are the number of bits set in the fingerprint of molecule A and B, respectively, $N_{A\&B}$ is the numbers of bits that are set in both fingerprints. The dissimilarity threshold is a number between 0 and 1, which specifies a cutoff limit in the similarity calculation. If the dissimilarity value is less than the threshold, then the query structure and the given database structure are considered similar. Analogue screening was performed using the same methods as in primary screening, except it was done in triplicates. 19 compounds with higher activity than MI-2 were selected for further validation.

NMR

Uniformly $^{15}N$ and $^{13}C$ labeled MALT1 (329-728) was expressed in BL21 (DE3) *E. coli* growing in M9 medium containing 1 g/l [$^{15}N$]ammonium chloride and 3 g/l [$^{13}C$] glucose (Cambridge Isotope Labs, Andover, Mass.) and purified from *E. coli* cell lysate as described in (Wiesmann et al., 2012).

Standard 2D $^1H$ $^{13}C$ NMR spectra of MALT1 (329-728) were recorded in samples containing 10.0 mg/ml protein in 50 mM HEPES (pH 7.5), 50 mM NaCl, and 10% $D_2O$. NMR spectroscopy experiments were recorded on Bruker AV 500 MHz spectrometer (Bruker, Billerica, Mass.), at 310K.

Standard 2D $^1H$ $^{15}N$ HSQC spectra of MALT1 (329-728) were recorded in samples containing 70 µM protein in 25 mM Tris pH 7.5, 250 mM NaCl, 5 mM DTT, 10% $D_2O$, 0.02% $NaN_3$, 2% DMSO. HSQCs were run on a 600 MHz Varian (Varian, Palo Alto, Calif.) at 37° C.

HPLC/ESI-MS

HPLC/ESI-MS experiments were carried out on 5 µl sample at 1 mg/ml protein concentration. Separation of proteins was performed on a HP 1100 system (Hewlett Packard, Palo Alto, Calif., USA) employing a 1 mm×150 mm LC Packings column packed with POROS R1/H (Perseptive Biosystems, Foster City, Calif., USA). The column was kept at 80° C. Samples were injected onto the column using a CTC PAL autosampler (CTC, Zwingen Switzerland) fitted with a Valco model C6UW HPLC valve (Valco, Houston, Tex., USA) and a 10 µl injection loop. HPLC was controlled by MassLynx software (Micromass, Manchester, UK). UV detection was performed at 214 nm. Eluent A was water containing 0.05% TFA. Eluent B was a 1:9 mixture of water:acetonitrile containing 0.045% TFA. A gradient from 20% B to 90% B was run in 20 minutes. The flow rate was typically 60 µl/min. The total flow from the LC system was introduced into the UV detection cell prior to introduction in the ESI source. The HPLC system was controlled and the signal from the UV detector was processed using MassLynx software. Mass spectroscopy was carried out using a Q-tof (Micromass, Manchester, UK) quadrupole time-of-flight hybrid tandem mass spectrometer equipped with a Micromass Z-type electrospray ionization source. Acquisition mass range was typically m/z 500-2000. Data were recorded and processed using MassLynx software. Calibration of the 500-2000 m/z scale was achieved by using the multiple-charged ion peaks of horse heart myoglobin (MW 16,951.5 Da).

Dose-Effect and Time-Course of MALT1 Inhibition

In a 384 well black plate (Greiner Bio One, Wemmel Belgium, catalogue #784076), 8 pMole of purified LZ-MALT1 were incubated with compound MI-2 at different concentrations (125, 62.5, 31.25, 15.625, 7.8125 or 0 µM) for indicated time (from 5 minutes to 80 minutes) at room temperature in buffer containing 5% DMSO, 20 mM HEPES pH 7.5, 10 mM KCl, 1.5 mM $MgCL_2$, 1 mM EDTA, 1 mM DTT, 0.01% TritonX-100, then 4 Mol of Ac-LRSR-AMC were then added into each mixture to initiate reactions. The reactions were monitored in a SpectraMax M5 plate reader (Molecular Devices, Sunnyvale, Calif. USA) with excitation/emission wavelength at 360/465 nm and 20 seconds intervals. Normalized percentage of inhibition was calculated with the following formula: $(M_{(T2-T1)}-N_{(T2-T1)})/(P_{(T2-T1)}-N_{(T2-T1)})*100$, where $M_{(T2-T1)}$ is the difference signal of compound at time point 200s and 0s, $N_{(T2-T1)}$ is the difference signal of negative control buffer only, $P_{(T2-T1)}$ is the difference signal of positive control Z-VRPR-FMK.

MI-2 Docking to MALT1

The structure of MI-2 was generated and its geometry was optimized. The atomic coordinates of MALT1 containing its paracaspase and Ig3 domains in complex with the Z-VRPR-FMK peptide inhibitor (PDB ID: 3UOA) (Wiesmann et al., 2012; Yu et al., 2011) were chosen for inhibitor docking. After removing the peptide inhibitor and solvent molecules, hydrogen atoms were added to the MALT1 structure. The docking simulation started with defining 3D potential grids for MALT1 against MI-2. The calculated grid maps were of dimensions 60×40×40 points with the spacing of 0.375 Å/point. The generic algorithm in AutoDock 4.2 (Morris et al., 2009) was used and the docking was performed with MALT1 as a rigid molecule while allowing flexibility in the MI-2 inhibitor. The final results were ranked based on the predicted binding free energy.

Western Blot

Equal amounts of total protein (20-75 µg) were separated on sodium dodecyl sulfate-polyacrylamide gel electrophoresis (SDS-PAGE), and electrotransferred onto nitrocellulose membranes. Membranes were incubated with primary antibodies (MALT1, BCL-10, CYLD from Santa Cruz Biotechnologies, Santa Cruz, Calif.; A20 from eBioscience, San Diego, Calif.; phospho-IκB-α, IκB-α, c-REL, RELB from Cell Signaling, Danvers, Mass. and α-Tubulin from Sigma), followed by secondary antibodies conjugated to horseradish peroxidase, which were detected by chemiluminescence (Pierce, Thermo Scientific, Rockford, Ill.).

Flow Cytometry

To study the effect of MI-2 in cell proliferation, cells were labeled with carboxyfluorescein diacetate succinimidyl ester (CFSE, Invitrogen, Life Technologies, Grand Island, N.Y.) at 0.5 µM and 37° C. for 10 minutes. CFSE covalently labels long-lived intracellular molecules with carboxyfluorescein. Following each cell division, fluorescent molecules dilute in daughter cells, allowing comparative study of the kinetics of cell division. Cells were stained with DAPI (Sigma), followed by flow cytometry. $DAPI^{neg}$ cells were gated for analysis.

To determine cell-cycle distribution, cells were analyzed by flow cytometry using pulse-BrdU (bromodeoxyuridine) incorporation with the APC BrdU Flow Kit (BD Pharmingen, San Jose, Calif.).

Apoptosis was assessed by AnnexinV-APC/DAPI (BD Pharmingen) staining followed by flow cytometry.

Nuclear export of c-REL was studied by flow cytometry. Cells were treated as indicated and total cells or isolated nuclei were prepared and stained for c-REL. Total cells were fixed and permeabilized using the Intrastain kit from Dako (Glostrup, Denmark). For nuclei extraction, cells were resuspended in cold nuclei extraction buffer (320 mM sucrose, 5 mM $MgCl_2$, 10 mM HEPES, 1% Triton X-100 at pH 7.4), incubated for 10 min on ice and washed twice with nuclei wash buffer (320 mM sucrose, 5 mM $MgCl_2$, 10 mM HEPES at pH 7.4, no Triton X-100). Nuclei yield and integrity were confirmed by microscopic examination with trypan blue staining. For labeling, nuclei wash buffer was supplemented with 1% BSA, 0.1% sodium azide and 1:100 c-REL antibody (Cell Signaling). Cells were washed then incubated with Alexa Fluor-488 conjugated secondary antibodies from Invitrogen. Cells were washed again and stained with DAPI followed by flow cytometry.

Luciferase Assays

Reporter assays were performed in 293T cells seeded at a density of $2 \times 10^5$ cells per well of a 12-well dish. 100 ng of (NF-κB)$_5$-Luc2CP-pGL4 and 10 ng of TK-Renilla internal control plasmid were cotransfected along with 25 ng of the indicated plasmids (MIGR1-MALT1$^{WT}$ or MIGR1-MALT1$^{C464A}$ and pcDNA4-Flag-Bcl10) using Lipofectamine 2000 (Invitrogen). Lysates were submitted to dual luciferase assays following manufacturer's protocol (Promega). In HBL-1, 5 μg of (NF-κB)$_5$-Luc2CP-pGL4 and 50 ng of TK-Renilla internal control plasmid per $5 \times 10^6$ cells were cotransfected using nucleofection (Amaxa, Lonza, Basel, Switzerland). Forty-eight hours after transfection, cells were plated at a density of $5 \times 10^4$ cells per well of a 24-well plate and treated as indicated. Lysates were submitted to dual luciferase assays following manufacturer's protocol (Promega).

Microarray Data Analysis

RNA from HBL-1 and TMD8 cells treated for 8 hours with compound MI-2 or vehicle at indicated concentrations and mRNA was isolated using the RNeasy Plus kit (Qiagen, Valencia, Calif.) followed by DNase treatment using the RNase-Free DNase reagent (Qiagen). RNA integrity was determined using the RNA 6000 Nano LabChip Kit on an Agilent 2100 Bioanalyzer (Agilent Technologies, Santa Clara, Calif.). Samples were processed following Illumina recommendations and cRNA was hybridized to the HumanHT-12 v4 Expression BeadChip (Illumina, San Diego, Calif.). Arrays were scanned on the iScan system. Data pre-processing and quality control were performed using GenomeStudio. The data were $log_2$-transformed combined with quantile normalization (Du et al., 2008). GEO accession number GSE40003.

In order to determine the biological significance of the results, enrichment tests with respect to sets of related genes were carried out. To this end, we used GSEA (Gene Set Enrichment Analysis) software, and datasets were pre-ranked by fold change value (Subramanian et al., 2005). The p-values for each gene-set were computed on the basis of 1,000 iterations and multiple hypotheses testing correction for FDR calculation (Storey and Tibshirani, 2003).

Mouse Xenograft Experiments

Eight-week old male SCID NOD.CB17-Prkdc$^{scid}$/J mice were purchased from Jackson Laboratories (Bar Harbor, Minn.) and housed in a clean environment. Mice were subcutaneously injected with low-passage $10^7$ human TMD8 or OCI-Ly1 cells in 50% matrigel (BD Biosciences, #354234). Treatment was initiated when tumors reached an average size of 120 mm$^3$ (17 days post-transplantation). Drugs were reconstituted in DMSO and stored at −80° C. until used and were administered by intra-peritoneal injection. Tumor volume was monitored by three-weekly digital calipering (Fisher Scientific, Thermo Scientific, Rockford, Ill.) and calculated using the formula (smallest diameter$^2$ × largest diameter)/2. Data were expressed as mean±SEM, and differences were considered statistically significant at p<0.05 by paired Student's t-test. All procedures involving animals followed US NIH protocols and were approved by the Animal Institute Committee of the Weill Cornell Medical College of Cornell University.

Immunofluoresce in Paraffin (IF-P) and Immunohistochemistry (IHC)

Paraffin-embedded tumor xenografts were sectioned, dewaxed and submitted to antigen retrieval. For IF-P, Alexa Fluor-488 conjugated secondary antibodies from Invitrogen where used and cell nuclei where counterstained with DAPI. Fluorescent images were taken using an Axiovert 200M fluorescent microscope (Carl Zeiss Inc., Thornwood, N.Y.). For IHC, biotin-conjugated secondary antibodies where used. Then avidin/biotin peroxidase was applied to the slides (Vector Laboratories). Color was developed with diaminobenzoate chromogen peroxidase substrate (Vector) and counterstained with hematoxilin-eosyn. Pictures were obtained using an AxioCam (Carl Zeiss Inc.) camera attached to an AxioSkop II light microscope (Carl Zeiss Inc.). Samples were reviewed by a pathologist.

Tunel

Terminal deoxynucleotidyl transferase dUTP nick end labeling, TUNEL assay (ApopTag, Chemicon, Temecula, Calif.), was used to detect apoptotic DNA fragmentation (Gavrieli et al., 1992). Briefly, formalin-fixed paraffin-embedded xenografted tumors were deparaffinized and pre-treated with trypsin (Zymed, San Francisco, Calif.) to expose DNA. Endogenous peroxidase was quenched using 3% hydrogen peroxide (Sigma) followed by incubation with TdT enzyme for 1 hour. Then, anti-digoxigenin-peroxidase was applied to the slides. Color was developed with diaminobenzoate chromogen peroxidase substrate (Vector Laboratories, Burlingame, Calif.) and counterstained with methyl green (Fisher Scientific, Thermo Scientific, Rockford, Ill.). Pictures were obtained using an AxioCam (Carl Zeiss Inc.) camera attached to an AxioSkop II light microscope (Carl Zeiss Inc.). Samples were reviewed by pathologist.

Primary Cells

Patient de-identified tissues were obtained in accordance with the guidelines and approval of the Weill Cornell Medical College Review Board. Patient samples were processed as previously described (Cerchietti et al., 2010). Briefly, single cell suspensions from lymph node biopsies were obtained by physical disruption of tissues followed by cell density gradient separation (Fico/Lite LymphoH, Atlanta Biologicals, Lawrenceville, Ga.). Cell number and viability were determined by Trypan blue exclusion. Primary DLBCL cells were cultured in 96-well plates. Cells were grown in advanced RPMI medium with 20% FBS supplemented with antibiotics for 48 hours. Cells were exposed to 0.8 μM of MI-2 (1 μM for Pt.2) or control (DMSO) in quadruplicates. After 48 hr of exposure, viability was determined by using Trypan blue (Sigma). All samples were normalized to their own replicate control. Statistical significance was calculated using paired T-test.

DOCUMENTS CITED

Alizadeh, A. A., Eisen, M. B., Davis, R. E., Ma, C., Lossos, I. S., Rosenwald, A., Boldrick, J. C., Sabet, H., Tran, T., Yu, X., et al. (2000). Distinct types of diffuse large B-cell lymphoma identified by gene expression profiling. Nature 403, 503-511.

Boatright, K. M., Renatus, M., Scott, F. L., Sperandio, S., Shin, H., Pedersen, I. M., Ricci, J. E., Edris, W. A., Sutherlin, D. P., Green, D. R., and Salvesen, G. S. (2003). A unified model for apical caspase activation. Molecular cell 11, 529-541.

Cerchietti, L. C., Ghetu, A. F., Zhu, X., Da Silva, G. F., Zhong, S., Matthews, M., Bunting, K. L., Polo, J. M., Fares, C., Arrowsmith, C. H., et al. (2010). A small-molecule inhibitor of BCL6 kills DLBCL cells in vitro and in vivo. Cancer cell 17, 400-411.

Cerchietti, L. C., Yang, S. N., Shaknovich, R., Hatzi, K., Polo, J. M., Chadburn, A., Dowdy, S. F., and Melnick, A. (2009). A peptomimetic inhibitor of BCL6 with potent antilymphoma effects in vitro and in vivo. Blood 113, 3397-3405.

Compagno, M., Lim, W. K., Grunn, A., Nandula, S. V., Brahmachary, M., Shen, Q., Bertoni, F., Ponzoni, M., Scandurra, M., Califano, A., et al. (2009). Mutations of multiple genes cause deregulation of NF-kappaB in diffuse large B-cell lymphoma. Nature 459, 717-721.

Coornaert, B., Baens, M., Heyninck, K., Bekaert, T., Haegman, M., Staal, J., Sun, L., Chen, Z. J., Marynen, P., and Beyaert, R. (2008). T cell antigen receptor stimulation induces MALT1 paracaspase-mediated cleavage of the NF-kappaB inhibitor A20. Nat Immunol 9, 263-271.

Davis, R. E., Ngo, V. N., Lenz, G., Tolar, P., Young, R. M., Romesser, P. B., Kohlhammer, H., Lamy, L., Zhao, H., Yang, Y., et al. (2010). Chronic active B-cell-receptor signalling in diffuse large B-cell lymphoma. Nature 463, 88-92.

Dierlamm, J., Baens, M., Wlodarska, I., Stefanova-Ouzounova, M., Hernandez, J. M., Hossfeld, D. K., De Wolf-Peeters, C., Hagemeijer, A., Van den Berghe, H., and Marynen, P. (1999). The apoptosis inhibitor gene API2 and a novel 18q gene, MLT, are recurrently rearranged in the t(11; 18)(q21; q21) associated with mucosa-associated lymphoid tissue lymphomas. Blood 93, 3601-3609.

Dierlamm, J., Murga Penas, E. M., Bentink, S., Wessendorf, S., Berger, H., Hummel, M., Klapper, W., Lenze, D., Rosenwald, A., Haralambieva, E., et al. (2008). Gain of chromosome region 18q21 including the MALT1 gene is associated with the activated B-cell-like gene expression subtype and increased BCL2 gene dosage and protein expression in diffuse large B-cell lymphoma. Haematologica 93, 688-696.

Farinha, P., and Gascoyne, R. D. (2005). Molecular pathogenesis of mucosa-associated lymphoid tissue lymphoma. Journal of clinical oncology: official journal of the American Society of Clinical Oncology 23, 6370-6378.

Ferch, U., Kloo, B., Gewies, A., Pfander, V., Duwel, M., Peschel, C., Krappmann, D., and Ruland, J. (2009). Inhibition of MALT1 protease activity is selectively toxic for activated B cell-like diffuse large B cell lymphoma cells. The Journal of experimental medicine 206, 2313-2320.

Ferch, U., zum Buschenfelde, C. M., Gewies, A., Wegener, E., Rauser, S., Peschel, C., Krappmann, D., and Ruland, J. (2007). MALT1 directs B cell receptor-induced canonical nuclear factor-kappaB signaling selectively to the c-Rel subunit. Nat Immunol 8, 984-991.

Genin, E., Reboud-Ravaux, M., and Vidal, J. (2010). Proteasome inhibitors: recent advances and new perspectives in medicinal chemistry. Current topics in medicinal chemistry 10, 232-256.

Gross, O., Grupp, C., Steinberg, C., Zimmermann, S., Strasser, D., Hannesschlager, N., Reindl, W., Jonsson, H., Huo, H., Littman, D. R., et al. (2008). Multiple ITAM-coupled NK-cell receptors engage the Bcl10/Malt1 complex via Carma 1 for NF-kappaB and MAPK activation to selectively control cytokine production. Blood 112, 2421-2428.

Hachmann, J., Snipas, S. J., van Raam, B. J., Cancino, E. M., Houlihan, E. J., Poreba, M., Kasperkiewicz, P., Drag, M., and Salvesen, G. S. (2012). Mechanism and specificity of the human paracaspase MALT1. The Biochemical journal 443, 287-295.

Hailfinger, S., Lenz, G., Ngo, V., Posvitz-Fejfar, A., Rebeaud, F., Guzzardi, M., Penas, E. M., Dierlamm, J., Chan, W. C., Staudt, L. M., and Thome, M. (2009). Essential role of MALT1 protease activity in activated B cell-like diffuse large B-cell lymphoma. Proceedings of the National Academy of Sciences of the United States of America 106, 19946-19951.

Hailfinger, S., Nogai, H., Pelzer, C., Jaworski, M., Cabalzar, K., Charton, J. E., Guzzardi, M., Decaillet, C., Grau, M., Dorken, B., et al. (2011). Malt1-dependent RelB cleavage promotes canonical NF-kappaB activation in lymphocytes and lymphoma cell lines. Proceedings of the National Academy of Sciences of the United States of America 108, 14596-14601.

Hans, C. P., Weisenburger, D. D., Greiner, T. C., Gascoyne, R. D., Delabie, J., Ott, G., Muller-Hermelink, H. K., Campo, E., Braziel, R. M., Jaffe, E. S., et al. (2004). Confirmation of the molecular classification of diffuse large B-cell lymphoma by immunohistochemistry using a tissue microarray. Blood 103, 275-282.

Honigberg, L. A., Smith, A. M., Sirisawad, M., Verner, E., Loury, D., Chang, B., Li, S., Pan, Z., Thamm, D. H., Miller, R. A., and Buggy, J. J. (2010). The Bruton tyrosine kinase inhibitor PCI-32765 blocks B-cell activation and is efficacious in models of autoimmune disease and B-cell malignancy. Proceedings of the National Academy of Sciences of the United States of America 107, 13075-13080.

Honma, K., Tsuzuki, S., Nakagawa, M., Tagawa, H., Nakamura, S., Morishima, Y., and Seto, M. (2009). TNFAIP3/A20 functions as a novel tumor suppressor gene in several subtypes of non-Hodgkin lymphomas. Blood 114, 2467-2475.

Klibanov, O. M., Williams, S. H., Smith, L. S., Olin, J. L., and Vickery, S. B. (2011). Telaprevir: a novel NS3/4 protease inhibitor for the treatment of hepatitis C. Pharmacotherapy 31, 951-974.

Lenz, G., Davis, R. E., Ngo, V. N., Lam, L., George, T. C., Wright, G. W., Dave, S. S., Zhao, H., Xu, W., Rosenwald, A., et al. (2008a). Oncogenic CARD11 mutations in human diffuse large B cell lymphoma. Science 319, 1676-1679.

Lenz, G., and Staudt, L. M. (2010). Aggressive lymphomas. The New England journal of medicine 362, 1417-1429.

Lenz, G., Wright, G. W., Emre, N. C., Kohlhammer, H., Dave, S. S., Davis, R. E., Carty, S., Lam, L. T., Shaffer, A. L., Xiao, W., et al. (2008b). Molecular subtypes of diffuse large B-cell lymphoma arise by distinct genetic pathways. Proceedings of the National Academy of Sciences of the United States of America 105, 13520-13525.

Lim, K. H., Yang, Y., and Staudt, L. M. (2012). Pathogenetic importance and therapeutic implications of NF-kappaB in lymphoid malignancies. Immunological reviews 246, 359-378.

Lucas, P. C., Yonezumi, M., Inohara, N., McAllister-Lucas, L. M., Abazeed, M. E., Chen, F. F., Yamaoka, S., Seto, M., and Nunez, G. (2001). Bcl10 and MALT1, independent targets of chromosomal translocation in malt lymphoma, cooperate in a novel NF-kappa B signaling pathway. The Journal of biological chemistry 276, 19012-19019.

Manicassamy, S. (2009). Sotrastaurin, a protein kinase C inhibitor for the prevention of transplant rejection and treatment of psoriasis. Curr Opin Investig Drugs 10, 1225-1235.

Matz, M., Naik, M., Mashreghi, M. F., Glander, P., Neumayer, H. H., and Budde, K. (2011). Evaluation of the novel protein kinase C inhibitor sotrastaurin as immunosuppressive therapy after renal transplantation. Expert opinion on drug metabolism & toxicology 7, 103-113.

Misale, S., Yaeger, R., Hobor, S., Scala, E., Janakiraman, M., Liska, D., Valtorta, E., Schiavo, R., Buscarino, M., Siravegna, G., et al. (2012). Emergence of KRAS mutations and acquired resistance to anti-EGFR therapy in colorectal cancer. Nature 486, 532-536.

Morris, G. M., Huey, R., Lindstrom, W., Sanner, M. F., Belew, R. K., Goodsell, D. S., and Olson, A. J. (2009). AutoDock4 and AutoDockTools4: Automated docking with selective receptor flexibility. Journal of computational chemistry 30, 2785-2791.

Naylor, T. L., Tang, H., Ratsch, B. A., Enns, A., Loo, A., Chen, L., Lenz, P., Waters, N. J., Schuler, W., Dorken, B., et al. (2011). Protein kinase C inhibitor sotrastaurin selectively inhibits the growth of CD79 mutant diffuse large B-cell lymphomas. Cancer research 71, 2643-2653.

Ngo, V. N., Davis, R. E., Lamy, L., Yu, X., Zhao, H., Lenz, G., Lam, L. T., Dave, S., Yang, L., Powell, J., and Staudt, L. M. (2006). A loss-of-function RNA interference screen for molecular targets in cancer. Nature 441, 106-110.

Ngo, V. N., Young, R. M., Schmitz, R., Jhavar, S., Xiao, W., Lim, K. H., Kohlhammer, H., Xu, W., Yang, Y., Zhao, H., et al. (2011). Oncogenically active MYD88 mutations in human lymphoma. Nature 470, 115-119.

Polo, J. M., Dell'Oso, T., Ranuncolo, S. M., Cerchietti, L., Beck, D., Da Silva, G. F., Prive, G. G., Licht, J. D., and Melnick, A. (2004). Specific peptide interference reveals BCL6 transcriptional and oncogenic mechanisms in B-cell lymphoma cells. Nature medicine 10, 1329-1335.

Pop, C., Timmer, J., Sperandio, S., and Salvesen, G. S. (2006). The apoptosome activates caspase-9 by dimerization. Molecular cell 22, 269-275.

Powers, J. C., Asgian, J. L., Ekici, O. D., and James, K. E. (2002). Irreversible inhibitors of serine, cysteine, and threonine proteases. Chemical reviews 102, 4639-4750.

Rebeaud, F., Hailfinger, S., Posevitz-Fejfar, A., Tapernoux, M., Moser, R., Rueda, D., Gaide, O., Guzzardi, M., Iancu, E. M., Rufer, N., et al. (2008). The proteolytic activity of the paracaspase MALT1 is key in T cell activation. Nat Immunol 9, 272-281.

Rosenwald, A., Wright, G., Chan, W. C., Connors, J. M., Campo, E., Fisher, R. I., Gascoyne, R. D., Muller-Hermelink, H. K., Smeland, E. B., Giltnane, J. M., et al. (2002). The use of molecular profiling to predict survival after chemotherapy for diffuse large-B-cell lymphoma. The New England journal of medicine 346, 1937-1947.

Rosenwald, A., Wright, G., Leroy, K., Yu, X., Gaulard, P., Gascoyne, R. D., Chan, W. C., Zhao, T., Haioun, C., Greiner, T. C., et al. (2003). Molecular diagnosis of primary mediastinal B cell lymphoma identifies a clinically favorable subgroup of diffuse large B cell lymphoma related to Hodgkin lymphoma. The Journal of experimental medicine 198, 851-862.

Ruefli-Brasse, A. A., French, D. M., and Dixit, V. M. (2003). Regulation of NF-kappaB-dependent lymphocyte activation and development by paracaspase. Science 302, 1581-1584.

Ruland, J., Duncan, G. S., Wakeham, A., and Mak, T. W. (2003). Differential requirement for Malt1 in T and B cell antigen receptor signaling. Immunity 19, 749-758.

Sanchez-Izquierdo, D., Buchonnet, G., Siebert, R., Gascoyne, R. D., Climent, J., Karran, L., Marin, M., Blesa, D., Horsman, D., Rosenwald, A., et al. (2003). MALT1 is deregulated by both chromosomal translocation and amplification in B-cell non-Hodgkin lymphoma. Blood 101, 4539-4546.

Siegel, R., Naishadham, D., and Jemal, A. (2012). Cancer statistics, 2012. CA: a cancer journal for clinicians 62, 10-29.

Staal, J., Driege, Y., Bekaert, T., Demeyer, A., Muyllaert, D., Van Damme, P., Gevaert, K., and Beyaert, R. (2011). T-cell receptor-induced JNK activation requires proteolytic inactivation of CYLD by MALT1. EMBO J 30, 1742-1752.

Streubel, B., Lamprecht, A., Dierlamm, J., Cerroni, L., Stolte, M., Ott, G., Raderer, M., and Chott, A. (2003). T(14; 18)(q32; q21) involving IGH and MALT1 is a frequent chromosomal aberration in MALT lymphoma. Blood 101, 2335-2339.

Swerdlow, S. H., Campo, E., Harris, N. L., Jaffe, E. S., Pileri, S. A., Stein, H., Thiele, J., Vardiman, J. W (2008). World Health Organization Classification of Tumours of Haematopoietic and Lymphoid Tissues, (Lyon: IARC Press).

Vicente-Duenas, C., Fontan, L., Gonzalez-Herrero, I., Romero-Camarero, I., Segura, V., Aznar, M. A., Alonso-Escudero, E., Campos-Sanchez, E., Ruiz-Roca, L., Barajas-Diego, M., et al. (2012). Expression of MALT1 oncogene in hematopoietic stem/progenitor cells recapitulates the pathogenesis of human lymphoma in mice. Proceedings of the National Academy of Sciences of the United States of America 109, 10534-10539.

Walker, N. P., Talanian, R. V., Brady, K. D., Dang, L. C., Bump, N. J., Ferenz, C. R., Franklin, S., Ghayur, T., Hackett, M. C., Hammill, L. D., and et al. (1994). Crystal structure of the cysteine protease interleukin-1 beta-converting enzyme: a (p20/p10)2 homodimer. Cell 78, 343-352.

Wiesmann, C., Leder, L., Blank, J., Bernardi, A., Melkko, S., Decock, A., D'Arcy, A., Villard, F., Erbel, P., Hughes, N., et al. (2012). Structural determinants of MALT1 protease activity. Journal of molecular biology 419, 4-21.

Wright, G., Tan, B., Rosenwald, A., Hurt, E. H., Wiestner, A., and Staudt, L. M. (2003). A gene expression-based method to diagnose clinically distinct subgroups of diffuse large B cell lymphoma. Proceedings of the National Academy of Sciences of the United States of America 100, 9991-9996.

Yin, Q., Park, H. H., Chung, J. Y., Lin, S. C., Lo, Y. C., da Graca, L. S., Jiang, X., and Wu, H. (2006). Caspase-9 holoenzyme is a specific and optimal procaspase-3 processing machine. Molecular cell 22, 259-268.

Yu, J. W., Jeffrey, P. D., Ha, J. Y., Yang, X., and Shi, Y. (2011). Crystal structure of the mucosa-associated lymphoid tissue lymphoma translocation 1 (MALT1) paracaspase region. Proceedings of the National Academy of Sciences of the United States of America 108, 21004-21009.

Zhang, J. H., Chung, T. D., and Oldenburg, K. R. (1999). A Simple Statistical Parameter for Use in Evaluation and Validation of High Throughput Screening Assays. Journal of biomolecular screening 4, 67-73.

Cerchietti, L. C., Hatzi, K., Caldas-Lopes, E., Yang, S. N., Figueroa, M. E., Morin, R. D., Hirst, M., Mendez, L., Shaknovich, R., Cole, P. A., et al. (2010). BCL6 repression of EP300 in human diffuse large B cell lymphoma cells provides a basis for rational combinatorial therapy. The Journal of clinical investigation.

Du, P., Kibbe, W. A., and Lin, S. M. (2008). lumi: a pipeline for processing Illumina microarray. Bioinformatics 24, 1547-1548.

Gavrieli, Y., Sherman, Y., and Ben-Sasson, S. A. (1992). Identification of programmed cell death in situ via specific labeling of nuclear DNA fragmentation. The Journal of cell biology 119, 493-501.

Lam, L. T., Davis, R. E., Pierce, J., Hepperle, M., Xu, Y., Hottelet, M., Nong, Y., Wen, D., Adams, J., Dang, L., and Staudt, L. M. (2005). Small molecule inhibitors of IkappaB kinase are selectively toxic for subgroups of diffuse large B-cell lymphoma defined by gene expression profiling. Clinical cancer research: an official journal of the American Association for Cancer Research 11, 28-40.

Storey, J. D., and Tibshirani, R. (2003). Statistical significance for genomewide studies. Proceedings of the National Academy of Sciences of the United States of America 100, 9440-9445.

Subramanian, A., Tamayo, P., Mootha, V. K., Mukherjee, S., Ebert, B. L., Gillette, M. A., Paulovich, A., Pomeroy, S. L., Golub, T. R., Lander, E. S., and Mesirov, J. P. (2005). Gene set enrichment analysis: a knowledge-based approach for interpreting genome-wide expression profiles. Proceedings of the National Academy of Sciences of the United States of America 102, 15545-15550.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of modulating MALT1, comprising contacting MALT1 with an effective amount or concentration of a compound of formula (I)

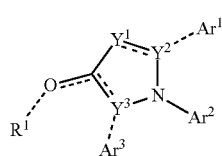

(I)

wherein a dashed bond indicates that a bond can be present or absent;

when a double bond is present between $Y^1$ and $Y^2$, $Y^1$ is N or CR, $Y^2$ is C, and $Ar^1$ is present; when a single bond is present between $Y^1$ and $Y^2$, $Y^1$ is $CR_2$, $Y^2$ is O or S, and $Ar^1$ is absent, and each independently selected R is H or (C1-C6)alkyl;

$Y^3$ is N;

$R^1$ is alkyl, alkoxyalkyl, or arylalkyl, wherein any alkyl, alkoxyalkyl, or arylalkyl, can be mono- or independently multi-substituted with halo or (C1-C6)alkoxy, provided that when a double bond is present between the oxygen atom and the ring comprising $Y^3$, $R^1$ is absent and $Ar^3$ is present, and when a single bond is present between the oxygen atom and the ring, $R^1$ is present, a double bond between $Y^3$ and the carbon atom bearing the oxygen atom is present, and $Ar^3$ is absent;

$Ar^1$ is phenyl substituted with 1-3 $J^1$ groups; $J^1$ is halo or (C1-C6)alkoxy;

$Ar^2$ is phenyl substituted with 1-3 $J^2$ groups; $J^2$ is a group of formula —N(R)C(O)—$R^2$ and $R^2$ is alkyl, aryl, or arylamino, wherein any alkyl, aryl, or arylamino is substituted with 0-2 halo, nitro, or (C1-C6)alkoxy groups, with the proviso that if $R^2$ is alkyl, the alkyl is substituted with 1-2 halo, nitro, or (C1-C6)alkoxy groups;

$Ar^3$ is phenyl substituted with 1-3 $J^3$ groups; $J^3$ is halo or (C1-C6)alkoxy, but is absent if there is double bond present between the carbon atom adjacent to $Y^3$ and $Y^3$;

or any salt, hydrate, tautomer, or stereoisomer thereof.

2. The method of claim 1, wherein the compound of formula (I) is a compound of formula (IA)

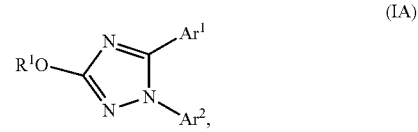

(IA)

wherein $R^1$, $Ar^1$, and $Ar^2$ are as defined for formula (I), or any salt, hydrate, tautomer, or stereoisomer thereof.

3. The method of claim 1, wherein the compound is selected from the group consisting of:

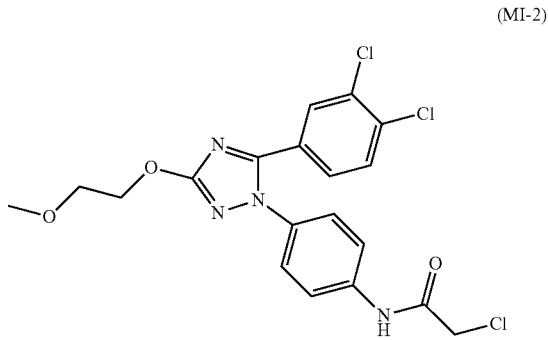

(MI-2)

-continued

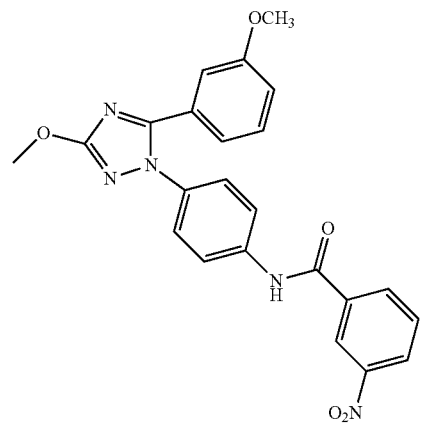
(MI-2A1)

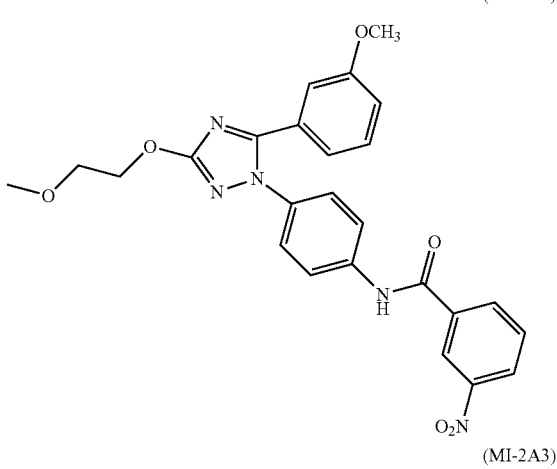
(MI-2A2)

(MI-2A3)

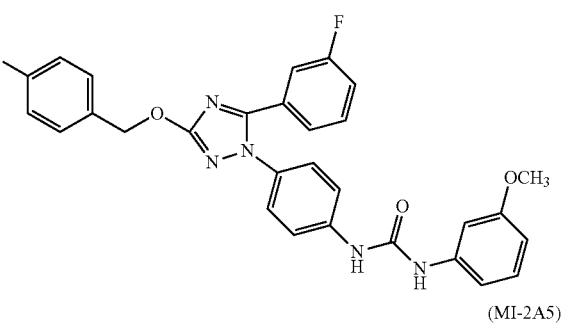

(MI-2A5)

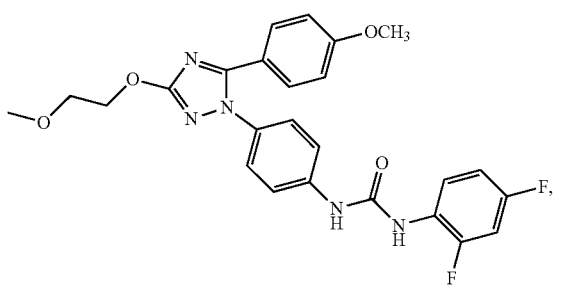

or any salt, hydrate, tautomer, or stereoisomer thereof.

4. The method of claim 1 wherein the MALT1 is disposed within a living animal.

5. The method of claim 4 wherein the living animal is a human afflicted with cancer.

6. The method of claim 1, wherein the compound is:

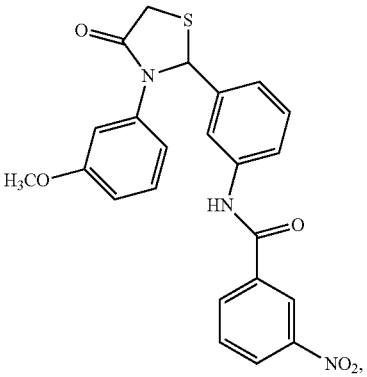
(MI-2A4)

or any salt, hydrate, tautomer, or stereoisomer thereof.

7. A method of modulating MALT1, comprising contacting MALT1 with an effective amount or concentration of a compound of formula (IB)

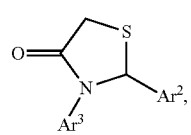
(IB)

wherein
Ar$^2$ is phenyl substituted with 1-3 J$^2$ groups; J$^2$ is a group of formula —N(R)C(O)—R$^2$ and R$^2$ is alkyl, aryl, or arylamino, wherein any alkyl, aryl, or arylamino is substituted with 0-2 halo, nitro, or (C1-C6)alkoxy groups; with the proviso that if R$^2$ is alkyl, the alkyl is substituted with 1-2 halo, nitro, or (C1-C6)alkoxy groups;
Ar$^3$ is phenyl substituted with 1-3 J$^3$ groups; J$^3$ is halo or (C1-C6)alkoxy,
and R is H or (C1-C6)alkyl;
or any salt, hydrate, tautomer, or stereoisomer thereof.

8. A method of alleviating the symptoms of lymphoma comprising administering to a patient in need thereof, an effective amount or concentration of a compound of formula (I):

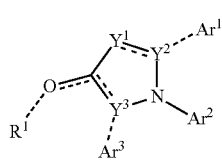
(I)

wherein
a dashed bond indicates that a bond can be present or absent;
when a double bond is present between Y$^1$ and Y$^2$, Y$^1$ is N or CR, Y$^2$ is C, and Ar$^1$ is present; when a single bond is present between Y$^1$ and Y$^2$, Y$^1$ is CR$_2$, Y$^2$ is O or S, and Ar$^1$ is absent, and each independently selected R is H or (C1-C6)alkyl;
Y$^3$ is N;
R$^1$ is alkyl, alkoxyalkyl, or arylalkyl, wherein any alkyl, alkoxyalkyl, or arylalkyl, can be mono- or independently multi-substituted with halo or (C1-C6)alkoxy, provided that when a double bond is present between the oxygen atom and the ring comprising Y³, R¹ is absent and Ar³ is present, and when a single bond is present between the oxygen atom and the ring, R¹ is present, a double bond between Y³ and the carbon atom bearing the oxygen atom is present, and Ar³ is absent;

Ar¹ is phenyl substituted with 1-3 J¹ groups; J¹ is halo or (C1-C6)alkoxy;

Ar² is phenyl substituted with 1-3 J² groups; J² is a group of formula —N(R)C(O)—R² and R² is alkyl, aryl, or arylamino, wherein any alkyl, aryl, or arylamino is substituted with 0-2 halo, nitro, or (C1-C6)alkoxy groups, with the proviso that if R² is alkyl, the alkyl is substituted with 1-2 halo, nitro, or (C1-C6)alkoxy groups;

Ar³ is phenyl substituted with 1-3 J³ groups; J³ is halo or (C1-C6)alkoxy, but is absent if there is double bond present between the carbon atom adjacent to Y³ and Y³;

or any salt, hydrate, tautomer, or stereoisomer thereof.

9. The method of claim 8, wherein the compound of formula (I) is a compound of formula (IA)

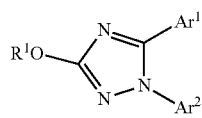
(IA)

wherein R¹, Ar¹, and Ar² are as defined for formula (I), or any salt, hydrate, tautomer, or stereoisomer thereof.

10. The method of claim 8 wherein the compound is selected from the group consisting of:

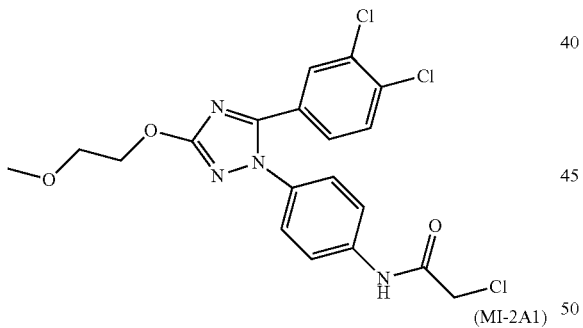
(MI-2)

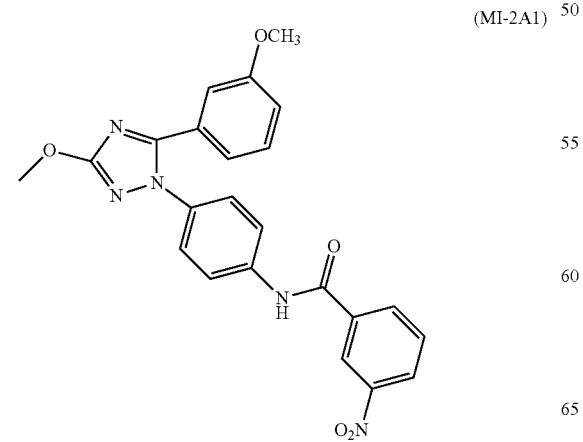
(MI-2A1)

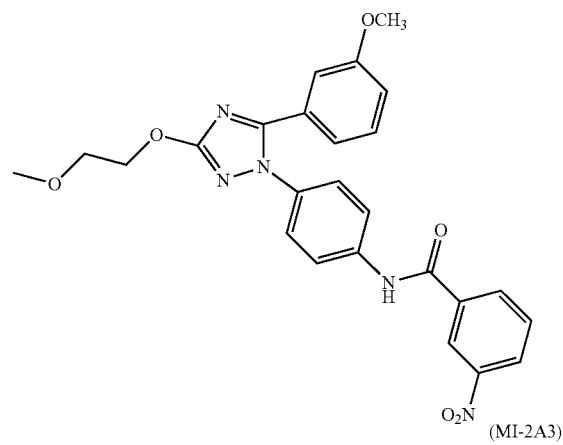
(MI-2A2)

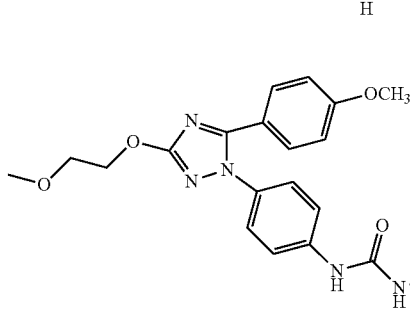
(MI-2A3)

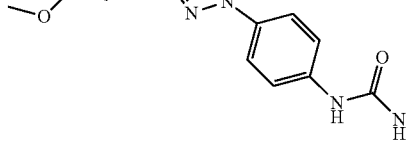
(MI-2A5)

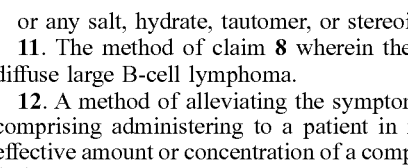

or any salt, hydrate, tautomer, or stereoisomer thereof.

11. The method of claim 8 wherein the lymphoma is a diffuse large B-cell lymphoma.

12. A method of alleviating the symptoms of lymphoma comprising administering to a patient in need thereof, an effective amount or concentration of a compound of formula (IB):

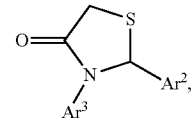
(IB)

wherein
Ar² is phenyl substituted with 1-3 J² groups; J² is a group of formula —N(R)C(O)—R² and R² is alkyl, aryl, or arylamino, wherein any alkyl, aryl, or arylamino is substituted with 0-2 halo, nitro, or (C1-C6)alkoxy groups; with the proviso that if R² is alkyl, the alkyl is substituted with 1-2 halo, nitro, or (C1-C6)alkoxy groups;
Ar³ is phenyl substituted with 1-3 J³ groups; J³ is halo or (C1-C6)alkoxy,
and R is H or (C1-C6)alkyl;
or any salt, hydrate, tautomer, or stereoisomer thereof.

13. The method of claim 12, wherein the compound is:

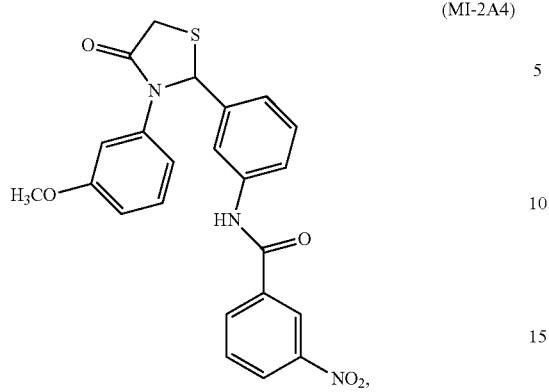

(MI-2A4)

or any salt, hydrate, tautomer, or stereoisomer thereof.

14. A method of identifying a small molecule modulator of MALT1, comprising contacting a recombinant form of MALT1 (340-789) fused with a leucine zipper dimerization motif (LZ-MALT1) and a candidate modulator compound, using the MALT1 substrate peptide LRSR linked to the fluorogen AMC (7-amino-4-methylcoumarin), such that cleavage of the Ac-LRSR-AMC substrate by MALT1 results in release of AMC and a fluorescent signal, wherein a decrease in the cleavage of the Ac-LRSR-AMC substrate by the recombinant form of MALT1 in the presence of the candidate modulator indicates that the candidate modulator is a small molecule modulator of MALT1.

* * * * *